US008883993B2

(12) United States Patent
Schneider et al.

(10) Patent No.: US 8,883,993 B2
(45) Date of Patent: Nov. 11, 2014

(54) TETRASELMIS PROMOTERS AND TERMINATORS FOR USE IN EUKARYOTIC CELLS

(71) Applicant: ExxonMobil Research and Engineering Company, Annandale, NJ (US)

(72) Inventors: Jane C. Schneider, San Diego, CA (US); Soyan Lieberman, Solana Beach, CA (US); Bo Liu, San Diego, CA (US); Eric R. Moellering, La Jolla, CA (US); John H. Verruto, San Diego, CA (US); Amanda Skaggs, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 13/693,585

(22) Filed: Dec. 4, 2012

(65) Prior Publication Data

US 2014/0154806 A1 Jun. 5, 2014

(51) Int. Cl.
| | | |
|---|---|---|
| *C07H 21/04* | (2006.01) | |
| *C12N 15/79* | (2006.01) | |
| *C12N 15/82* | (2006.01) | |
| C07H 21/00 | (2006.01) | |
| C07H 21/02 | (2006.01) | |
| C12N 1/00 | (2006.01) | |
| C12N 1/12 | (2006.01) | |
| C12N 1/13 | (2006.01) | |
| C12N 1/14 | (2006.01) | |
| C12N 5/00 | (2006.01) | |
| C12N 5/04 | (2006.01) | |
| C12N 15/00 | (2006.01) | |
| C12P 21/00 | (2006.01) | |
| C12P 21/04 | (2006.01) | |

(52) U.S. Cl.
CPC ............ *C12N 15/8221* (2013.01); *C12N 15/79* (2013.01); *C07H 21/04* (2013.01)
USPC ....... 536/24.1; 435/69.1; 435/70.1; 435/71.1; 435/410; 435/243; 435/254.1; 435/254.11; 435/257.1; 435/257.2; 435/320.1; 536/22.1

(58) Field of Classification Search
None
See application file for complete search history.

(56) References Cited

U.S. PATENT DOCUMENTS

| | | | | |
|---|---|---|---|---|
| 5,670,367 | A | 9/1997 | Dorner et al. | 435/320.1 |
| 2007/0016976 | A1 | 1/2007 | Katagiri et al. | 536/23.6 |
| 2009/0099611 | A1 | 4/2009 | Sigg et al. | 607/3 |
| 2009/0176272 | A1* | 7/2009 | Champagne et al. | 435/69.1 |
| 2009/0298143 | A1* | 12/2009 | Roessler et al. | 435/134 |

FOREIGN PATENT DOCUMENTS

| | | | | |
|---|---|---|---|---|
| WO | WO 00/62601 | 10/2000 | ............ | A01H 13/00 |
| WO | WO 2007/133558 | 11/2007 | ............ | E21B 37/00 |
| WO | WO 2011/034863 | 3/2011 | ............ | A01H 13/00 |
| WO | 2012/087676 A2 * | 6/2012 | ............... | C12P 7/64 |

OTHER PUBLICATIONS

Dunahay et al., "Manipulation of Microalgal Lipid Production Using Genetic Engineering" 57/58 Applied Biochemistry and Biotechnology 223-231 (1996).*
Walker et al. "*Microalgae* as bioreactors" 24 Plant Cell Reports 629-641 (2005).*
Hori et al. "Studies on the Ultrastructure and Taxonomy of the Genus *Tetraselmis* (Prasinophyceae) III. Subgenus parviselmis" 99 the Botanical Magazine, Tokyo 123-135 (1986).*
Kessler et al. Physical map and gene orgainization of the mitochondrial genome from the unicellular green alga *Platymonas* (Tetraselmis) subcordiformis (Prasinophyceae) 29 Plant Molecular Biology 1081-1086 (1995).*
Kessler et al., "Physical map and gene organization of the mitochondrial genome from the unicellular green alga *Platymonas* (Tetraselmis) subcordiformis (Prasinophyceae)" 29 Plant Molecular Biology 1081-1086 (1995).*
Cui, Y., et al. (2010), "Transformation of *Platymonas* (*Tetraselmis*) subcordiformis (prasinophyceae, chlorophyta) by agitation with glass beads", *World J Microbiol Biotechnol*, 26: 1653-1657.
Ferrante, P. et al. (2008), "An optimized, chemically regulated gene expression system for *Chlamydomonas*", PloS ONE, 3(9): e3200.
Gerrish, K., et al. (2000), "Pancreatic βcell-specific transcription of the pdx-1 gene", *The Journal of Biological Chemistry*, 275(5): 3485-3492.
Gibson, D., et al. (2008), "Complete chemical synthesis, assembly and cloning of a *Mycoplasma gentialium* genome", *Science*, 319: 1215-1220.
Gibson, D., et al. (2009), "Enzymatic assembly of DNA molecules up to several hundred kilobases", *Nature Methods*, 6(5): 343-345.
Hellen, C., et al., (2001), "Internal ribosome entry sites in eukaryotic mRNA molecules", *Genes & Development*, 15:1593-1612.
Henikoff, S., et al. (1992), "Amino acid substitution matrices from protein blocks", *Proc. Natl. Acad. Sci USA*, 89:10915-10919.
Kim, J., et al., (2011), "High cleavage efficiency of a 2A peptide derived from porcine teschovirus-1 in human cell lines, zebrafish and mice" *PloS One*, 6(4): e18556.
Kindle, K., et al. (1989), "Stable nuclear transformation of *Chlamydomonas* using the *Chlamydomonas* gene for nitrate reductase", *The Journal of Cell Biology*, 109 (6, Part 1), 2589-2601.
Kindle, K., et al. (1990), "High-frequency nuclear transformation of *Chlamydomonas reinhardtii*", *Proc. Natl. Acad. Sci. USA*, 87: 1228-1232.
Komar, A., et al. (2011), "Cellular IRES-mediated translation", *Cell Cycle*, 10(2): 229-240.

(Continued)

*Primary Examiner* — Anne Gussow
*Assistant Examiner* — Nancy J Leith
(74) *Attorney, Agent, or Firm* — Harness, Dickey & Pierce, P.L.C.

(57) ABSTRACT

The present invention provides novel promoter and terminator sequences for use in gene expression in eukaryotic cells, such as algal cells. The invention further provides expression cassettes comprising a promoter, as described herein, operably linked to a gene. The invention further provides expression vectors and host eukaryotic cells, such as algal cells, for expressing a protein encoded by the gene; and methods for stably transforming eukaryotic algae such as *Tetraselmis* with transgenes.

30 Claims, 9 Drawing Sheets

(56) References Cited

OTHER PUBLICATIONS

Martinez-Garcia, J., et al. (1999), "A simple, rapid and quantitative method for preparing *Arabidopsis* protein extracts for immunoblot analysis", *The Plant Journal*, 20(2): 251-257.

Méndez-Alvarez, S., et al. (1994), "Transformation of *Chlorobium limicola* by a plasmid that confers the ability to utilize thiosulfate" *Journal of Bacteriology*,176(23):7395-7397.

Mortazavi, A., et al. (2008), "Mapping and quantifying mammalian transcriptomes by RNA-Seq", *Nature Methods*, 5(7): 621-628.

Ohnuma M., et al. (2008), "Polyethylene glycol (PEG)-mediated transient gene expression in a red alga, *Cyanidioschyzon merolae* 10D", *Plant Cell Physiol*. 49(1):117-120.

Pearson, W., et al. (1988), "Improved tools for biological sequence comparison", *Proc. Natl. Acad. Sci USA*, 85: 2444-2448.

Perrone, C., et aL (1998), "The *Chlamydomonas* IDA7 locus encodes a 140 kDa dynein intermediate chain required to assemble the I1 inner arm complex", *Molecular Biology of the Cell*, 9:3351-3365.

Quinn, J., et al. (2003), "Copper response element and Crr1-dependent $Ni^2$—responsive promoter for induced, reversible gene expression in *Chlamydomonas reinhardtii*" *Eukaryotic Cell*, 2(5): 995-1002.

Smith, T., et al., (1981), "Comparison of biosequences", *Advances in Applied Mathematics*, 2: 482-489.

Watt, S., et al. "urg1: A uracil-regulatable promoter system for fission yeast with short induction and repression times", *PLoS One*, 1: e1428, (2008).

Wijffels, R., et al., (2010), "An outlook on microalgal biofuels", *Science Magazine*, 329(5993): 796-799.

Wolk, P., et al. (1984), "Construction of shuttle vectors capable of conjugative transfer from *Escherichia coli* to nitrogen-fixing filamentous cyanobacteria", *Proc. Natl. Acad. Sci. USA*, 81: 1561-1565.

International Search Report and Written Opinion dated Apr. 4, 2013 issued in PCT Application No. PCT/US2012/067788.

Becker, D.K., et al. (2000), "Genetic transformation of cavendish banana (musa spp. AAA group) cv 'grand nain' via microprojectile bombardment", *Plant Cell Reports*, 19: 229-234.

Coll., J.M. (2006), "Review. methodologies for transferring DNA into eukaryotic microalgae", *Spanish Journal of Agricultural Research*, 4(4): 316-330.

Ranjan, R., et al. (2011), "Efficient chimeric promoters derived from full-length and sub-genomic transcript promoters of figwort mosaic virus (FMV)", *J. Biotechnol.*, 152(1-2): 58-62.

Schroda, M., et al. (2006), "RNA silencing in *chlamydomonas*: mechanisms and tools", *Curr Genet* 49: 69-84.

Zhao, T., et al. (2009), "Gene silencing by artificial microRNAs in *chlamydomonas*", 58: 157-164.

\* cited by examiner

SEQUENCE LISTING

```
<160> NUMBER OF SEQ ID NOS: 36

<210> SEQ ID NO 1
<211> LENGTH: 716
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 1
cgtttctgat cctgggcctt cccgcccgc tgtaccgccg cgcccgcgct cttcgctctt      60
cgctcttcgc gattcagctc gccgccgcca ccgcgaacta gatgcccgcc ccctgcagtt    120
```

```
agcacaaccg acgcccggct agtattgcat caaccagcca ggtctggcat atggtggtac      180
cacacgtagt cgaagcaggt accccgcgtt tcgagttatc ccctggcccc ctttggtatc      240
ggatcgccgt tggcctctgg gtccagggta acgacgtgcc gcaggttgct gcagcctcgt      300
ttgaaccggc ccgaggggc ccgcccgcca gttgatgcac ggttcgcgac ccggcgcctc        360
tccgaaatat actgttcccc tctgctagct ttggtagtca ctagataccg tccggcgacg      420
tgcccctgtc gggccctggg cgacagccca gcacgtccca gtcaaactcc ggctgaccgg      480
acgctcacac acagctgact gaccctccga ccctctctt tcgggtcaca ccatcccggc       540
ccgcggaccg catagcctgt ggctcctctt ttcgccatat ctcttcttgc gtaatcttgc      600
acgcaattcc ggcgcctctg ccccgtacat cgctcctgtc tgccttttt gccccactct       660 gaccccctcc tgcatgtgcg ctttgctctc atagagctct tacgaagaaa ggcacc          716

<210> SEQ ID NO 2
<211> LENGTH: 1504
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 2
caccctcacc tctaaggatt actggtaccc caacatccag tagcgccccc ggccagctac      60
ggtgacccaa aaagctagta ctttatctga tagtggaaga actctaccgg atgtatatac      120
agcaggatat tcgtagccct gtcacatgga tgccagcaag acaccggtca ttctgtcatc      180
ttcgtaccat ataatgtcgg cctacgggta ccaagaggcg gtatgtacag gccccccgga      240
cggcgcggat gtcaggcagg cagcaaggat gtgtacgaat gcacccgtgt acatctcgcg      300
ctccatcggt agccgctgct atatagtcgc tagccacttt ttgtcgtccc gccggcatta      360
tgacatatag cgactacata gcgaccacac cagatatatc tagttgctac gttagagcga      420
cggcacgacg tacaatccta ctactgctgt cgtcgtgtac tgtgccgtgc catgttgctg      480
tgttgcgtct agctcatgta atccatgttg ctgtgtttca gcgcgcgcac accgcgagac      540
cgacgacgct cgcgcgggat ggtcagatta tttttagtac agtacagtga ggcagaaaca     600
catcaaagct tcggccgatg tcccggggcg aactttacat cacagcagaa tcgatttctc     660
aggtcgaatt gtcgtcatat agcgactata taaatgttct taattacatc agggattgca     720
caaatgcgca ctacaaacta tattattgtt cttaaaaata tacaaaaaga tgaaaaaagt     780
atcttcgtcc gcgcattatt accgtatgag cacccgtgcg agtccgagcc ctcccggtgc     840
tagtggatcc aggacacgac tagcagtgat tacatgagct agacgcaaca ttcaagaaat     900
ccacacagaa atccagaagg aaataagcag taccagtatt aagtactcct ggtggtaaca     960
ccgactatac tggtctactg ctgacgcgac ctatcacgta tattaacata ttcaatacccc    1020 gcatacatgg catatacgac ggataacacc aggtctgtat ctgtaatcaa aattatattc     1080
catatagttg ttcatccttt accggtactg gtagtgaatt acaaaaagga caattctcta     1140
gaattagaaa atcaacacat caagccgcct aaagaaaatc aacacatcct ttaccggtag     1200
agcatacgat gaatatattc gctgttacat ggtttcttgc tgtcggagcg cgcgacggcg     1260
acggcacggc tcatcgggcg tcgtatcgga agtcaggggc gcgcaaaact ccgagagcac     1320
atcagcagca catccgccgg agtattacgc aacatatcct tacagagttg cgcacggtgg    1380
cgtcgtatag tgcatcaaca acatagcaac ccctactttc tggcaaccct tccgagagct     1440
```

```
gaggatagtc gcgtcacccc acttccaact tccgtcttcc gtctcaacca ctacacccga    1500
cacc                                                                 1504

<210> SEQ ID NO 3
<211> LENGTH: 1599
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 3
cgcgagaggg gccgttgtcc agctccgcac cgatgacgga gtgtttgacc cacacctgcc      60
gccagcccag tgccagccat cagcgtgcct cgagactgtc ttccttgggc cacccagcgc     120
ggcgctacca aatcatgcca caccaatacg tccggctccc gcgcgcagtg cctctaccca     180
gtcttctcag cccagcctga cgaccgccca agcaccatc tacccagtga ttcttccttg      240
attgtgccat gcctctgcgc cttcgtatcc gacccacctg tccggctggt gccccccccc    300
cccccttccc ctacccaatg agagcatcac catcgagacg tcagcccccc gtccctgcgc    360
ggcgtagtgt cagctccgcg cgcaccttga agggcaacat ctgcagcttg cggtccggtc    420
ttactcgctg cgcggcctcc gggatgacag agcgcaggtt gagtgggata agcggtcgcg    480
cccaggggaa gctgtgcgcc atggggtcca gccgcgggtc gccgtcctgc acgcctccat    540
cgtcctccgg caaatcacct cccaggggga tggagtacat cgacagctcc gtggactcgt    600
gggccagggt cagcgccatg tccgtccctc cagttgccga ccagccctgc acgtcgccac    660
ccacaccgct ctctgcgtgc tccagtagct ccacgacatc gggtgccgcg gtcggttcgg    720 ctggcggcg ttccggtgtc atcggcgtat cggccgagcg ggactcgatg acaggaccgc     780
cgcccgcgac gtcggccgca tcactgccgc tcatcgtcgt ctcgcgccaa gttgacgggg    840
cctgtgggac aaatgctggt tgttaccaga gcttttgccg agcacagctt cctagacgcg    900
tttgagagac cgcgcggcta cctaaaaagt tggcgacacg caggcgctcg ctcgcgcagc    960
tgtccgaaca acccgacgcc ggggccagca actttacatg aagatctttt tggttacagg   1020
gagagcgtcc ggagaatgca ctttggccag caactttcct gcgccgaaag acgcgcggct   1080
ggctggctgc cgatgaacac ccgcgaccgc gcccaccgcg ctgacgatga tgcaaggat    1140 gacgtacagg gtagcagcac gcgcgcagcg tcattaggca gggtatggca cggattgagg   1200
gcatcttcta gggtataact agggctttaa gcaggctagc ttcgctgtgc ccaggctgcc   1260
tctcgaagcc aactggtgac agcatcggat agattttgcc atgctggatg ccactctggc   1320
agactgggtc gccattggca aagcgctcgg tactttattt caggaatcac gaacgatctt   1380
ctgctggtcg tccctaccgt gatgaatccg taattatttc tgcctgtcca gctctacatg   1440
atgcactctc tttatttggc tcgccgcggg aagcgtcggg gcagcagcgg caccctatcg   1500
cacgccactg acaccactct gcgcatcaca ccccaacacg ccgcccacct ctccacccgt   1560
cggtcgcctt acaactaccg ttaactttct tcggctaaa                           1599

<210> SEQ ID NO 4
<211> LENGTH: 838
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.
```

<400> SEQUENCE: 4

```
aaccggtatc gattctcgcg tattccaggc gatttcggac gcggctctcc ttttcctccg    60
ctcaacccaa gaggtagggg aaatagccca gcctgccatc ttccactttc gctgtgttag   120
ccttctgctg ctagctcatg taattatatg ttaaacacag tagcgcaaag tggagcctct   180
ctggcgctcc ttcctgccaa tttcggctct tgtccgtgta acacaccctc tgctggggtc   240
ctgtcctgct gggggccggg aaaagtgcg tgggtgtaaa tccttggata atactagcag   300
aaataatctc gtgttatata cgttgagcgt gcgcaatttc gtcatgtacc agggccagta   360
cttggcagtg ttaactccac atcatcattg gccgagaagt tacagctggc acagatatgc   420
gatcagaatg cgctgacgtg gatttacagt atttcgatgt cgacttactc tccagcgtgg   480
ccatctactg gatattcagg gagaaagggg tgctgttatt ttaacaccaa atacgcacat   540
cttcgcacat gcaactgtgc attcctgatg atatcgtctg gtatccggtt gattcatttc   600
cagatagccc cacatgccag gtcacatgac gcaatcgaat ctacgtagat aacggccggc   660
ccgtgctcta aacttgttgg cacccccgtc gtcgtgggcc agcgaggggg tccagcaccg   720
cgcgttgtcg ccttcagcct cgcgccgact cgagttcacg tcagtcttgc ttccgacccg   780
caccagctta gccagcaccc ccttcacctc ttcagcgtcc caaccaccaa tcgcaaaa     838
```

<210> SEQ ID NO 5
<211> LENGTH: 1077
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 5

```
aatccctgtt tatatttccc accaggccac aaaagaagcc tggtggcgcg tttaattgcc    60
ttccttaatt actatttcgt aatggtacct agcttggctg acgatttatc agcactctcg   120
actacagctt ttccaactac ggatgataga gcgacatcgc gacaccacgg aatcgcgatt   180
tagcgacact tagacaaagg tcaaaagaat cgccatttcg cgacacatcg acgaaggtca   240
accagcagtc gatagatgcc cgtctgcttg gtgctttaca aacgatgctg ctgccgagtc   300
gcggagccga gccaccgact actgtcgttc gagagcttct ctccctctga cgctaggagt   360
aaggaataca agaagtattc cggctgcggg taggatatta cgatttcggt gctggggcgg   420
cttcggccga tgtcccgggg cgaactttac tttactttac tttattacga tttcggcggt   480
atattgctgc gctaccggtg ccgcacgtta cccgtacggt tagttacccg taaatatcac   540
actgggaata aatcgtcatc caccattcgc gcgcgatgca aggtccggaa tccgacgtgc   600
ccagctagct cgtgtgcgca gatttaattc cattgagtcg atcttgcccg cgcgatgaac   660
acttgtattg tggataatga ccgtcgatca gatccctcgt cgcttttttgt cgaacagaaa   720
gccgtaccgg gacaatccat agctgccacg ttggcgactg ctagcgttat cattggcggg   780
tttcttatct cgatctattc gatctggcat tgcacttctt cccggtgatg cgaaatttcg   840
ccccacaaag ggaatcgagg tttacacaca cggaatatac acggaaacat ataatattca   900
tatgaaggga taccgagatt tagacacttc caacctcgtt cggacaccag gcacctagac   960
tgcgacctcc caggtttagc caaggaggcc actggacagc acgcctgaca tcacaccgtt  1020
gcgaacgttc ccttgtctcc ccagctaccg cttcaaccct ccaccctcac cattcca     1077
```

<210> SEQ ID NO 6

```
<211> LENGTH: 1042
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 6
ggcggcatgt ctgcgcaagc cctgctgcta actggttccc ggggctgaat tcggaatgta      60
tgcgtggtta ttgcgtttcc tgtgcatata cttccgtgat actttcgcca actccatcag     120
cagtagttta tggacaggcg gcggccgccg cccgccgacg acatcgtagt cgctcgtcgt     180
cagggaagtg ccgtcaggag cgtggtggcg cggcgcggc ggctcgcgcc ccggcggccg      240
gtgcggaaag gtgagcggag cgcccgtga cgtcccccett tcgcccacca ccctctacgc     300
tcaacccaca ggtgattcag caagcccctcc ggccccgccc tccaggcaac cagtcacgct    360
agtccacccc agcgtatcgc cggcccttcc cgcgctggct ttagcggcag gctcgccgcc    420
tgatccggcg cgccctcgcc gccgccaccg agaatcttcg cagcagccgc accgccggga    480
agtgtactgg gcgaggggca gcaccgtgtc gcagcaaatg tgcgaggcgc gcaggaaacg    540
caggcatgcc gctggaatcc acgcggacaa tggaggggaa aggggggat tcgtttttggt    600 ggcccccagc gtagatgggg cagggtgacc aggtctcctt ttttccttca actgcccaga    660
ttcgtccgag gttgggcatt ccttgcatta cgggaaatac cgcgcggctc tgtaatgccg    720
gttgcgattt acgccttgta cttcaaatta ttgttttcg gggaaaccca ccaggctggg     780
ttcgctagcg aagcgtccaa gcctgactga gtagctgcct gcctggtcac cacttgaggt    840
ccaccacacc gcagtcactt gccctgccgc catggcggtt ctgagtgctg ccatctctgc    900
ctctgcagct gccaggcagg ctcgccatct gcctgctgta cgccagcaca tctgacctcc    960
ccccgccccc ctgtcttcct ctctcatagg aacatcctct aggacgaaaa gactttgaga   1020
cagctctacc tgtcgaggaa aa                                            1042

<210> SEQ ID NO 7
<211> LENGTH: 991
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 7
tgcaaagggt ggatggaagg gatggatggg gagaggcgga gacggaggga aggagacgag      60 tgggaaagg atgtgtggac gagaggtggt tgccgtctgg gtgaaggctg ccctactgcc     120
cagtccctat tggccgcggg gactattgac gagccgggcc taacaaagca taaactacag    180
gattctacgg aagagaaccc gaatcctacc cggacagtcc agtgcgacct ctggccggaa    240
atctggcgga ttccttcagc agtacttaac gatgcattcg cccaggttgt ttggcctgct    300
cgcgattggg cgatacgatg cgatgtcacg aaaagtgcca cccgtcggcc gcggcgctca    360
accattggcc gctgcgatga gcgcgcagca ggctataaat gaaaggtacc gaatgtctcc    420
cgaaaacgtc tgccacgctg ttgcagagct ggcagcatga tggcaaccga gaatatgga    480 gacgatgcag ctgctgttcg cacgaggggt acgatgtaga ccctcggcat tactacgacg    540
tatgtcaaat tttgctcgac gtactgttag caaaaatgct taccgtgtat ttcatttcac    600
gtacatggac actttatcga aggggtgcat gtttttcggt cattacgaat agtcagtgcc    660
gtcaggccgt acgtttacgt tcgaatttga gagcccaatc aagccaaggt gattccgcca    720
```

```
gggtgtcgca gtgatttggt cagtcactac aaaggcttat caaatctaaa tcacgcgatt    780
gctgccagcg tcatcaaatc gtcttatcag tatattgtaa ctgtgctgca caatcctgtg    840
ggacctgctg cttccacccc gcacaagtca gcgtccaaag gcctctgcct ggcgggctac    900
ttcaacctct tcgagcatcc tgcaactcca acagtcccgc tctctccctc gttatccttc    960
cgtatcctct cctccccacc cttccgctac c                                   991

<210> SEQ ID NO 8
<211> LENGTH: 991
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 8
ggtagcggaa gggtggggag gagaggatac ggaaggataa cgagggagag agcgggactg     60
ttggagttgc aggatgctcg aagaggttga agtagcccgc caggcagagg cctttggacg    120
ctgacttgtg cggggtggaa gcagcaggtc ccacaggatt gtgcagcaca gttacaatat    180
actgataaga cgatttgatg acgctggcag caatcgcgtg atttagattt gataagcctt    240
tgtagtgact gaccaaatca ctgcgacacc ctggcggaat caccttggct tgattgggct    300
ctcaaattcg aacgtaaacg tacggcctga cggcactgac tattcgtaat gaccgaaaaa    360
catgcacccc ttcgataaag tgtccatgta cgtgaaatga aatacacggt aagcattttt    420
gctaacagta cgtcgagcaa aatttgacat acgtcgtagt aatgccgagg gtctacatcg    480 taccctcgt gcgaacagca gctgcatcgt ctcatatatt ctcggttgcc atcatgctgc    540
cagctctgca acagcgtggc agacgttttc gggagacatt cggtaccttt catttatagc    600
ctgctgcgcg ctcatcgcag cggccaatgg ttgagcgccg cggccgacgg gtggcacttt    660
tcgtgacatc gcatcgtatc gcccaatcgc gagcaggcca aacaacctgg gcgaatgcat    720
cgttaagtac tgctgaagga atccgccaga tttccggcca gaggtcgcac tggactgtcc    780
gggtaggatt cgggttctct tccgtagaat cctgtagttt atgctttgtt aggcccggct    840
cgtcaatagt ccccgcggcc aatagggact gggcagtagg gcagccttca cccagacggc    900
aaccacctct cgtccacaca tcctttcccc actcgtctcc ttccctccgt ctccgcctct    960
ccccatccat cccttccatc caccctttgc a                                   991

<210> SEQ ID NO 9
<211> LENGTH: 1011
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 9
agcaagcgct gtgcaatcaa atcaatgctg tctgcgaatg gcgcgtcgtg gcagcggtgc     60
atgtgccgga gcaaggtttg cgcgcacagg gttggcggtg cacgactgtg gctgttgggc    120
agcaaggggg gggtagcaca gtccttgacg cggtgccaag gcggtcctgt ccgtcaggtg    180
agggctgctt ggcctgtgag ctggaggcgc cactgctagc aggacgccca cgatagagta    240
agcgctttct tctggcgcaa catttaatca cacttctgta tctccttttc cctgccagtc    300
tgcttgctgg cgcacttgta ccgtttagtg tggttgtacg ctcgcttcct ccctcagccc    360
```

```
gcggcaggag tgctagggaa attcttgcac agagcacaac cgctctcaat gtgacgttga    420
tcggcactct ttcccatgga cagtcaactt ccactggcat tgtttaaatg ctattagcca    480
cttccttaca cgcgaaaaat agcacaagaa ataagcgtcc ctactactca ccgcaccgtc    540
gtgaccatac atcactggtt ccatattgag ctcaggaact cttcagcgcg ttgcccgacg    600
ggagtgccag ggtgcggccg ccatccaaca tgaaactctg cccggtgatg aagccagatg    660
tgctggagga tcccaggaaa ataccgcct cggcaacgtc tgtgggctgc ctgcaatcag     720
aagtgcacag caattgagga tgctgccaaa tggttgatgt gaagtcaggg gagttttgtc    780
atctgcagta tggcacaggg ggggtagatt gagagtctca cccgatgcgg cccagtggat    840
ggcagctagc agactcagcc aggaaggtct cagtgccttc agtcccaagc ccagcacttg    900
ccaaaaagtc ggtctcaatc ctggcggttc acagcagcac atcttgaatg ttacgcgtat    960
gtgatggggc ctggatgggc agggctccaa ccaccaaaca cgaccatttg g            1011
```

<210> SEQ ID NO 10
<211> LENGTH: 1223
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 10

```
tgaggcctat cctcgctgct cataccacca ttcatccaca aatagcagta gccagcacct    60
gttgccctct gtgcgcaagt gtgtcagata ggactgcaaa tatgaaaacc agccaaattc    120
ctgtactgga attggttact ctccactttt ttttaggtag aactgtaacc atatcttgca    180
aaaataccaa caatgcaagg aaggagacat tgtgcaggaa tacatgctac ctaattctgg    240
gggcgacgtt ctgaggtttt cagttgcgga cagcaatgca gcttcaagac aacaatggca    300
tgccttgtcc ctttccgcac atggttatgg catgaatagc aagatgttca ctagcgggct    360
gctgccattc actgattgtt gatgaatgcg cacatttctc tgggtagtgg agggtaattt    420
tggcgttttg ggtattatcc gaaatgccta gtttccaaca tcgtggatat gctcttcagt    480
ctcattgtag catgctgccc gcctgttttg aaatgcagtg ggttaaattg gtgcagaaga    540
gggggcagat tctgtcacat gcaactaaac atcaagggac aatgacaaaa ttgtttccca    600
ctaggacgat aaatccgcac tatataatga gacagtgagt gcttttccac caacctccat    660
gttgatagaa atgccaacac cagatcgatg ggcaacatta tcggcactcg gccatgtagg    720
cactcatcgc aaatcccggc actggtggtg cgtgttgggc tgccactgta agcgcatgcc    780
cgctgcagag actccactga tgaaggcgct ccagcgaaga tataagcgaa aactgtgaca    840
cagcaaccca ccagttgact tcactggcaa gaagtacctt ctttgttagc atccagtaga    900
ctgacctcaa tatgcactcg cattaattcg actataacga atcatggaac taccgaagca    960
tgcaatacgt aacatatccg ctgtgtaagt ataaatgagc ggtgcgcatg tgctatgatg    1020
ttgcgcagca tagtttatga gttgttatta aggaggttgc tactgggctt gccaaatgat    1080
tcagttctgt gagccagatc cttgagattt ggtgtcgcga cgagcacatg taaacctta    1140 aaaccgttat atcacttaat taatgacaca gcatatgaaa cctagcttaa gttggtaccg    1200
tcgtggacaa gtacaagatc gcc                                            1223
```

<210> SEQ ID NO 11
<211> LENGTH: 40
<212> TYPE: DNA

```
<213> ORGANISM: Artificial Sequence
<220> FEATURE:
<223> OTHER INFORMATION: WT105ActinPro-EcoRI

<400> SEQUENCE: 11
aaacgacggc cagtgaattc cgtttctgat cctgggcctt                                  40

<210> SEQ ID NO 12
<211> LENGTH: 40
<212> TYPE: DNA
<213> ORGANISM: Artificial Sequence
<220> FEATURE:
<223> OTHER INFORMATION: WT105ActinPro-BLE-3

<400> SEQUENCE: 12
gacgtcagct tggccaacat ggtgcctttc ttcgtaagag                                  40

<210> SEQ ID NO 13
<211> LENGTH: 39
<212> TYPE: DNA
<213> ORGANISM: Artificial Sequence
<220> FEATURE:
<223> OTHER INFORMATION: WT105ActinTER-BLE-5

<400> SEQUENCE: 13
tcgccgaaga gcaggattaa gcaagcgctg tgcaatcaa                                   39

<210> SEQ ID NO 14
<211> LENGTH: 40
<212> TYPE: DNA
<213> ORGANISM: Artificial Sequence
<220> FEATURE:
<223> OTHER INFORMATION: WT105ActinTER-HindIII

<400> SEQUENCE: 14
accatgatta cgccaagctt ccattggtgg ttggagccct                                  40

<210> SEQ ID NO 15
<211> LENGTH: 40
<212> TYPE: DNA
<213> ORGANISM: Artificial Sequence
<220> FEATURE:
<223> OTHER INFORMATION: BLE-ActinWT105-5

<400> SEQUENCE: 15
ctcttacgaa gaaaggcacc atgttggcca agctgacgtc                                  40

<210> SEQ ID NO 16
<211> LENGTH: 39
<212> TYPE: DNA
<213> ORGANISM: Artificial Sequence
<220> FEATURE:
<223> OTHER INFORMATION: BLE-ActinWT105-3

<400> SEQUENCE: 16
ttgattgcac agcgcttgct taatcctgct cttcggcga                                   39

<210> SEQ ID NO 17
<211> LENGTH: 40
<212> TYPE: DNA
<213> ORGANISM: Artificial Sequence
<220> FEATURE:
<223> OTHER INFORMATION: WT105ActinPro-PciI

<400> SEQUENCE: 17
gctggccttt tgctcacatg tcgtttctga tcctgggcct                                  40
```

<210> SEQ ID NO 18
<211> LENGTH: 40
<212> TYPE: DNA
<213> ORGANISM: Artificial Sequence
<220> FEATURE:
<223> OTHER INFORMATION: WT105ActinPro-GFP-3

<400> SEQUENCE: 18
cccggattcg tccgactcca tggtgccttt cttcgtaaga          40

<210> SEQ ID NO 19
<211> LENGTH: 40
<212> TYPE: DNA
<213> ORGANISM: Artificial Sequence
<220> FEATURE:
<223> OTHER INFORMATION: WT105ActinTER-GFP-5

<400> SEQUENCE: 19
ccgacgctgg agaagagtaa agcaagcgct gtgcaatcaa          40

<210> SEQ ID NO 20
<211> LENGTH: 40
<212> TYPE: DNA
<213> ORGANISM: Artificial Sequence
<220> FEATURE:
<223> OTHER INFORMATION: WT105ActinTER-PciI

<400> SEQUENCE: 20
taacgcagga agaacatgt ccaaatggtc gtgtttggtg           40

<210> SEQ ID NO 21
<211> LENGTH: 40
<212> TYPE: DNA
<213> ORGANISM: Artificial Sequence
<220> FEATURE:
<223> OTHER INFORMATION: GFP-ActinWT105-5

<400> SEQUENCE: 21
tcttacgaag aaaggcacca tggagtcgga cgaatccggg          40

<210> SEQ ID NO 22
<211> LENGTH: 40
<212> TYPE: DNA
<213> ORGANISM: Artificial Sequence
<220> FEATURE:
<223> OTHER INFORMATION: GFP-ActinWT105-3

<400> SEQUENCE: 22
ttgattgcac agcgcttgct ttactcttct ccagcgtcgg          40

<210> SEQ ID NO 23
<211> LENGTH: 20
<212> TYPE: DNA
<213> ORGANISM: Artificial Sequence
<220> FEATURE:
<223> OTHER INFORMATION: BLE-5

<400> SEQUENCE: 23
atgttggcca agctgacgtc                                20

<210> SEQ ID NO 24
<211> LENGTH: 20
<212> TYPE: DNA
<213> ORGANISM: Artificial Sequence
<220> FEATURE:

<223> OTHER INFORMATION: BLE-3

<400> SEQUENCE: 24
ttaatcctgc tcttcggcga                                              20

<210> SEQ ID NO 25
<211> LENGTH: 20
<212> TYPE: DNA
<213> ORGANISM: Artificial Sequence
<220> FEATURE:
<223> OTHER INFORMATION: NaHtransB5

<400> SEQUENCE: 25
tggtggtgcc caagtacaac                                              20

<210> SEQ ID NO 26
<211> LENGTH: 20
<212> TYPE: DNA
<213> ORGANISM: Artificial Sequence
<220> FEATURE:
<223> OTHER INFORMATION: NaHtransC3

<400> SEQUENCE: 26
gaggagctga acatggtccc                                              20

<210> SEQ ID NO 27
<211> LENGTH: 26
<212> TYPE: DNA
<213> ORGANISM: Artificial Sequence
<220> FEATURE:
<223> OTHER INFORMATION: LF-SGE5320F1

<400> SEQUENCE: 27
cgccagaaga aagcgcttac tctatc                                       26

<210> SEQ ID NO 28
<211> LENGTH: 25
<212> TYPE: DNA
<213> ORGANISM: Artificial Sequence
<220> FEATURE:
<223> OTHER INFORMATION: BLEcodon3

<400> SEQUENCE: 28
atgttggcca agctgacgtc ggcgg                                        25

<210> SEQ ID NO 29
<211> LENGTH: 6549
<212> TYPE: DNA
<213> ORGANISM: Artificial Sequence
<220> FEATURE:
<223> OTHER INFORMATION: pSGE05320 vector

<400> SEQUENCE: 29
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtcg   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt ccgttctga tcctgggcct   420 tccccgcccg ctgtaccgcc gcgccccgcgc tttcgctctt gtcaatctcg attcagctcg   480

```
ccgccgccac cgcgaactag atgcccgccc cctgcagtta gcacaaccga cgcccggcta    540
gtattgcatc aaccagccag gtctggcata tggtggtacc acacgtagtc gaagcaggta    600
ccccgcgttt cgagttatcc cctggccccc tttggtatcg gatcgccgtt ggcctctggg    660
tccagggtaa cgacgtgccg caggttgctg cagcctcgtt tgaaccggcc cgaggggcc     720
cgcccgccag ttgatgcacg gttcgcgacc cggcgcctct ccgaaatata ctgttcccct    780
ctgctagctt tggtagtcac tagataccgt ccggcgacgt gccctgtcg ggccctgggc     840
gacagcccag cacgtcccag tcaaactccg gctgaccgga cgctcacaca cagctgactg    900
accctccgac ccctctcttt cgggtcacac catcccggcc cgcggaccgc atagcctgtg    960
gctcctcttt tcgccatatc tcttcttgcg taatcttgca cgcaattccg gcgcctctgc   1020
cccgtacatc gctcctgtct gccttttttg ccccactctg acccctcct gcatgtgcgc    1080
tttgctctca tagagctctt acgaagaaag gcaccatgtt ggccaagctg acgtcggcgg   1140
ttccggtcct gacagcgcgt gacgtggccg gagcggtgga gttttggact gaccggctcg   1200
ggtttagccg ggacttcgtc gaggacgatt tcgctggcgt agtacgcgat gacgtgaccc   1260
tctttatctc ggcggtgcaa gaccaggtcg tccccgacaa cacgctggct tgggtctggg   1320
tgcgaggcct tgatgagctg tacgccgagt ggtccgaggt ggtttccacc aacttccgcg   1380
acgcgagcgg tcctgccatg accgagattg gcgaacagcc gtgggggagg gagttcgcac   1440
tccgcgaccc agcaggcaat tgcgtgcact tcgtcgccga agagcaggat taaagcaagc   1500
gctgtgcaat caaatcaatg ctgtctgcga atggcgcgtc gtggcagcgg tgcatgtgcc   1560
ggagcaaggt ttgcgcgcac agggttggcg gtgcacgact gtggctgttg ggcagcaagg   1620
gggggtagc acagtccttg acgcggtgcc aaggcggtcc tgtccgtcag gtgagggctg    1680
cttggcctgt gagctggagg cgccactgct agcaggacgc ccacgataga gtaagcgctt   1740
tcttctggcg caacatttaa tcacacttct gtatctcctt ttccctgcca gtctgcttgc   1800
tggcgcactt gtaccgttta gtgtggttgt acgctcgctt cctccctcag cccgcggcag   1860
gagtgctagg gaaattcttg cacagagcac aaccgctctc aatgtgacgt tgatcggcac   1920
tctttcccat ggacagtcaa cttccactgg cattgtttaa atgctattag ccacttcctt   1980
acacgcgaaa aatagcacaa gaaataagcg tccctactac tcaccgcacc gtcgtgacca   2040
tacatcactg gttccatatt gagctcagga actcttcagc gcgttgcccg acgggagtgc   2100
cagggtgcgg ccgccatcca acatgaaact ctgcccggtg atgaagccag atgtgctgga   2160
ggatcccagg aaaaataccg cctcggcaac gtctgtgggc tgcctgcaat cagaagtgca   2220
cagcaattga ggatgctgcc aaatggttga tgtgaagtca ggggagtttt gtcatctgca   2280
gtatggcaca ggggggtag attgagagtc tcacccgatg cggcccagtg gatggcagct    2340
agcagactca gccaggaagg tctcagtgcc ttcagtccca agcccagcac ttgccaaaaa   2400
gtcggtctca atcctggcgg ttcacagcag cacatcttga atgttacgcg tatgtgatgg   2460
ggcctggatg ggcagggctc caaccaccaa tggaagcttg gcgtaatcat ggtcatagct   2520
gtttcctgtg tgaaattgtt atccgctcac aattccacac aacatacgag ccggaagcat   2580
aaagtgtaaa gcctggggtg cctaatgagt gagctaactc acattaattg cgttgcgctc   2640
actgcccgct ttccagtcgg gaaacctgtc gtgccagctg cattaatgaa tcggccaacg   2700
cgcggggaga ggcggtttgc gtattgggcg ctcttccgct tcctcgctca ctgactcgct   2760
gcgctcggtc gttcggctgc ggcgagcggt atcagctcac tcaaaggcgg taatacggtt   2820
```

```
atccacagaa tcaggggata acgcaggaaa gaacatgttg gcctggccat tacatgcagt    2880
atggcattgg cagatattcg cagtaagttg gttggtcttc tcaatgggtg tggcacgttg    2940
gccactggct cacgcacacg ctaacatcta caacagcacg tccgccaaaa ctgcggggtc    3000
gcaaaccaag tcgacgtgcc tacctccccc tgatcctcct gtggctaatt gaccgtgggc    3060
cgaccccaca ccgaccctgg tcaccactgc ccttcgccta gccccctagcg cgaaagcctc    3120
cgagctccga tcccgtatca atcagcgaaa tcggccatcc cggcaagtaa agctcttctc    3180
catggtacag gcggtccagc tgctgccaga acgcttactc ttctccagcg tcggcgtcag    3240
gagttttaaa ggcgtgctgg tactccacga tgccgagctc tgtgttgcta tgatcctcct    3300
caaccctccg gaaggcgaac atgggtccgc cgttttgcaa gatgctgggg tgaattgccg    3360
acttaaagtg catgtgcgag tcgacgacgg acgagtagta gccgccatcg cgcagggaaa    3420
aagtgcgggt gaacgacccg tcgaggtcgt tgtcgcccat agggtgaagg tgctcaacgg    3480
tcgcattgct gcgaatgatt ttatcggtga agatcacgct gtcctctggg aagcccgtac    3540
ccatcacctt gaagtcgccg attaccctgc cagcttcgta tcgatagcta aaggacacat    3600
gaaggactcc gccatcctcg tacttctcta tgcgtgtatt ggtataccct ccgttgttta    3660
tcgcatggag gaatgggttc tcgtagccgg aggggtacgt cccgaaatgg tagaagccgt    3720
accccatcac gtgggacaac agatacgggc tgaacgtgag cgcacccttc gtgctcttca    3780
tcttatttgt catacgcccc tgctccgtcg tcccctcgcc accgcccacc agttcaaatt    3840
cgacgccgtt cagggtaccg gtgatccggc actcgatctc cattgccggc agcccggatt    3900
cgtccgactc catggtttga atcctgcgtg tcacgtccgc gagagcagaa cgaagtgatc    3960
ggagggctgc cacctcggca aagctaagca ttcttcgcct gcgctagtgc atgacaactc    4020
taccctttcc attcaatgtg atgtgctacg atgctgcaac agaagcgagg caacgcagcg    4080
aggctctacc gcaacgcacg cgcaggtgtt tggctctcta cctgaagata aggtagatc     4140
gggggaacgg ggtcacaagt ctggtagcta tgtgttgagt tgagagtgca agcccgggctt   4200
ctattgtatg tccggatcgg aattggcgcg aactgttcaa atgggctgcc accagcagcc    4260
ccgagctgcc agcgctgagt tcctgaaacc ctttcattga gtataaataa ccaaaacact    4320
aggaagacgg gtggacacga ggacgcgcaa cgggcgactc tgttcgcagc gccccgacct    4380
ttgggacacc gccttctctg ctcacgtctg cccctcacgg cgcgcagcca ggcgccggca    4440
cgtgacccgg agccggacgt gcaatgcagc tcgccacatg catgcgcgcc accctgcgcc    4500
actccattgc cacgcatgcg acacggctcg agcgctgggc aggaggtgct cgtgcccct     4560
cgtcttccct gatcttcccg aagggggccat gccttctctc gtgaggaatt gtggttagtg    4620
cgcccgctgc ggggcttgtg ccacctgtgt gggatgtggc ccctcgaac atgtgagcaa     4680
aaggccagca aaaggccagg aaccgtaaaa aggccgcgtt gctggcgttt ttccataggc    4740
tccgcccccc tgacgagcat cacaaaaatc gacgctcaag tcagaggtgg cgaaacccga    4800
caggactata aagataccag gcgtttcccc ctggaagctc cctcgtgcgc tctcctgttc    4860
cgaccctgcc gcttaccgga tacctgtccg cctttctccc ttcgggaagc gtggcgcttt    4920
ctcatagctc acgctgtagg tatctcagtt cggtgtaggt cgttcgctcc aagctgggct    4980
gtgtgcacga accccccgtt cagcccgacc gctgcgcctt atccggtaac tatcgtcttg    5040
agtccaaccc ggtaagacac gacttatcgc cactggcagc agccactggt aacaggatta    5100
gcagagcgag gtatgtaggc ggtgctacag agttcttgaa gtggtggcct aactacggct    5160
acactagaag gacagtattt ggtatctgcg ctctgctgaa gccagttacc ttcggaaaaa    5220
```

```
gagttggtag ctcttgatcc ggcaaacaaa ccaccgctgg tagcggtggt ttttttgttt    5280
gcaagcagca gattacgcgc agaaaaaaag gatctcaaga agatcctttg atcttttcta    5340
cggggtctga cgctcagtgg aacgaaaact cacgttaagg gattttggtc atgagattat    5400
caaaaaggat cttcacctag atccttttaa attaaaaatg aagttttaaa tcaatctaaa    5460
gtatatatga gtaaacttgg tctgacagtt accaatgctt aatcagtgag gcacctatct    5520
cagcgatctg tctatttcgt tcatccatag ttgcctgact ccccgtcgtg tagataacta    5580
cgatacggga gggcttacca tctggcccca gtgctgcaat gataccgcga gacccacgct    5640
caccggctcc agatttatca gcaataaacc agccagccgg aagggccgag cgcagaagtg    5700
gtcctgcaac tttatccgcc tccatccagt ctattaattg ttgccgggaa gctagagtaa    5760
gtagttcgcc agttaatagt ttgcgcaacg ttgttgccat tgctacaggc atcgtggtgt    5820
cacgctcgtc gtttggtatg gcttcattca gctccggttc ccaacgatca aggcgagtta    5880
catgatcccc catgttgtgc aaaaaagcgg ttagctcctt cggtcctccg atcgttgtca    5940
gaagtaagtt ggccgcagtg ttatcactca tggttatggc agcactgcat aattctctta    6000
ctgtcatgcc atccgtaaga tgcttttctg tgactggtga gtactcaacc aagtcattct    6060
gagaatagtg tatgcggcga ccgagttgct cttgcccggc gtcaatacgg gataataccg    6120
cgccacatag cagaacttta aaagtgctca tcattggaaa acgttcttcg gggcgaaaac    6180
tctcaaggat cttaccgcgt tgagatcca gttcgatgta acccactcgt gcacccaact    6240
gatcttcagc atcttttact ttcaccagcg tttctgggtg agcaaaaaca ggaaggcaaa    6300
atgccgcaaa aaagggaata agggcgacac ggaaatgttg aatactcata ctcttccttt    6360
ttcaatatta ttgaagcatt tatcagggtt attgtctcat gagcggatac atatttgaat    6420
gtatttagaa aaataaacaa ataggggttc cgcgcacatt tccccgaaaa gtgccacctg    6480
acgtctaaga aaccattatt atcatgacat taacctataa aaataggcgt atcacgaggc    6540
cctttcgtc                                                            6549
```

<210> SEQ ID NO 30
<211> LENGTH: 378
<212> TYPE: DNA
<213> ORGANISM: Artificial Sequence
<220> FEATURE:
<223> OTHER INFORMATION: Streptoalloteichus hindustanus bleomycin
resistence (ble) gene codon-optimized for expression in
Chlamydomonas reinhardtii

<400> SEQUENCE: 30

```
atgttggcca agctgacgtc ggcggttccg gtcctgacag cgcgtgacgt ggccggagcg     60
gtggagtttt ggactgaccg gctcgggttt agccgggact cgtcgagga cgatttcgct    120
ggcgtagtac gcgatgacgt gaccctcttt atctcggcgg tgcaagacca ggtcgtcccc    180
gacaacacgc tggcttgggt ctgggtgcga ggccttgatg agctgtacgc cgagtggtcc    240
gaggtggttt ccaccaactt ccgcgacgcg agcggtcctg ccatgaccga gattggcgaa    300
cagccgtggg ggagggagtt cgcactccgc gacccagcag gcaattgcgt gcacttcgtc    360
gccgaagagc aggattag                                                 378
```

<210> SEQ ID NO 31
<211> LENGTH: 4590
<212> TYPE: DNA
<213> ORGANISM: Chlamydomonas reinhardtii

```
<400> SEQUENCE: 31 tcgaggggc cacatcccac acaggtggca caagccccgc agcgggcgca ctaaccacaa        60
ttcctcacga gagaaggcat ggcccttcg ggaagatcag ggaagacgag ggggcacgag       120
cacctcctgc ccagcgctcg agccgtgtcg catgcgtggc aatggagtgg cgcagggtgg      180
cgcgcatgca tgtggcgagc tgcattgcac gtccggctcc gggtcacgtg ccggcgcctg      240
gctgcgcgcc gtgaggggca gacgtgagca gagaaggcgg tgtcccaaag gtcgggcgc      300
tgcgaacaga gtcgcccgtt gcgcgtcctc gtgtccaccc gtcttcctag tgttttggtt     360
atttatactc aatgaaaggg tttcaggaac tcagcgctgg cagctcgggg ctgctggtgg     420
cagcccattt gaacagttcg cgccaattcc gatccggaca tacaatagaa gcccggcttg     480
cactctcaac tcaacacata gctaccagac ttgtgacccc gttcccccga tctacctta    540
tcttcaggta gagagccaaa cacctgcgcg tgcgttgcgg tagagcctcg ctgcgttgcc     600
tcgcttctgt tgcagcatcg tagcacatca cattgaatgg aaagggtaga gttgtcatgc    660
actagcgcag gcgaagaatg cttagctttg ccgaggtggc agccctccga tcacttcgtt   720
ctgctctcgc ggacgtgaca cgcaggattc aaaatggctg acgagggcga ggtctctgct    780
ctggtgtgcg acaatggttc gggcatggtg aaggtgagca ggtgttcaga ggcggtcgcg    840
tcgcgcgacg aagcgggaag gtggccggac tccttgctg gaaggtttgg ccgtcttggg    900
cgcgccagca gctcaacttc gatctggtca ttctaatgag cacaatcaca cgtagtggcg    960
tggggacttc catttaactt gggcgttggg cctggcgtgg gccccgcgct gcagcgcgtt   1020
gttcgagcaa acctgatgct ggcgatcgct gtgtcgccgt gtccgcaggc tggctttgct   1080
ggtgatgatg cccctcgcgc tgtgttcccc tccatcgtgg gccggcccg ccacaccggt    1140
gtgatggtcg ggatgggcca gaaggtgcgc tcgcttttcg tttggctcgt gcatgcttgc   1200
acgcgttata tgcatgtatg aagccatgtt gagcatactt gcttctttgg actctgcagg   1260
actcgtacgt tggcgacgag gcgcagtcca agcgcggtat tctgactctg cgctacccca   1320
ttgagcacgg tattgtgacc aactgggacg acatggagaa gatctggcac cacaccttct   1380
tcaacgagct gcgcgtggcg cccgaggtgg gtatttggca cgcacacatg tcccggacat   1440
cctcgccacc tgcacgcgtc gctgaacttc ccttgccgcc cctcgcgctg cctctgcagg   1500
agcaccccgt gctgctgact gaggcccccc tgaaccccaa ggccaaccgc gagaagatga   1560
cccaggtgcg ggggttggtt tgtttgcaca agtcacagac ctaccgttcc ctgcaaaacc   1620
gcctacctcc aaagctccgc ccttactcca caccaatttc ttctttgctc cccgcagatc   1680
atgttcgaga ccttcaacgt gccggccatg tacgtggcta tccaggtgag agaggtcgag   1740
acagcggagt aacggccgcg gcatcgcggc acgcggcagc agcccgagcc ggacagtaag   1800
gcaggcccat acaacagcgg tcggcggcac agtcggcgac acatgtccgc accacgtgga   1860
cgctggcata ccagccagct gttgtgctgt cgcttggcgc gtgacatgtg cgtgaaggcc   1920
ctggcccctc ccctccccat caaccactgc cattgactcg caccctcact cccgcgcctc   1980
cccaccccgc cgtccaggcc gtgctgtccc tgtacgccag cggccgcacc accggtatcg   2040
tgctggactc tggcgacggc gtgacgcaca cggtgcccat ctacgagggc tacgcgctgc   2100
cgcacgccat cctgcgcctg gacctggcgg gccgcgacct caccgattac ctgatgaaga   2160
tcctcatggg tgggtgcact agccgcggtt tgttgcagtt ggtcggttct gtttgttcca   2220
ggtttcaatg ggtgggctgg gtgggccggt tggttttgtt tggggggggt tgcagtgagt   2280
ggatagtggg ttggatgcag aacggcatga taggacagga cagcatggtg catgtgtcaa   2340
```

```
gcaggagcct caggccagcc agctgtcaga caaggccaag gtggcgactt gcagtctgca    2400
tcacatgcgg gagggtgggg gagtcgatat gggcaagcgg agtcggaggt taggtcacga    2460
tggcagcgaa ccgccgacgg gcagcatggc gcggcattgc cttgcgccgg agtctgaagc    2520
taatcgcgtc actgctcgtg agaagcagat tctaatcaat gccagggtgg tgaatggcgt    2580
gaaggaagga acgagggagt ggggcaaggc gttgattggg gaagcgatgc ccatatgggg    2640
accgggaggt cgtggaacgt ggggtgggtg gtgttggaac gcagtcagca gtcagttggg    2700
gaggaaggca gcacagtcac aatgccaacc gccagcagga tgtgcgcgag cggcatgctg    2760
gaccccaaac cgccgcggtc atgcttacat ttccccaccg agctaaccac aacatctcct    2820
tcctcctccc ttcgacagag cgcggctact cgttccacca cacggccgag cgcgaaatcg    2880
tgcgcgacat caaggagaag ctgtgctacg tggccctgga cttcgagcag gagatggcca    2940
ccgcgctgtc cagctcggcg ctggagaaga cctacgagct gcccgacggc caggtgggag    3000
ctagggcgtt tgctaggggg gatggtgatg gttgagtttt gggtaaagag ggcgggaggt    3060
ggggtttcaa gggattggta tggggctacg agaacaagaa ccaaacggga agtgacaggg    3120
ctgcatgttc gatttagatg tggtggtgaa ggggttcaa ccgggtgaaa gtagatggtg     3180
cagcaggggc gggaggaggt cggagagcgg gcggctgccg gatggcgcag ctgctgcaag    3240
gcagcaacga gcagccaccg cagaacccaa catctaaaca tcgccgcctc tgccaccaca    3300
caacatcacg acgcaccaca caacgcagat gatcaccatc ggcaacgagc gtttccgctg    3360
ccccgaggtg ctgtttaacc ccaacatgat tggcatggag gcggtgggca tccacgacac    3420
caccttcaac tccatcatga agtgcgatgt ggacatccgc aaggacctct acaacaacat    3480
cgtgctgtcg ggaggcacca ccatgttccc cggtgagtgg gagaggggcg gcgccgttga    3540
gcaggggcgc aggaggtcat ggggactgtg tgtggggggg gggaggcagg cgtgaatggg    3600
gaccggcgtg acggactgcc gcagggaacg aggtgccaac ggcccggacc ggtgagggcg    3660
gctctgatga cttggtcgtc aatcgtcacc ttatcctcat cgccctccct ccctgcccct    3720
tcaccacctc gcaggcattg ccgaccgcat gagcaaggag atcacggccc tggccccag     3780 cgccatgaag atcaaggtgg tggcgccgcc cgagcgcaag tactcggtct ggatcggtgg    3840
ctccatcctc gcctcgctgt ccaccttcca gcaaatgtgg atcgccaagt ccgagtacga    3900
cgagtccggc ccctcgatcg tgcaccggaa gtgcttctaa gcgcttttg cgccaaagcg     3960 cttttgagtg cgccagtagc gcttccaaat gccttcctgc gggcttccgc ccatccaggg    4020
tggtgcggtg tcgcgagggg ccgcggtccg gcgcggcggt gctcgcggct gctgccgcgt    4080
agccggcgac agcgtgctgg gagcggcccg ggcggcttgc ggattgtgtg cgcgctcgga    4140
cccggttttg ggggcgtgtg catacgtgga tagcttgcag taggaggcat agggtttggg    4200
tttgaccgcg cgccggatgc cacgggcgat gattgacgca ggtggcaggc cgaggggtcg    4260
tgtgtgtggc tgtggccacg cacacacccc aattcgttga gtacagcggc gagttgcggc    4320
ggcggcatag cgctggcatg gcgctggatg acgcgctaac gacggaggat gatgatgcag    4380
cgatagaaaa gatatgagga gcgggtcatg gtacatagct tgcgtctgga taggcgtgca    4440
ggtggatgca gggctcttca ttccgcgcca aagcgctggg gtttggggc gggttgacgc     4500 tcgagggagc gcagatctcc cccaccaaaa cctgctcgga ccatttcgtg tgtagcattt    4560
ttacatgaga ggacgcatct gtgactgcag                                    4590
```

<210> SEQ ID NO 32

<211> LENGTH: 1014
<212> TYPE: DNA
<213> ORGANISM: Chlamydomonas reinhardtii

<400> SEQUENCE: 32

```
ttgactcgtt gtgcattcta ggaccccact gctactcaca acaagccaaa atggccgtca      60
tgatgcgcac ccaggcgccc gctgccactc gcgcttcatc gcgcgtcgct gttgccgctc     120
gcccggctgc tcgccgcgcc gtggtggtcc gcgccgaggc tgaggctgcc cctgctgctg     180
ccaagaaggc tgctgagaag cccgcctgga ctgtgccgac cctgaacccc gacactccca     240
gcccgatttt cggtggcagc accggcggtc tgctgcgcaa ggctcagact gaggagttct     300
acgtcatcac ctgggaggct aagaaggagc agatcttcga gatgcccact ggcggtgccg     360
ctatcatgcg ccagggcccc aacctgctga agttcggcaa gaaggagcag tgcctcgccc     420
tgacgaccca gctccgcaac aagttcaagc tgacccctg cttctaccgc gtcttccccg     480
acggcaaggt gcagtacctg caccctgctg acggcgtcta ccccgagaag gtgaacgctg     540
gccgcgtggg cgcgaaccag aacatgcgcc gcatcggcca aacgtcaac cccatcaagg     600
tcaagttctc tggccgcatg atgtcgcctg ctgagatcta agcgttctgg cagcagctgg     660
accgcctgta ccatggagaa gagctttact tgccgggatg gccgatttcg ctgattgata     720
cgggatcgga gctcggaggc tttcgcgcta ggggctaggc gaagggcagt ggtgaccagg     780
gtcggtgtgg ggtcggccca cggtcaatta gccacaggag gatcagggg aggtaggcac      840
gtcgacttgg tttgcgaccc cgcagttttg gcggacgtgc tgttgtagat gttagcgtgt      900
gcgtgagcca gtggccaacg tgccacaccc attgagaaga ccaaccaact tactggcaat     960
atctgccaat gccatactgc atgtaatggc caggccatgt gagagtttgc cgtg          1014
```

<210> SEQ ID NO 33
<211> LENGTH: 1245
<212> TYPE: DNA
<213> ORGANISM: Unknown
<220> FEATURE:
<223> OTHER INFORMATION: Environmental isolate from South Laguna Madre, Texas, USA identified as a member of the genus Tetraselmis.

<400> SEQUENCE: 33

```
atgcaggccg ttatcagcaa gtccgccgcg tccctggccg gagccgtcgt gcccgccaag      60
gccggcgccc tcgcaagtc gatccgcgcg cctgtcgtgt gcgccgccca gccggctagc     120
aaggctgcct ttggccaggc caagagcgta tctgccgtgc gcgatgtgcg tatgtttggc     180
gaggtggaga agacgatcgg tctcgagatt attgaagttg tcgagcaggc agcgatcgcc     240
tcggcccgcc tgatgggcaa aggcgaaaag aatgaagccg atcgcgtcgc agtagaagcg     300
atgcgggtgc ggatgaacca agtggaaatg ctgggccgca tcgtcatcgg tgaaggcgag     360
cgcgacgaag caccgatgct ctatatcggt gaagaagtgg gcatctaccg cgatgcagac     420
aagcgggctg gcgtaccggc tggcaagctg gtggaaatcg acatcgccgt tgaccctgc      480
gaaggcacca acctctgcgc ctacggtcag cccggctcga tggcagtttt ggccatctcc     540
gagaaaggcg gcctgtttgc agctcccgac ttctacatga agaaactggc tgcaccccca     600
gctgccaaag gcaaagtaga catcaataag tccgcgaccg aaaacctgaa aattctctcg     660
gaatgtctcg atcgcgccat cgatgaattg gtggtcgtgg tcatggatcg tccccgccac     720
aaagagctaa tccaagagat ccgccaagcg ggtgcccgcg tccgtctgat cagcgatggt     780
gacgtttcgg ccgcgatctc ctgcggtttt gctggcacca acacccacgc cctgatgggc     840
```

```
atcggtgcag ctcccgaggg tgtgatttcg gcagcagcaa tgcgttgcct cggcggtcac    900
ttccaaggcc agctgatcta cgacccagaa gtggtcaaaa ccggcctgat cggtgaaagc    960
cgtgagagca acatcgctcg cctgcaagaa atgggcatca ccgatcccga tcgcgtctac   1020
gacgccaacg aactggcttc gggtcaagaa gtgctgtttg cggcttgcgg tatcaccccg   1080
ggcttgctga tggaaggcgt gcgcttcttc aaaggcggcg ctcgcaccca gagcttggtg   1140
atctccagcc agtcacggac ggctcgcttc gttgacaccg ttcacatgtt cgacgatgtc   1200
aaaacggtta gcctccgtga ctacaaggac gacgatgaca agtaa                  1245
```

<210> SEQ ID NO 34
<211> LENGTH: 400
<212> TYPE: PRT
<213> ORGANISM: Unknown
<220> FEATURE:
<223> OTHER INFORMATION: Environmental isolate from South Laguna Madre, Texas, USA identified as a member of the genus Tetraselmis.

<400> SEQUENCE: 34

```
Met Gln Ala Val Ile Ser Lys Ser Ala Ala Ser Leu Ala Gly Ala Val
1               5                   10                  15

Val Pro Ala Lys Ala Gly Ala Ala Arg Lys Ser Ile Arg Ala Pro Val
            20                  25                  30

Val Cys Ala Ala Gln Pro Ala Ser Lys Ala Ala Phe Gly Gln Ala Lys
        35                  40                  45

Ser Val Ser Ala Val Arg Asp Val Arg Met Phe Gly Glu Tyr Gly Ala
    50                  55                  60

Ser Gly Thr Ser Phe Tyr Thr Thr Thr Glu Lys Gln Asp Lys Tyr Asp
65                  70                  75                  80

Asp Leu Asp Thr Val Leu Asn Ser Lys Cys Ser Asp Pro Met Ile Arg
                85                  90                  95

Asp Val Ile Lys Glu Met Leu Asp Ala Cys Ala Asp Ile Thr Glu Ala
            100                 105                 110

Leu Arg Ser Ala Leu Val Thr Val Glu Gly Ser Ser Asn Thr Phe Gly
        115                 120                 125

Asp Ala Gln Leu Ser Val Asp Val Ile Ala Asp Asn Ile Met Trp Glu
    130                 135                 140

Ala Cys Lys Asn Ser Lys Val Ile Ala Tyr Gly Ala Ser Glu Glu Glu
145                 150                 155                 160

Pro Glu Val Lys Pro Cys Asn Pro Asn Gly Glu Tyr Thr Val Cys Trp
                165                 170                 175

Asp Pro Leu Asp Gly Ser Ser Ile Val Asp Asn Asn Trp Ala Val Gly
            180                 185                 190

Thr Met Val Gly Ile Trp Gly Ser Lys Ser Gly Thr Gly Ala Asp Gly
        195                 200                 205

Leu Leu Gly Ala Thr Gly Arg Asp Gln Val Thr Ser Leu Val Ala Leu
    210                 215                 220

Tyr Gly Pro Arg Thr Thr Val Leu Val Cys Leu Asp Asp Gly Val Tyr
225                 230                 235                 240

Glu Phe Ser Tyr Gly Cys Thr Pro Glu Gly Cys Gln Leu Ser Asp Gly
                245                 250                 255

Thr Phe Ala Pro Trp Ile Cys Ser Arg Phe Asp Ile Lys Ile Ser Pro
            260                 265                 270

Asp Cys Lys Ile Phe Ser Pro Ala Asn Met Arg Ala Ser Lys Glu Val
        275                 280                 285
```

```
Glu Gly Tyr Lys Lys Leu Leu Asp His Tyr Met Asp Asn Lys Phe Thr
    290                 295                 300
Leu Arg Tyr Thr Gly Gly Leu Val Pro Asp Val Tyr Gln Gln Phe Thr
305                 310                 315                 320
Lys Gly Gln Gly Val Phe Ser Asn Pro Thr Ser Glu Ser Ser Pro Ala
                325                 330                 335
Lys Leu Arg Leu Ala Phe Glu Ala Ala Pro Phe Gly Leu Leu Val Glu
                340                 345                 350
Lys Ala Gly Gly Lys Thr Ser Asp Gly Val Thr Gly Ser Val Leu
                355                 360                 365
Asp Val Pro Ile Thr Ala Val Asp Gln Arg Thr Ala Leu Cys Ile Gly
    370                 375                 380
Ser Ser Asn Glu Val Asp Arg Phe Asn Glu Met Ile Cys Leu Ile Lys
385                 390                 395                 400

<210> SEQ ID NO 35
<211> LENGTH: 183
<212> TYPE: DNA
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 35
atgcaggccg ttatcagcaa gtccgccgcg tccctggccg gagccgtcgt gcccgccaag      60
gccggcgccg ctcgcaagtc gatccgcgcg cctgtcgtgt gcgccgccca gccggctagc     120
aaggctgcct tggccaggc caagagcgta tctgccgtgc gcgatgtgcg tatgtttggc     180
gag                                                                  183

<210> SEQ ID NO 36
<211> LENGTH: 61
<212> TYPE: PRT
<213> ORGANISM: Unknown
<220> FEATURE:
<223> OTHER INFORMATION: Environmental isolate from South Laguna Madre,
      Texas, USA identified as a member of the genus Tetraselmis.

<400> SEQUENCE: 36

Met Gln Ala Val Ile Ser Lys Ser Ala Ala Ser Leu Ala Gly Ala Val
1               5                   10                  15
Val Pro Ala Lys Ala Gly Ala Ala Arg Lys Ser Ile Arg Ala Pro Val
                20                  25                  30
Val Cys Ala Ala Gln Pro Ala Ser Lys Ala Ala Phe Gly Gln Ala Lys
            35                  40                  45
Ser Val Ser Ala Val Arg Asp Val Arg Met Phe Gly Glu
    50                  55                  60
```

TETRASELMIS PROMOTERS AND TERMINATORS FOR USE IN EUKARYOTIC CELLS

REFERENCE TO A SEQUENCE LISTING

This application contains references to amino acid sequences and/or nucleic acid sequences which have been submitted concurrently herewith as the sequence listing text file "16244-000018-US.txt", file size 38 kilobytes (kb), created on 3 Dec. 2012. The aforementioned sequence listing is hereby incorporated by reference in its entirety pursuant to 37 C.F.R. §1.52(e)(iii)(5).

FIELD

The present invention relates to gene regulatory elements for use in heterologous gene expression in eukaryotic cells, particularly algal cells.

BACKGROUND

Algal cells are a promising source of biofuels (Wijffels & Barbosa (2010) Science 329:796-99). Their ability to harness solar energy to convert carbon dioxide into carbon-rich lipids already exceeds the abilities of oil-producing agricultural crops, with the added advantage that algae grown for biofuel do not compete with oil-producing crops for agricultural land (Wijffels & Barbosa, 2010). Tetraselmis phytoplankton are unicellular marine green algae that can be cultured easily, rapidly, and economically. In order to maximize algal fuel production, new algal strains will need to be engineered for growth and carbon fixation at an industrial scale (Wijffels & Barbosa, 2010).

Modern recombinant strain development requires robust and efficient tools for expressing transgenes to alter cellular metabolism and physiology in desired ways. An essential component of any "toolkit" is a suite of functional promoter elements to drive transgene-expression. As such, there is a need for endogenous promoters, cloned and verified, from the strains for which recombinant DNA technology is being developed. There is a comparative lack of knowledge relating to techniques suitable for transforming Tetraselmis cells with transgenes, particularly of constitutive promoters and terminators derived from Tetraselmis species.

Transformation of Tetraselmis subcordiformis by glass bead treatment of protoplasts has been reported. See Cui et al. (2010) World J. Microbiol. Biotechnol. 26:1653-57. However, this method demonstrated only transient detection of the transformed gene—a green fluorescent protein controlled by a cytomegalovirus promoter—and did not make use of a selectable marker.

Further, while it will be necessary to manipulate the Tetraselmis genome in order to maximize biofuel output, this has proven difficult to date because of the thick cell wall that surrounds Tetraselmis cells. Better procedures for genetic manipulation of these organisms are urgently needed.

SUMMARY

This section provides a general summary of the disclosure, and is not a comprehensive disclosure of its full scope or all of its features.

Stable expression of genes, e.g. heterologous genes, requires the use of gene regulatory elements such as promoters and terminators. Novel promoters and terminators for use in driving gene expression in eukaryotic species such as but not limited to heterokont, fungal, and microalgal species, including Tetraselmis, are provided herein. Transformed heterokont, fungal, or algal cells can be used, for example, for synthesis of various products including lipids. In one aspect, an isolated DNA molecule is provided in which the isolated DNA molecule comprises a sequence selected from the group consisting of a nucleotide sequence having at least 80% identity to at least 100 contiguous nucleotides of SEQ ID NO:1; a nucleotide sequence having at least 80% identity to at least 100 contiguous nucleotides of SEQ ID NO:2; a nucleotide sequence having at least 80% identity to at least 100 contiguous nucleotides of SEQ ID NO:3; a nucleotide sequence having at least 80% identity to at least 100 contiguous nucleotides of SEQ ID NO:4; a nucleotide sequence having at least 80% identity to at least 100 contiguous nucleotides of SEQ ID NO:5; a nucleotide sequence having at least 80% identity to at least 100 contiguous nucleotides of SEQ ID NO:6; a nucleotide sequence having at least 80% identity to at least 100 contiguous nucleotides of SEQ ID NO:7; or a nucleotide sequence having at least 80% identity to at least 100 contiguous nucleotides of SEQ ID NO:8. Additionally, the isolated DNA molecule having at least 80% identity to at least 100 contiguous nucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 can have promoter activity in a eukaryotic cell.

For example, an isolated DNA molecule as provided herein can include any or any combination of: a nucleic acid sequence that has at least 85% or at least 90% nucleotide sequence identity to at least 100 contiguous nucleotides of SEQ ID NO:1, a nucleic acid sequence that has at least 85% or at least 90% nucleotide sequence identity to at least 100 contiguous nucleotides of SEQ ID NO:2, a nucleic acid sequence that has at least 85% or at least 90% nucleotide sequence identity to at least 100 contiguous nucleotides of SEQ ID NO:3, a nucleic acid sequence that has at least 85% or at least 90% nucleotide sequence identity to at least 100 contiguous nucleotides of SEQ ID NO:4, a nucleic acid sequence that has at least 85% or at least 90% nucleotide sequence identity to at least 100 contiguous nucleotides of SEQ ID NO:5, a nucleic acid sequence that has at least 85% or at least 90% nucleotide sequence identity to at least 100 contiguous nucleotides of SEQ ID NO:6, a nucleic acid sequence that has at least 85% or at least 90% nucleotide sequence identity to at least 100 contiguous nucleotides of SEQ ID NO:7, a nucleic acid sequence that has at least 85% or at least 90% nucleotide sequence identity to at least 100 contiguous nucleotides of SEQ ID NO:8. The isolated DNA molecule having at least 85% or at least 90% identity to at least 100 contiguous nucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 can have promoter activity, for example, in an algal, fungal, or heterokont cell.

In some examples, an isolated DNA molecule is provided where the isolated DNA molecule includes a nucleic acid sequence that has at least 95% identity to at least 100 contiguous nucleotides of SEQ ID NO:1, a nucleic acid sequence that has at least 95% nucleotide sequence identity to at least 100 contiguous nucleotides of SEQ ID NO:2, a nucleic acid sequence that has at least 95% nucleotide sequence identity to at least 100 contiguous nucleotides of SEQ ID NO:3, a nucleic acid sequence that has at least 95% nucleotide sequence identity to at least 100 contiguous nucleotides of SEQ ID NO:4, a nucleic acid sequence that has at least 95% nucleotide sequence identity to at least 100 contiguous nucleotides of SEQ ID NO:5, a nucleic acid sequence that has at least 95% nucleotide sequence identity to at least 100 contiguous nucleotides of SEQ ID NO:6, a nucleic acid sequence that has at least 95% nucleotide sequence identity to at least 100 contiguous nucleotides of SEQ ID NO:7, or a nucleic acid sequence that has at least 95% nucleotide sequence identity to at least 100 contiguous nucleotides of SEQ ID NO:8. The DNA molecule can have promoter activity, for example, in an algal, fungal, or heterokont cell.

In some examples an isolated DNA molecule as provided herein can be selected from the group consisting of: an isolated DNA molecule that comprises a nucleotide sequence comprising at least 100 contiguous nucleotides of SEQ ID NO:1; an isolated DNA molecule that comprises a nucleotide sequence comprising at least 100 contiguous nucleotides of SEQ ID NO:2; an isolated DNA molecule that comprises a nucleotide sequence comprising at least 100 contiguous nucleotides of SEQ ID NO:3; an isolated DNA molecule that comprises a nucleotide sequence comprising at least 100 contiguous nucleotides of SEQ ID NO:4; an isolated DNA molecule that comprises a nucleotide sequence comprising at least 100 contiguous nucleotides of SEQ ID NO:5; an isolated DNA molecule that comprises a nucleotide sequence comprising at least 100 contiguous nucleotides of SEQ ID NO:6; an isolated DNA molecule that comprises a nucleotide sequence comprising at least 100 contiguous nucleotides of SEQ ID NO:7; and an isolated DNA molecule that comprises a nucleotide sequence comprising at least 100 contiguous nucleotides of SEQ ID NO:8. The DNA molecule can have promoter activity in a eukaryotic cell, for example, in an algal, fungal, or heterokont cell.

For example, an isolated DNA molecule as provided herein can comprise a nucleotide sequence having at least 80%, at least 85%, at least 90%, or at least 95% sequence identity to at least 100, at least 200, at least 300, at least 400, or at least 500 contiguous nucleotides of SEQ ID NO:1; a nucleotide sequence having at least 80%, at least 85%, at least 90%, or at least 95% sequence identity to at least 100, at least 200, at least 300, at least 400, or at least 500 contiguous nucleotides of SEQ ID NO:2; a nucleotide sequence having at least 80%, at least 85%, at least 90%, or at least 95% sequence identity to at least 100, at least 200, at least 300, at least 400, or at least 500 contiguous nucleotides of SEQ ID NO:3; a nucleotide sequence having at least 80%, at least 85%, at least 90%, or at least 95% sequence identity to at least 100, at least 200, at least 300, at least 400, or at least 500 contiguous nucleotides of SEQ ID NO:4; a nucleotide sequence having at least 80%, at least 85%, at least 90%, or at least 95% sequence identity to at least 100, at least 200, at least 300, at least 400, or at least 500 contiguous nucleotides of SEQ ID NO:5; a nucleotide sequence having at least 80%, at least 85%, at least 90%, or at least 95% sequence identity to at least 100, at least 200, at least 300, at least 400, or at least 500 contiguous nucleotides of SEQ ID NO:6; a nucleotide sequence having at least 80%, at least 85%, at least 90%, or at least 95% sequence identity to at least 100, at least 200, at least 300, at least 400, or at least 500 contiguous nucleotides of SEQ ID NO:7; or a nucleotide sequence having at least 80%, at least 85%, at least 90%, or at least 95% sequence identity to at least 100, at least 200, at least 300, at least 400, or at least 500 contiguous nucleotides of SEQ ID NO:8. The DNA molecule can have promoter activity in a eukaryotic cell, for example, in an algal, fungal, or heterokont cell.

In further examples provided herein is an isolated DNA molecule comprising a nucleotide sequence having at least 80%, at least 85%, at least 90%, or at least 95% sequence identity to SEQ ID NO:1; a nucleotide sequence having at least 80%, at least 85%, at least 90%, or at least 95% sequence identity to SEQ ID NO:2; a nucleotide sequence having at least 80%, at least 85%, at least 90%, or at least 95% sequence identity to SEQ ID NO:3; a nucleotide sequence having at least 80%, at least 85%, at least 90%, or at least 95% sequence identity to SEQ ID NO:4; a nucleotide sequence having at least 80%, at least 85%, at least 90%, or at least 95% sequence identity to SEQ ID NO:5; a nucleotide sequence having at least 80%, at least 85%, at least 90%, or at least 95% sequence identity to SEQ ID NO:6; a nucleotide sequence having at least 80%, at least 85%, at least 90%, or at least 95% sequence identity to SEQ ID NO:7; or a nucleotide sequence having at least 80%, at least 85%, at least 90%, or at least 95% sequence identity to SEQ ID NO:8. An isolated DNA molecule as disclosed herein can find use, for example, as a sequence that when operably linked to a nucleic acid sequence that encodes a polypeptide or that can be transcribed into a functional RNA can affect expression of the nucleic acid sequence encoding a polypeptide or functional RNA.

Also provided herein is a promoter comprising a nucleic acid sequence having at least 80% identity to at least 100, at least 200, at least 300, at least 400, or at least 500 contiguous nucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8. For example, a promoter as provided herein can comprise a nucleic acid sequence having at least 85% or at least 90% sequence identity to at least 100, at least 200, at least 300, at least 400, or at least 500 contiguous nucleotides of SEQ ID NO:1, at least 100, at least 200, at least 300, at least 400, or at least 500 contiguous nucleotides of SEQ ID NO:2, at least 100, at least 200, at least 300, at least 400, or at least 500 contiguous nucleotides of SEQ ID NO:3, at least 100, at least 200, at least 300, at least 400, or at least 500 contiguous nucleotides of SEQ ID NO:4, at least 100, at least 200, at least 300, at least 400, or at least 500 contiguous nucleotides of SEQ ID NO:5, at least 100, at least 200, at least 300, at least 400, or at least 500 contiguous nucleotides of SEQ ID NO:6, at least 100, at least 200, at least 300, at least 400, or at least 500 contiguous nucleotides of SEQ ID NO:7, or at least 100, at least 200, at least 300, at least 400, or at least 500 contiguous nucleotides of SEQ ID NO:8.

In some examples, a promoter can comprise a sequence having at least 95% identity to at least 100, at least 200, at least 300, at least 400, or at least 500 contiguous nucleotides of SEQ ID NO:1, at least 100, at least 200, at least 300, at least 400, or at least 500 contiguous nucleotides of SEQ ID NO:2, at least 100, at least 200, at least 300, at least 400, or at least 500 contiguous nucleotides of SEQ ID NO:3, at least 100, at least 200, at least 300, at least 400, or at least 500 contiguous nucleotides of SEQ ID NO:4, at least 100, at least 200, at least 300, at least 400, or at least 500 contiguous nucleotides of SEQ ID NO:5, at least 100, at least 200, at least 300, at least 400, or at least 500 contiguous nucleotides of SEQ ID NO:6, at least 100, at least 200, at least 300, at least 400, or at least 500 contiguous nucleotides of SEQ ID NO:7, or at least 100, at least 200, at least 300, at least 400, or at least 500 contiguous nucleotides of SEQ ID NO:8. In various examples, a promoter as provided herein can comprise at least 100, at least 200, at least 300, at least 400, or at least 500 contiguous nucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 In additional examples, a promoter as provided herein can be selected from the group consisting of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

A promoter as provided herein can be a constitutive promoter, and may be active in a host cell cultured under conditions in which one or more nutrients are deficient as well as in culture conditions in which nutrients are sufficient for proliferation and/or growth of the culture. For example, a promoter provided herein may mediate transcriptions of an operably linked nucleic acid sequence in nitrogen replete as well as in nitrogen deficient conditions.

Also provided is an isolated DNA molecule comprising a sequence selected from the group consisting of a nucleotide sequence having at least 80% identity to at least 100 contiguous nucleotides of SEQ ID NO:9 or a nucleotide sequence having at least 80% identity to at least 100 contiguous nucleotides of SEQ ID NO:10. The isolated DNA molecule can have terminator activity. For example, an isolated DNA molecule can comprise a nucleotide sequence having at least 85% or at least 90% to at least 100 contiguous nucleotides of SEQ ID NO:9 or SEQ ID NO:10. In some examples, an isolated DNA molecule can comprise a sequence having at least 95% to at least 100 contiguous nucleotides of SEQ ID NO:9 or SEQ ID NO:10. For example, an isolated DNA molecule as provided herein can comprise a nucleotide sequence having at least 80%, at least 85%, or at least 90% identity to at least 100, at least 200, at least 300, at least 400, or at least 500 contiguous nucleotides of SEQ ID NO:9 or SEQ ID NO:10. For example, an isolated DNA molecule as provided herein can be selected from the group consisting of: an isolated DNA molecule comprising a nucleotide sequence having at least 95% identity to at least 100, at least 200, at least 300, at least 400, or at least 500 contiguous nucleotides of SEQ ID NO:9 and an isolated DNA molecule comprising a nucleotide sequence having at least 95% identity to at least 100, at least 200, at least 300, or at least 400 contiguous nucleotides of SEQ ID NO:10. For example, an isolated DNA molecule as provided herein can be selected from the group consisting of: an isolated DNA molecule comprising at least 100, at least 200, at least 300, at least 400, or at least 500 contiguous nucleotides of SEQ ID NO:9 and an isolated DNA molecule comprising at least 100, at least 200, at least 300, or at least 400 contiguous nucleotides of SEQ ID NO:10. The isolated DNA molecule can comprise a terminator. The DNA molecule can find use, for example, as a sequence that when operably linked to a nucleic acid sequence that encodes a polypeptide or that can be transcribed into a functional RNA can affect expression of the nucleic acid sequence encoding a polypeptide or functional RNA.

Also provided herein is an expression cassette. The expression cassette comprises a promoter as disclosed herein and a heterologous gene operably linked to the promoter. The gene can encode, for example, a polypeptide or a functional RNA. The expression cassette can further optionally comprise a nucleic acid sequence comprising a terminator sequence, such as but not limited to, any disclosed herein. In various examples, the expression cassette can include a heterologous gene that encodes (a) a protein associated with lipid biosynthesis, (b) a protein having lipolytic activity, (c) a protein that participates in photosynthesis, (d) a protein associated with carbon fixation, (e) a transporter protein, (f) a dehydrogenase, (g) a transcription factor, (h) a protein involved in cell signaling, or (i) a functional RNA. A functional RNA can be, for example, an antisense sequence, a micro RNA, a shRNA, or a ribozyme. The expression cassette can be provided in a vector, e.g., an expression vector, which can optionally include one or more of an origin of replication, sequences mediating recombination into a host genome, or a selectable marker.

Also provided herein is an expression cassette that includes a promoter as provided herein operably linked to a selectable marker gene or reporter gene. For example, an expression cassette can include a promoter as disclosed herein operably linked to a gene encoding an antibiotic-resistance-conferring protein and in particular nonlimiting examples can comprise any of SEQ ID NOs:1-8.

Also provided herein is a vector for eukaryotic cell transformation that comprises an expression cassette as disclosed herein. Additionally, a vector herein can include any promoter disclosed herein operably linked to a selectable marker gene or reporter gene. The transformation or expression vector can further include a terminator, such as but not limited to any disclosed herein, operably linked to the selectable marker or reporter gene. The gene encoding a selectable marker can be a gene encoding a polypeptide that confers resistance to an antibiotic, a polypeptide that confers tolerance to an herbicide, a gene encoding an auxotrophic marker, or any other gene product that can allow for selection of transformants. A gene encoding a reporter protein can, for example, encode a fluorescent protein or an enzyme that can produce a detectable product.

Also provided herein is a method for transforming a eukaryotic cell. The method comprises introducing a transformation or expression vector that includes a promoter as provided herein operably linked to a heterologous gene, a selectable marker, and/or a reporter gene; and selecting for a transformant. For example, the eukaryotic cell can be transformed by means of a biolistic procedure. The eukaryotic cell can be selected from the group consisting of fungi, heterokonts, algae, and plants, and in a particular embodiment is an algal cell.

Also provided herein is a method for co-transforming a eukaryotic cell. The method comprises introducing both a transformation or expression vector that includes a promoter as provided herein operably linked to a nucleic acid sequence encoding a selectable marker protein, and further includes a nucleic acid sequence encoding a polypeptide of interest, and selecting for a transformant. The nucleic acid sequence encoding a polypeptide of interest can encode any polypeptide, including, without limitation, a second selectable marker, a reporter protein, an enzyme, a structural protein, a transcriptional regulator, a transporter, etc. The nucleic acid sequence encoding a polypeptide can also optionally be linked to a promoter, such as but not limited to a promoter as disclosed herein. The eukaryotic cell can be co-transformed, for example, by means of a biolistic procedure, by electroporation, by the use of agrobacteria or other biological vectors, etc. The eukaryotic cell can be selected from the group consisting of fungi, heterokonts, algae, and plants, and in a particular embodiment is an algal cell.

For example, an algal cell that can be transformed or co-transformed with a vector as provided herein can be selected from the group consisting of species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamy-* della, *Skeletonema, Spyrogyra, Stichococcus, Tetrachlorella, Tetraselmis, Thalassiosira, Tribonema, Vaucheria, Viridiella, Vischeria*, and *Volvox*. In one example, the algal cell can be of the Chlorophyceae class, such as a species of *Chlamydomonas, Dunaliella, Hematococcus*, or *Scenedesmus*. In other examples, the algal cell can be of the Trebouxiophyceae class, such as a species of *Chlorella, Pseudochlorella*, or *Nannochloris*, for example. In some examples, the algal cell can be an algal species of the Prasinophyceae class, for example, an *Ostreococcus* or a *Tetraselmis* cell.

Also provided herein is a eukaryotic host cell transformed with an expression vector or transformation vector as provided herein. The eukaryotic host cell can be a microorganism such as a microalga, such as but not limited to for example, a *Tetraselmis* cell.

In a further aspect, provided herein is a nucleic acid molecule that comprises a nucleotide sequence encoding a chloroplast transit peptide. The chloroplast transit peptide can direct a polypeptide to which it is operably linked to the stroma of a chloroplast, such as the chloroplast of a microalga. Provided herein is a nucleic acid molecule that comprises a nucleotide sequence encoding a chloroplast transit peptide having at least 80%, at least 85%, at least 90%, or at least 95% sequence identity to SEQ ID NO:36 or a functional fragment thereof. The nucleotide sequence encoding a chloroplast transit peptide as provided herein can be operably linked to a polypeptide-encoding nucleotide sequence such that on expression of the chloroplast transit peptide-polypeptide construct, the synthesized polypeptide is localized to the chloroplast of a eukaryotic photosynthetic organism, such as an algal chloroplast. Further provided is a nucleic acid molecule that comprises a nucleotide sequence encoding a chloroplast transit peptide having at least 80%, at least 85%, at least 90%, or at least 95% sequence identity to SEQ ID NO:36, operably linked to a nucleotide sequence encoding a polypeptide of interest.

In a related aspect, provided herein is a method for directing a polypeptide of interest to the chloroplast of a eukaryotic photosynthetic organism. The method includes transforming a cell of a eukaryotic photosynthetic organism with a construct that includes a nucleotide sequence encoding a chloroplast transit peptide having at least 80%, at least 85%, at least 90%, or at least 95% sequence identity to SEQ ID NO:36 operably linked to a nucleotide sequence encoding a polypeptide of interest, and providing conditions under which the construct is expressed, whereby the polypeptide of interest is directed to the chloroplast of the of eukaryotic photosynthetic organism. The eukaryotic photosynthetic organism can be a plant or alga, and in a particular example is a microalga, such as any provided herein, and may be, for example, a microalga of the Chlorophyte phylum. The microalga can be, for example, a microalga of the class Chlorophyceae, Trebouxiophyceae, or Prasinophyceae, and in some examples is a *Tetraselmis* species.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, not all possible implementations, and are not intended to limit the scope of the present disclosure.

DETAILED DESCRIPTION

A. Definitions

Figure 1:
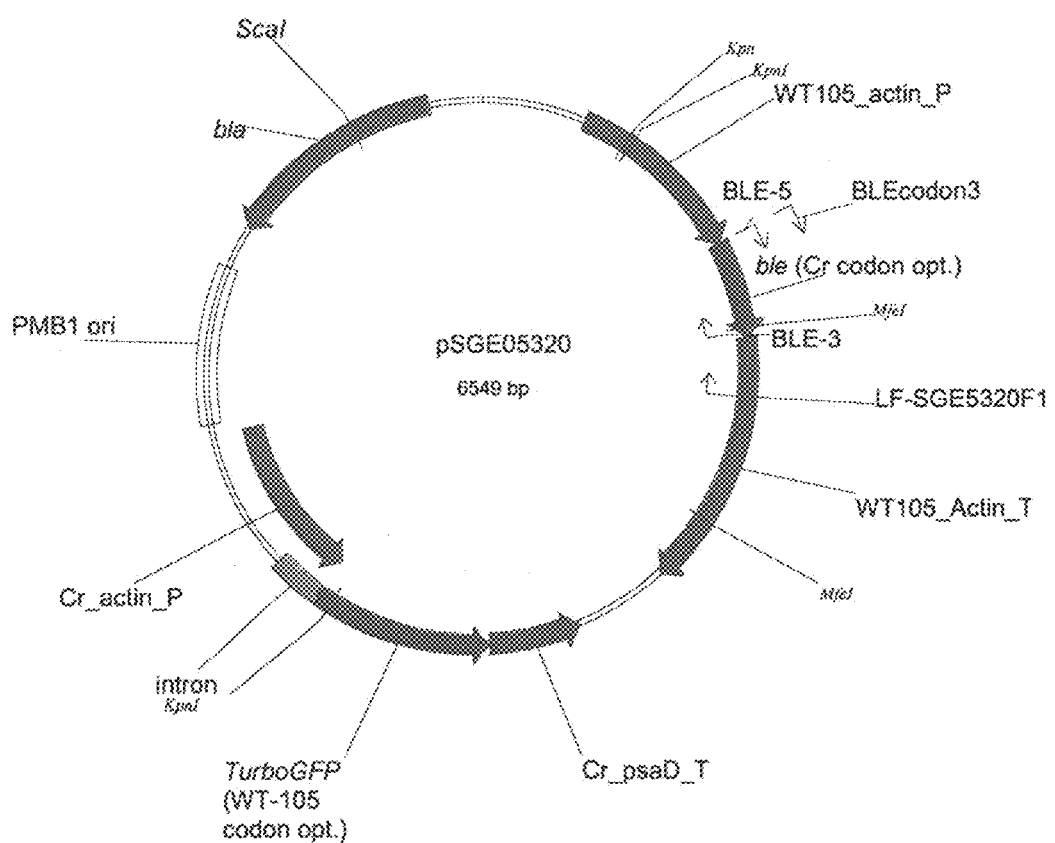
FIG. 1 is a plasmid map for p05320.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B", "A or B", "A", and "B".

The terms, "cells", "cell cultures", "cell line", "recombinant host cells", "recipient cells" and "host cells" as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

The term "gene" is used broadly to refer to any segment of nucleic acid molecule (typically DNA, but optionally RNA) that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be e.g., sequences that are not transcribed or translated. Genes can be obtained from a variety of sources, including cloning from a source of interest or synthesizing from known or predicted sequence information, and may include sequences designed to have desired parameters.

The term "nucleic acid" or "nucleic acid molecule" refers to, e.g., DNA or RNA (e.g., mRNA). The nucleic acid molecules can be double-stranded or single-stranded; single stranded RNA or DNA can be the coding (sense) strand or the non-coding (antisense) strand.

The terms "coding sequence" or "coding region" as used herein, refer to a region of a DNA sequence that can be transcribed to produce an mRNA transcript that can be translated into an amino acid sequence, e.g., of a peptide or polypeptide, or an RNA transcript that can be translated into an amino acid sequence, e.g., of a peptide or a polypeptide. The term "non-coding sequence" or "non-coding region" refers to (1) a region of a DNA sequence that, if transcribed, is not translated into an amino acid sequence (e.g., introns, untranslated regions, etc.); or (2) a region of an RNA sequence that is not translated into amino acids. For simplicity and brevity, a sequence that "encodes a polypeptide" refers to a DNA sequence that can be transcribed and translated to produce the polypeptide or an RNA sequence that can be translated to produce the polypeptide, whereas a sequence that "encodes a functional RNA" refers to a DNA sequence that when transcribed produces a functional RNA molecule. An RNA molecule that encodes a polypeptide or functional RNA can be further processed prior to, or concommittant with, translation into a polypeptide or formation of the mature functional RNA.

A "functional RNA molecule" is an RNA molecule that can interact with one or more proteins or nucleic acid molecules to perform or participate in a structural, catalytic, or regulatory function that affects the expression or activity of a gene or gene product other than the gene that produced the functional RNA. A functional RNA can be, for example, a transfer RNA (tRNA), ribosomal RNA (rRNA), anti-sense RNA (as-RNA), microRNA (miRNA), short-hairpin RNA (shRNA), small interfering RNA (siRNA), small nucleolar RNAs (snoRNAs), piwi-interacting RNA (piRNA), or a ribozyme.

A nucleic acid may be "derived from" an indicated source, which includes the isolation (in whole or in part) of a nucleic acid segment from an indicated source or the purification of a polypeptide from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can incur one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis. A gene or nucleic acid molecule that is derived from a referenced gene or nucleic acid molecule that encodes a functional RNA or polypeptide can encode a functional RNA or polypeptide having at least 70%, at least 75%, at least 80%, at least 85%, at least 90%, at least 95%, at least 96%, at least 97%, at least 98%, or at least 99% sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

The term "isolated" nucleic acid, such as an isolated protein or nucleic acid as used herein, refers to a biomolecule removed from the context in which the biomolecule exists in nature. An isolated biomolecule can be, in some instances, partially or substantially purified. For example, an isolated nucleic acid molecule can be a nucleic acid sequence that has been excised from the chromosome, genome, or episome into which it is integrated in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

The terms "naturally-occurring" and "wild-type" (WT) refer to a form found in nature. For example, a naturally occurring or wild-type nucleic acid molecule, nucleotide sequence, or protein may be present in, and isolated from, a natural source, and is not intentionally modified by human manipulation.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

Further, the term "exogenous" as used herein in the context of a gene or protein, refers to a gene or protein that is not derived from the host organism species.

The term "transgene" as used herein, refers to an exogenous gene, that is, a gene introduced into a microorganism or a progenitor by human intervention.

The term "ortholog" of a gene or protein as used herein refers to its functional equivalent in another species.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

The term "heterologous" when used in reference to a polynucleotide, a gene, a nucleic acid, a polypeptide, or an enzyme refers to a polynucleotide, gene, a nucleic acid, polypeptide, or an enzyme not derived from the host species. For example, "heterologous gene" or "heterologous nucleic acid sequence" as used herein, refers to a gene or nucleic acid sequence from a different species than the species of the host organism it is introduced into. When referring to a gene regulatory sequence or to an auxiliary nucleic acid sequence used for maintaining or manipulating a gene sequence (e.g. a 5' untranslated region, 3' untranslated region, poly A addition sequence, intron sequence, splice site, ribosome binding site, internal ribosome entry sequence, genome homology region, recombination site, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked. Similarly, when referring to a protein localization sequence or protein domain of an engineered protein, "heterologous" means that the localization sequence or protein domain is derived from a protein different from that into which it is incorporated by genetic engineering.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering. The terms "peptide," "polypeptide" and "protein" are used interchangeably herein, although "peptide" may be used to refer to a polypeptide having no more than about 100 amino acids, or no more than about 60 amino acids. The nucleic acid sequences according to some embodiments of the present invention encode cyanobacterial transcription factor domain proteins.

When applied to organisms, the terms "transgenic" or "recombinant" or "engineered" or "genetically engineered" refer to organisms that have been manipulated by introduction of an exogenous or recombinant nucleic acid sequence into the organism. Non-limiting examples of such manipulations include gene knockouts, targeted mutations and gene replacement, promoter replacement, deletion, or insertion, as well as introduction of transgenes into the organism. For example, a transgenic microorganism can include an introduced exogenous regulatory sequence operably linked to an endogenous gene of the transgenic microorganism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

The term "expression cassette" as used herein, refers to a nucleic acid construct that encodes a protein or functional RNA (e.g. a tRNA, a short hairpin RNA, one or more microRNAs, a ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

"Regulatory sequence", "regulatory element", or "regulatory element sequence" refers to a nucleotide sequence located upstream (5'), within, or downstream (3') of a coding sequence or functional RNA-encoding sequence. Transcription of the coding sequence or functional RNA-encoding sequence and/or translation of an RNA molecule resulting from transcription of the coding sequence are typically affected by the presence or absence of the regulatory sequence. These regulatory element sequences may comprise promoters, cis-elements, enhancers, terminators, or introns. Regulatory elements may be isolated or identified from UnTranslated Regions (UTRs) from a particular polynucleotide sequence. Any of the regulatory elements described herein may be present in a chimeric or hybrid regulatory expression element. Any of the regulatory elements described herein may be present in a recombinant construct of the present invention.

The terms "promoter", "promoter region", or "promoter sequence" refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked transcribable polynucleotide molecule, e.g., a coding sequence or functional RNA sequence. Promoters may contain, in addition to sequences recognized by RNA polymerase and, preferably, other transcription factors, regulatory sequence elements such as cis-elements or enhancer domains that affect the transcription of operably linked genes. An "algal promoter" is a native or non-native promoter that is functional in algal cells.

The term "constitutive" promoter as used herein, refers to a promoter that is active under most environmental and developmental conditions. A constitutive promoter is active regardless of external environment, such as light and culture medium composition. In some examples, a constitutive promoter is active in the presence and in the absence of a nutrient. For example, a constitutive promoter may be a promoter that is active (mediates transcription of a gene to which it is operably-linked) under conditions of nitrogen depletion as well as under conditions in which nitrogen is not limiting (nitrogen replete conditions). In contrast, an "inducible" promoter is a promoter that is active in response to particular environmental conditions, such as the presence or absence of a nutrient or regulator, the presence of light, etc.

The term "operably linked," as used herein, denotes a configuration in which a control sequence or localization sequence is placed at an appropriate position relative to a sequence that encodes a polypeptide or functional RNA such that the control sequence directs or regulates the expression or localization of the mRNA encoding the polypeptide, the polypeptide, and/or the functional RNA). Thus, a promoter is in operable linkage with a nucleic acid sequence if it can mediate transcription of the nucleic acid sequence. When introduced into a host cell, an expression cassette that includes a control sequence can result in transcription of the gene to which it is operably linked and/or translation of an encoded RNA or polypeptide under appropriate conditions. Antisense or sense constructs that are not or cannot be translated are not excluded by this definition. In the case of both expression of transgenes and suppression of endogenous genes (e.g., by antisense, or sense suppression) one of ordinary skill will recognize that the inserted polynucleotide sequence need not be identical, but may be only substantially identical to a sequence of the gene from which it was derived. As explained herein, these substantially identical variants are specifically covered by reference to a specific nucleic acid sequence.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, insertional mutation, or meganuclease disruption), or a gene having decreased expression resulting from alteration of gene regulatory sequences. An attenuated gene may also be a gene that is targeted by a "gene knockdown" construct, such as, for example, a construct encoding an antisense RNA, a microRNA, a short hairpin RNA, or a ribozyme. In the case of both expression of transgenes and suppression of endogenous genes (e.g., by antisense or sense suppression) one of ordinary skill will recognize that the inserted polynucleotide sequence need not be identical, but may be only substantially identical to a sequence of the gene from which it was derived. As explained herein, these substantially identical variants are specifically covered by reference to a specific nucleic acid sequence.

The term "photosynthetic organism" as used herein is any prokaryotic or eukaryotic organism that can perform photosynthesis. Photosynthetic organisms include higher plants (i.e., vascular plants), bryophytes, algae, and photosynthetic bacteria. The term "algae" includes, but is not limited to, a species of Bacillariophyceae (diatoms), Bolidomonas, Chlorophyceae (green algae), Chrysophyceae (golden algae), Carophyceae, Cyanophyceae (cyanobacteria), Eustigmatophyceae (pico-plankton), Glaucocystophytes, Pelagophytes, Phaeophyceae (brown algae), Prasinophyceae (pico-plankton), Raphidophytes, Rhodophyceae (red algae), Synurophyceae and Xanthophyceae (yellow-green algae). The term "algae" includes microalgae. The term "microalgae" as used herein refers to microscopic, single-celled algae species including, but not limited to, eukaryotic single-celled algae of the Bacillariophyceae, Chlorophyceae, Prasinophyceae, Trebouxiophyceae, and Eustigmatophyceae classes. The term "photosynthetic bacteria" includes, but is not limited to, cyanobacteria, green sulfur bacteria, purple sulfur bacteria, purple non-sulfur bacteria, and green non-sulfur bacteria.

The term "selectable marker" or "selectable marker gene" as used herein includes any gene that confers a phenotype on a cell in which it is expressed to facilitate the selection of cells that are transfected or transformed with a nucleic acid construct of the invention. The term may also be used to refer to gene products that effectuate said phenotypes. Examples of selectable markers include:

genes conferring resistance to antibiotics such as amikacin (aphA6), ampicillin (amp$^R$), blasticidin (bls, bsr, bsd), bleomicin or phleomycin (ZEOCIN™) (ble), chloramphenicol (cat), emetine (RBS14p or cry1-1), erythromycin (ermE), G418 (GENETICIN™) (neo), gentamycin (aac3 or aacC4), hygromycin B (aphIV, hph, hpt), kanamycin (nptII), methotrexate (DHFR mtx$^R$), penicillin and other β-lactams (β-lactamases), streptomycin or spectinomycin (aadA, spec/strep), and tetracycline (tetA, tetM, tetQ);

genes conferring tolerance to herbicides such as aminotriazole, amitrole, andrimid, aryloxyphenoxy propionates, atrazines, bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, or urea; acetyl CoA carboxylase (ACCase); acetohydroxy acid synthase (ahas); acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (crtI), prenyl transferase, protoporphyrin oxidase, the psbA photosystem II polypeptide (psbA), and SMM esterase (SulE) superoxide dismutase (sod);

genes that may be used in auxotrophic strains or to confer other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

A "reporter gene" is a gene encoding a protein that is detectable or has an activity that produces a detectable product. A reporter gene can encode a visual marker or enzyme that produces a detectable signal, such as cat, lacZ, uidA, xylE, an alkaline phosphatase gene, an α-amylase gene, an α-galactosidase gene, a β-glucuronidase gene, a β-lactamase gene, a horseradish peroxidase gene, a luciferin/luciferase gene, an R-locus gene, a tyrosinase gene, or a gene encoding a fluorescent protein, including but not limited to a blue, cyan, green, red, or yellow fluorescent protein, a photoconvertible, photoswitchable, or optical highlighter fluorescent protein, or any of variant thereof, including, without limitation, codon-optimized, rapidly folding, monomeric, increased stability, and enhanced fluorescence variants.

The term "terminator" or "terminator sequence" or "transcription terminator" as used herein refers to a regulatory section of genetic sequence that causes RNA polymerase to cease transcription.

The term "transformation" as used herein refers to the introduction of one or more exogenous nucleic acid sequences or polynucleotides into a host cell or organism by using one or more physical, chemical, or biological methods. Physical and chemical methods of transformation (i.e., "transfection") include, by way of non-limiting example, electroporation and liposome delivery. Biological methods of transformation (i.e., "transduction") include transfer of DNA using engineered viruses or microbes (e.g., *Agrobacterium*).

The terms, "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window. The degree of amino acid or nucleic acid sequence identity can be determined by various computer programs for aligning the sequences to be compared based on designated program parameters. For example, sequences can be aligned and compared using the local homology algorithm of Smith & Waterman (1981) *Adv. Appl. Math.* 2:482-89, the homology alignment algorithm of Needleman & Wunsch (1970) *J. Mol. Biol.* 48:443-53, or the search for similarity method of Pearson & Lipman (1988) *Proc. Nat'l. Acad. Sci. USA* 85:2444-48, and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

The BLAST algorithm, described in Altschul et al. (1990) *J. Mol. Biol.* 215:403-10, is publicly available through software provided by the National Center for Biotechnology Information (available at http://www.ncbi.nlm.nih.gov). This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., 1990). Initial neighborhood word hits act as seeds for initiating searches to find longer HSPs containing them. The word hits are then extended in both directions along each sequence for as far as the cumulative alignment score can be increased. Cumulative scores are calculated for nucleotides sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=−4; and a comparison of both strands. The TBLASTN program (using a protein sequence to query nucleotide sequence databases) uses as defaults a word length (W) of 3, an expectation (E) of 10, and a BLOSUM 62 scoring matrix. See, Henikoff & Henikoff (1989) *Proc. Nat'l. Acad. Sci. USA* 89:10915-19.

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-87). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

Transcript abundance can be measured in terms of reads per kilobase of exon model per million mapped reads ("RPKM") (Mortazavi et al. (2008) *Nature Methods* 5:621-28). RPKM for a gene is calculated by dividing the gene's total number of exon reads by the product of the number of mapped reads of that gene (in millions) multiplied by the exon length (in kilobases). A gene's total number of exon reads is the number of reads that have been mapped to a region in which an exon is annotated for the gene or across the boundaries of two exons or an intron and an exon for an annotated transcript of the gene. The mapped reads include all the reads uniquely mapped to the region of the gene as well as those of the reads which match in more places that have been allocated to the gene's region. Exon length is calculated as the sum of the lengths of all exons annotated for the gene. Each exon is included only once in this sum, even if it is present in more annotated transcripts for the gene. Partly overlapping exons count for their full length, even though they share the same region.

B. Nucleotide Sequences

Genes were identified and isolated from a *Tetraselmis* environmental isolate (designated "WT-105") as sources for promoter and terminator sequences that can find use in the expression of genes, such as but not limited to transgenes, in eukaryotic microorganisms. The method by which these new promoter and terminator sequences were discovered is described more fully in the examples herein. SEQ ID NOs: 1-8 were identified as comprising promoters that were demonstrated to mediate expression of transgenes in WT-105, and SEQ ID NOs:9-10 were identified as comprising terminators functional in WT-105.

TABLE 1

Regulatory Sequence ID Numbers

| Gene name | Plasmid | Promoter 5' UTR | Terminator 3' UTR |
|---|---|---|---|
| Actin | p05439 | SEQ ID NO: 1 | SEQ ID NO: 9 |
| Glyceraldehyde 3-phosphate dehydrogenase | p05481 | SEQ ID NO: 2 | SEQ ID NO: 10 |
| Oxygen evolving enhancer protein 1 | p05482 | SEQ ID NO: 3 | |

TABLE 1-continued

Regulatory Sequence ID Numbers

| Gene name | Plasmid | Promoter 5' UTR | Terminator 3' UTR |
|---|---|---|---|
| Oxygen evolving enhancer protein 3 | p05648 | SEQ ID NO: 5 | |
| Photosystem II, reaction center W | p05605 | SEQ ID NO: 4 | |
| 40S Ribosomal protein S12 | p05606 | SEQ ID NO: 6 | |
| Photosystem I, light harvesting complex | p05607 | SEQ ID NO: 7 | |
| Reverse complement of PSI-LHC promoter | p05653 | SEQ ID NO: 8 | |

Based on the demonstration that these sequences mediate expression of heterologous genes, isolated and recombinant DNA (nucleic acid) molecules are provided herein that correspond to SEQ ID NOs:1-10 and to nucleotide sequences having about 80% identity to at least 100 contiguous nucleotides to any one of SEQ ID NOs:1-10; also provided herein are isolated or recombinant nucleic acid molecules having at least 100 contiguous nucleotides from any one of SEQ ID NOs:1-10.

For example, an isolated DNA molecule as provided herein can include: a nucleotide sequence having at least 80% identity to at least 100 contiguous nucleotides of SEQ ID NO:1; a nucleotide sequence having at least 80% identity to at least 100 contiguous nucleotides of SEQ ID NO:2; a nucleotide sequence having at least 80% identity to at least 100 contiguous nucleotides of SEQ ID NO:3; a nucleotide sequence having at least 80% identity to at least 100 contiguous nucleotides of SEQ ID NO:4; a nucleotide sequence having at least 80% identity to at least 100 contiguous nucleotides of SEQ ID NO:5; a nucleotide sequence having at least 80% identity to at least 100 contiguous nucleotides of SEQ ID NO:6; a nucleotide sequence having at least 80% identity to at least 100 contiguous nucleotides of SEQ ID NO:7; or a nucleotide sequence having at least 80% identity to at least 100 contiguous nucleotides of SEQ ID NO:8. In some examples, the isolated nucleic acid molecule can direct expression in a eukaryotic cell, such as but not limited to an algal, fungal, or heterokont cell, of a nucleic acid sequence to which it is operably linked, for example, the isolated nucleic acid molecule can direct expression of a nucleic acid sequence of a protein-encoding sequence or a sequence encoding a functional RNA.

In other examples, an isolated DNA molecule as provided herein can include a nucleotide sequence having at least 80% identity to at least 100 contiguous nucleotides of SEQ ID NO:9 or a nucleotide sequence having at least 80% identity to at least 100 contiguous nucleotides of SEQ ID NO:10. The isolated DNA molecule can mediate transcriptional termination of a gene to which it is operably linked.

Additionally or alternatively, an isolated DNA molecule as provided herein can include any of: a nucleotide sequence having at least 80% identity to at least 200 contiguous nucleotides of SEQ ID NO:1; a nucleotide sequence having at least 80% identity to at least 200 contiguous nucleotides of SEQ ID NO:2; a nucleotide sequence having at least 80% identity to at least 200 contiguous nucleotides of SEQ ID NO:3; a nucleotide sequence having at least 80% identity to at least 200 contiguous nucleotides of SEQ ID NO:4; a nucleotide sequence having at least 80% identity to at least 200 contiguous nucleotides of SEQ ID NO:5; a nucleotide sequence having at least 80% identity to at least 200 contiguous nucleotides of SEQ ID NO:6; a nucleotide sequence having at least 80% identity to at least 200 contiguous nucleotides of SEQ ID NO:7; and a nucleotide sequence having at least 80% identity to at least 200 contiguous nucleotides of SEQ ID NO:8

Additionally or alternatively, an isolated DNA molecule as provided herein can include any of: a nucleotide sequence having at least 80% identity to at least 300, at least 400, or at least 500 contiguous nucleotides of SEQ ID NO:1; a nucleotide sequence having at least 80% identity to at least 300, at least 400, or at least 500 contiguous nucleotides of SEQ ID NO:2; a nucleotide sequence having at least 80% identity to at least 300, at least 400, or at least 500 contiguous nucleotides of SEQ ID NO:3; a nucleotide sequence having at least 80% identity to at least 300, at least 400, or at least 500 contiguous nucleotides of SEQ ID NO:4; a nucleotide sequence having at least 80% identity to at least 300, at least 400, or at least 500 contiguous nucleotides of SEQ ID NO:5; a nucleotide sequence having at least 80% identity to at least 300, at least 400, or at least 500 contiguous nucleotides of SEQ ID NO:6; a nucleotide sequence having at least 80% identity to at least 300, at least 400, or at least 500 contiguous nucleotides of SEQ ID NO:7; and a nucleotide sequence having at least 80% identity to at least 300, at least 400, or at least 500 contiguous nucleotides of SEQ ID NO:8. The isolated DNA molecule can have promoter activity. For example the isolated DNA molecule can mediate or enhance expression of a heterologous nucleic acid sequence to which it is operably linked.

Additionally or alternatively, an isolated DNA molecule as provided herein can include a nucleotide sequence having at least 80% identity to SEQ ID NO:1; a nucleotide sequence having at least 80% identity to SEQ ID NO:2; a nucleotide sequence having at least 80% identity to SEQ ID NO:3; a nucleotide sequence having at least 80% identity to SEQ ID NO:4; a nucleotide sequence having at least 80% identity to SEQ ID NO:5; a nucleotide sequence having at least 80% identity to SEQ ID NO:6; a nucleotide sequence having at least 80% identity to SEQ ID NO:7; and a nucleotide sequence having at least 80% identity to SEQ ID NO:8. The isolated DNA molecule can have promoter activity. For example the isolated DNA molecule can mediate or enhance expression of a heterologous nucleic acid sequence to which it is operably linked.

Additionally or alternatively, an isolated DNA molecule as provided herein can have at least 85% or at least 90% identity to at least 100, at least 200, at least 300, at least 400, or at least 500 contiguous nucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8. In some examples, an isolated DNA molecule can have at least 95% sequence identity to at least 100, at least 200, at least 300, at least 400, or at least 500 contiguous nucleotides of SEQ ID NO:1. Additionally or alternatively, an isolated DNA molecule can have at least 95% sequence identity to at least 100, at least 200, at least 300, at least 400, or at least 500 contiguous nucleotides of SEQ ID NO:2. Further additionally or alternatively, an isolated DNA molecule can have at least 95% sequence identity to at least 100, at least 200, at least 300, at least 400, or at least 500 contiguous nucleotides of SEQ ID NO:3. Further alternatively or additionally, an isolated DNA molecule can have at least 95% sequence identity to at least 100, at least 200, at least 300, at least 400, or at least 500 contiguous nucleotides of SEQ ID NO:4. Further additionally or alternatively, an isolated DNA molecule can have at least 95% sequence identity to at least 100, at least 200, at least 300, at least 400, or at least 500 contiguous nucleotides of SEQ ID NO:5. Additionally or alternatively, an isolated DNA molecule can have at least 95% sequence identity to at least 100, at least 200, at least 300, at least 400, or at least 500 contiguous nucleotides of SEQ ID NO:6. Further additionally or alternatively, an isolated DNA molecule can have at least 95% sequence identity to at least 100, at least 200, at least 300, at least 400, or at least 500 contiguous nucleotides of SEQ ID NO:7. Further additionally or alternatively, an isolated DNA molecule can have at least 95% sequence identity to at least 100, at least 200, at least 300, at least 400, or at least 500 contiguous nucleotides of SEQ ID NO:8. The isolated DNA molecule can mediate or enhance expression of a heterologous nucleic acid sequence to which it is operably linked.

In another aspect, provided herein is an isolated DNA molecule comprising a nucleotide sequence having at least 80% identity to at least 200 contiguous nucleotides of SEQ ID NO:9 and a nucleotide sequence having at least 80% identity to at least 200 contiguous nucleotides of SEQ ID NO:10. For example, an isolated DNA molecule can comprise a nucleotide sequence having at least 80% identity to at least 300, at least 400, or at least 500 contiguous nucleotides of SEQ ID NO:9, or a nucleotide sequence having at least 80% identity to at least 300, at least 400, or at least 500 contiguous nucleotides of SEQ ID NO:10, and can comprise a nucleotide sequence having at least 80% identity to SEQ ID NO:9 or a nucleotide sequence having at least 80% identity to SEQ ID NO:10. Further alternatively or additionally, an isolated DNA molecule can have at least 95% sequence identity to at least 100, at least 200, at least 300, at least 400, or at least 500 contiguous nucleotides of SEQ ID NO:9. Further alternatively or additionally, an isolated DNA molecule can have at least 95% sequence identity to at least 100, at least 200, at least 300, at least 400, or at least 500 contiguous nucleotides of SEQ ID NO:10. The isolated DNA molecule can have terminator activity. For example, the isolated DNA molecule can mediate transcriptional termination of a gene to which is operably linked Additionally or alternatively, an isolated DNA molecule as provided herein can include a nucleotide sequence that can have at least 95%, 96%, 97%, 98%, or 99% percent identity to at least 100 contiguous nucleotides to any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

Additionally or alternatively, an isolated DNA molecule can comprise at least 100, at least 200, at least 300, at least 400, or at least 500 contiguous nucleotides of SEQ ID NO:1; at least 100, at least 200, at least 300, at least 400, or at least 500 contiguous nucleotides of SEQ ID NO:2; at least 100, at least 200, at least 300, at least 400, or at least 500 contiguous nucleotides of SEQ ID NO:3; at least 100, at least 200, at least 300, at least 400, or at least 500 contiguous nucleotides of SEQ ID NO:4; at least 100, at least 200, at least 300, at least 400, or at least 500 contiguous nucleotides of SEQ ID NO:5; at least 100, at least 200, at least 300, at least 400, or at least 500 contiguous nucleotides of SEQ ID NO:6; at least 100, at least 200, at least 300, at least 400, or at least 500 contiguous nucleotides of SEQ ID NO:7; at least 100, at least 200, at least 300, at least 400, or at least 500 contiguous nucleotides of SEQ ID NO:8; at least 100, at least 200, at least 300, at least 400, or at least 500 contiguous nucleotides of SEQ ID NO:9; or at least 100, at least 200, at least 300, at least 400, or at least 500 contiguous nucleotides of SEQ ID NO:10.

Additionally or alternatively, an isolated DNA molecule can comprise a nucleotide sequence having at least 95% identity to any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. For example, an isolated DNA molecule can comprise a nucleotide sequence having at least 96%, 97%, 98%, or 99% identity to any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. In further examples, an isolated DNA molecule can comprise any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

The isolated DNA molecule can find use, for example, as a sequence that when operably linked to a nucleic acid sequence can affect expression of the nucleic acid sequence, which can comprise, for example, a sequence encoding a polypeptide or functional RNA. For example, the isolated DNA molecule can increase or decrease expression of a nucleic acid sequence (or a portion thereof) to which it is operably linked, or may mediate transcription of the operably-linked nucleic acid sequence (or a portion thereof) as a promoter. Methods for assessing the functionality of nucleotide sequences for promoter activity, as well as for enhancing or decreasing the activity of proximal promoters, are well-known in the art. For example, promoter function can be validated by confirming the ability of the putative promoter or promoter variant or fragment to drive expression of a selectable marker gene to which the putative promoter or promoter fragment or variant is operably linked by detecting and, optionally, analyzing, resistant colonies after plating of cells transformed with the promoter construct on selective media.

Additionally or alternatively, promoter activity may be assessed by measuring the levels of RNA transcripts produced from a promoter construct, for example, using reverse transcription-polymerase chain reaction (RT-PCR, e.g., Watt et al. (2008) *PLoS ONE* 1:e1428), by detection of the expressed protein, or by in vivo assays that rely on an activity of the protein encoded by the transcribed sequence. For example, promoter activity can be assessed using chloramphenicol acetyltransferase (CAT) assays (where the heterologous sequence operably linked to the isolated nucleic acid molecule that comprises a putative promoter encodes chloramphenicol acetyltransferase, see, for example, Gerrish et al. (2000) *J. Biol. Chem.* 275:3485-92), luciferase assays, where the heterologous nucleic acid is a lux or luc gene, for example (see, for example, Ferrante et al. (2008) *PLoS ONE* 3:e3200), or in vivo assays using a fluorescent protein gene to determine the functionality of any of the sequences disclosed herein, including sequences of reduced size or having one or more nucleotide changes with respect to any of SEQ ID NOs 1-8. (see, for example, Akamura et al. (2011) *Anal. Biochem.* 412:159-64). Testing of sequence modifications, including deletions and base substitutions of the promoter-containing sequences using reporter constructs such as but not limited to those provided herein are well-known in the art (see, for example, Quinn et al. (2003) *Eukaryotic Cell* 2:995-1002; Ranjan et al. (2011) *J. Biotechnol.* 152:58-62; Gerrish et al., 2000).

Promoters

Also provided herein are promoters comprising a nucleic acid sequence such as any described herein, for example, a nucleic acid sequence having at least 80%, at least 85%, at least 90%, or at least 95% identity to at least 100 contiguous nucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8. For example, a promoter as provided herein may include a nucleotide sequence that has at least 85% or at least 90% sequence identity to at least 100, 200, 300, 400, or 500 contiguous nucleotides of SEQ ID NO:1, at least 85% or at least 90% sequence identity to at least 100, 200, 300, 400, or 500 contiguous nucleotides of SEQ ID NO:2, at least 85% or at least 90% sequence identity to at least 100, 200, 300, 400, or 500 contiguous nucleotides of SEQ ID NO:3, at least 85% or at least 90% sequence identity to at least 100, 200, 300, 400, or 500 contiguous nucleotides of SEQ ID NO:4, at least 85% or at least 90% sequence identity to at least 100, 200, 300, 400, or 500 contiguous nucleotides of SEQ ID NO:5, at least 85% or at least 90% sequence identity to at least 100, 200, 300, 400, or 500 contiguous nucleotides of SEQ ID NO:6, at least 85% or at least 90% sequence identity to at least 100, 200, 300, 400, or 500 contiguous nucleotides of SEQ ID NO:7, or at least 85% or at least 90% sequence identity to at least 100, 200, 300, 400, or 500 contiguous nucleotides of SEQ ID NO:8.

Additionally or alternatively, a promoter can include a sequence that has at least 95% sequence identity to at least 100, 200, 300, 400, or 500 contiguous nucleotides of SEQ ID NO:1, at least 95% sequence identity to at least 100, 200, 300, 400, or 500 contiguous nucleotides of SEQ ID NO:2, at least 95% sequence identity to at least 100, 200, 300, 400, or 500 contiguous nucleotides of SEQ ID NO:3, at least 95% sequence identity to at least 100, 200, 300, 400, or 500 contiguous nucleotides of SEQ ID NO:4, at least 95% sequence identity to at least 100, 200, 300, 400, or 500 contiguous nucleotides of SEQ ID NO:5, at least 95% sequence identity to at least 100, 200, 300, 400, or 500 contiguous nucleotides of SEQ ID NO:6, at least 95% sequence identity to at least 100, 200, 300, 400, or 500 contiguous nucleotides of SEQ ID NO:7, or at least 95% sequence identity to at least 100, 200, 300, 400, or 500 contiguous nucleotides of SEQ ID NO:8.

Additionally or alternatively, a promoter as provided herein can be selected from the group consisting of an isolated DNA molecule comprising at least 100 contiguous nucleotides of SEQ ID NO:1; an isolated DNA molecule comprising at least 100 contiguous nucleotides of SEQ ID NO:2; an isolated DNA molecule comprising at least 100 contiguous nucleotides of SEQ ID NO:3; an isolated DNA molecule comprising at least 100 contiguous nucleotides of SEQ ID NO:4; an isolated DNA molecule comprising at least 100 contiguous nucleotides of SEQ ID NO:5; an isolated DNA molecule comprising at least 100 contiguous nucleotides of SEQ ID NO:6; an isolated DNA molecule comprising at least 100 contiguous nucleotides of SEQ ID NO:7; and an isolated DNA molecule comprising at least 100 contiguous nucleotides of SEQ ID NO:8.

A promoter provided herein can include a nucleotide sequence having at least 90%, at least 95%, at least 96%, at least 97%, at least 98%, at least 99%, or about 100% sequence identity to at least 250, at least 300, at least 400, at least 500, at least 600, or at least 700 contiguous nucleotides of SEQ ID NO:1. For example, a promoter provided herein can have at least 95% sequence identity to SEQ ID NO:1.

Additionally or alternatively, a promoter provided herein can include a nucleotide sequence having at least 90%, at least 95%, at least 96%, at least 97%, at least 98%, at least 99%, or about 100% sequence identity to at least 250, at least 300, at least 400, or at least 500, at least 750, at least 1000, at least 1200, at least 1300, at least 1400, or at least 1500 contiguous nucleotides of SEQ ID NO:2. For example, a promoter provided herein can have at least 95% sequence identity to SEQ ID NO:2.

Additionally or alternatively, a promoter provided herein can include a nucleotide sequence having at least 90%, at least 95%, at least 96%, at least 97%, at least 98%, at least 99%, or about 100% sequence identity to at least 250, at least 300, at least 400, at least 500, at least 750, at least 1000, at least 1200, at least 1300, at least 1400, or at least 1500 contiguous nucleotides of SEQ ID NO:3. For example, a promoter provided herein can have at least 95% sequence identity to SEQ ID NO:3.

Additionally or alternatively, a promoter provided herein can include a nucleotide sequence having at least 90%, at least 95%, at least 96%, at least 97%, at least 98%, at least 99%, or about 100% sequence identity to at least 250, at least 300, at least 400, at least 500, at least 600, at least 700, or at least 800 contiguous nucleotides of SEQ ID NO:4. For example, a promoter provided herein can have at least 95% sequence identity to SEQ ID NO:4.

Additionally or alternatively, a promoter provided herein can include a nucleotide sequence having at least 90%, at least 95%, at least 96%, at least 97%, at least 98%, at least 99%, or about 100% sequence identity to at least 250, at least 300, at least 400, at least 500, at least 600, at least 700, at least 800, at least 900, or at least 1000 contiguous nucleotides of SEQ ID NO:5. For example, a promoter provided herein can have at least 95% sequence identity to SEQ ID NO:5.

Additionally or alternatively, a promoter provided herein can include a nucleotide sequence having at least 90%, at least 95%, at least 96%, at least 97%, at least 98%, at least 99%, or about 100% sequence identity to at least 250, at least 300, at least 400, at least 500, at least 600, at least 700, at least 800, at least 900, at least 950, or at least 1000 contiguous nucleotides of SEQ ID NO:6. For example, a promoter provided herein can have at least 95% sequence identity to SEQ ID NO:6.

Additionally or alternatively, a promoter provided herein can include a nucleotide sequence having at least 90%, at least 95%, at least 96%, at least 97%, at least 98%, at least 99%, or about 100% sequence identity to at least 250, at least 300, at least 400, at least 500, at least 600, at least 700, at least 800, at least 900, or at least 950 contiguous nucleotides of SEQ ID NO:7. For example, a promoter provided herein can have at least 95% sequence identity to SEQ ID NO:7.

Additionally or alternatively, a promoter provided herein can include a nucleotide sequence having at least 90%, at least 95%, at least 96%, at least 97%, at least 98%, at least 99%, or about 100% sequence identity to at least 250, at least 300, at least 400, at least 500, at least 600, at least 700, at least 800, at least 900, or at least 950 contiguous nucleotides of SEQ ID NO:8. For example, a promoter provided herein can have at least 95% sequence identity to SEQ ID NO:8.

In various examples of promoters of the present invention a promoter is selected from the group consisting of: SEQ ID NO:1; SEQ ID NO:2; SEQ ID NO:3; SEQ ID NO:4; SEQ ID NO:5; SEQ ID NO:6; SEQ ID NO:7; and SEQ ID NO:8.

A promoter as provided herein can be a constitutive promoter, for example the promoter may be active in culture conditions in which one or more nutrients are deficient as well as in culture conditions in which nutrients are sufficient for proliferation and/or growth of the culture. For example, a promoter as provided herein may direct expression of an operably linked nucleic acid sequence under conditions in which a host cell that includes the promoter construct is limited in nitrogen availability (nitrogen depletion/deficiency) as well as under conditions in which a host cell that includes the promoter construct is not limited in nitrogen availability (nitrogen replete conditions).

Without being bound by theory, promoters allow RNA polymerase to attach to DNA near a gene in order for transcription to take place. Promoters contain specific DNA sequences that provide transcription factors to an initial binding site from which they can recruit RNA polymerase binding. These transcription factors have specific protein motifs that enable them to interact with specific corresponding nucleotide sequences to regulate gene expressions. The minimal portion of the promoter required for proper transcription initiate include: (1) the Transcription Start Site ("TSS") and elements directly upstream; (2) an RNA polymerase binding site; and (3) general transcription factor binding sites, e.g. a TATA box (sequence TATAAA).

A proximal promoter sequence may be approximately 250 basepairs (bp) upstream of the translational start site of the open reading frame of the gene and may contain, in addition to sequences for binding RNA polymerase, specific transcription factor binding sites. Some promoters also include a distal sequence upstream of the gene that may contain additional regulatory elements, often with a weaker influence than the proximal promoter. Eukaryotic transcriptional complexes can bend the DNA back on itself, thus allowing for potential placement of additional regulatory sequences as far as several kilobases from the TSS. Many eukaryotic promoters contain a TATA box. The TATA box binds the TATA binding protein, which assists in the formation of the RNA polymerase transcriptional complex. TATA boxes usually lie within approximately 50 bp of the TSS. A promoter may be constitutive or expressed conditionally. Some promoters are inducible, and may activate or increase transcription in response to an inducing agent. In contrast, the rate of transcription of a gene under control of a constitutive promoter is not dependent on an inducing agent. A constitutive promoter can be made a conditional or inducible promoter by the addition of sequences that confer responsiveness to particular conditions or to an inducing agent. Thus, promoters provided herein may be constitutive or may be inducible or conditional. Further, promoters or portions of promoters may be combined in series to achieve a stronger level of expression or a more complex pattern of regulation.

In various examples, a promoter as provided herein, such as but not limited to a promoter that comprises a nucleotide sequence having at least 80%, at least 85%, at least 90%, at least 95%, at least 96%, at least 97%, at least 98%, at least 99%, or about 100% identity to at least 100, at least 200, at least 300, at least 400, or at least 500 contiguous nucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, can mediate transcription of an operably linked nucleic acid sequence in a eukaryotic algal cell, such as, for example, a *Tetraselmis* cell. In some instances, a promoter as provided herein can mediate transcription of an operably linked nucleic acid sequence in a eukaryotic cell, such as but not limited to a eukaryotic algal cell, during culturing of the cell under conditions of nitrogen depletion as well as during culturing of the cell under nitrogen replete conditions. For example, a promoter as described herein can preferably mediate transcription of an operably linked nucleic acid sequence in *Tetraselmis* cells cultured under conditions of nitrogen depletion or cultured under nitrogen replete conditions.

Additionally, as contemplated herein, a promoter or promoter region can include variants of the promoters disclosed herein derived by deleting sequences, duplicating sequences, or adding sequences from other promoters or as designed, for example, by bioinformatics, or by subjecting the promoter to random or site-directed mutagenesis, etc.

Any of the nucleic acid molecules described herein may comprise nucleic acid sequences comprising promoters. For example, promoters of the present invention can include nucleic acid sequences having at least 80%, at least 85%, at least 90%, at least 95%, or between 95% and 100% identity to the sequences between about 0 bp, 20 bp, 50 bp, 100 bp, 200 bp or 300 bp to about 500 bp, 600 bp, 700 bp, 800 bp, 900 bp, or 1 kb upstream of the trinucleotide ATG sequence at the start site of a protein coding region of a native *Tetraselmis* gene, such as, for example, an actin gene, a glyceraldehyde 3-phosphate dehydrogenase gene, an oxygen evolving enhancer protein 1 (psbO) gene, a photosystem II reaction center W gene, an oxygen evolving enhancer protein 3 gene, a 40S ribosomal protein S12 gene, or a photosystem I light harvesting complex (PSI-LHC) gene.

Additionally or alternatively, promoters of the present invention can include nucleic acid sequences having at least 80%, at least 85%, at least 90%, at least 95%, or between 95% and 100% identity to the reverse complement of sequences between about 0 bp, 20 bp, 50 bp, 100 bp, 200 bp or 300 bp to about 500 bp, 600 bp, 700 bp, 800 bp, 900 bp, or 1 kb upstream of the trinucleotide ATG sequence at the start site of a protein coding region of a native *Tetraselmis* gene, such as, a photosystem I light harvesting complex gene.

The activity or strength of a promoter may be measured in terms of the amount of RNA it produces, or the amount of protein accumulation in a cell or tissue, which can optionally be measured by an activity of the expressed protein, e.g., fluorescence, luminescence, acyltransferase activity, etc., relative to a promoter whose transcriptional activity has been previously assessed, relative to a promoterless construct, or relative to non-transformed cells. For example, the activity or strength of a promoter may be measured in terms of the amount of mRNA accumulated that corresponds to a nucleic acid sequence to which it is operably linked in a cell, relative to the total amount of mRNA or protein produced by the cell. The promoter preferably expresses an operably linked nucleic acid sequence at a level greater than 0.01%; preferably in a range of about 0.5% to about 20% (w/w) of the total cellular RNA. The activity can also be measured by quantifying fluorescence, luminescence, or absorbance of the cells or a product made by the cells or an extract thereof, depending on the activity of a reporter protein that may be expressed from the promoter. The activity or strength of a promoter may be expressed relative to a well-characterized promoter (for which transcriptional activity was previously assessed). For example, a less-characterized promoter may be operably linked to a reporter sequence (e.g., a fluorescent protein) and introduced into a specific cell type. A well-characterized promoter is similarly prepared and introduced into the same cellular context. Transcriptional activity of the unknown promoter is determined by comparing the amount of reporter expression, relative to the well characterized promoter.

A promoter described herein can have promoter activity in a eukaryotic cell, preferably in an algal cell or heterokont cell. In a particular examples, a promoter as provided herein is active in an algal or heterokont cell in nutrient replete and nutrient-depleted culture conditions. An algal promoter as provided herein can be used as a 5' regulatory element for modulating expression of an operably linked gene or genes in algal species as well as other organisms, including fungi, heterokonts, and plants.

Using promoter assay methods, such as but not limited to the method described in Examples 2 and 3, the disclosed promoter sequences can be further modified, e.g. truncated or mutated, and screened to refine the active promoter regions.

Terminators

In another embodiment of the present invention terminators are provided in which the terminators comprise a nucleotide sequence having at least 80%, at least 85%, at least 90%, at least 95%, at least 96%, at least 97%, at least 98%, at least 99%, or about 100% sequence identity to at least 100 or at least 150 contiguous nucleotides of SEQ ID NO:9 or SEQ ID NO:10.

For example, a terminator can have at least 80%, at least 85%, at least 90%, at least 95%, at least 96%, at least 97%, at least 98%, at least 99%, or about 100% sequence identity to at least 200, at least 300, at least 400, at least 500, at least 600, at least 700, at least 800, at least 900, or at least 950 contiguous nucleotides of SEQ ID NO:9.

Additionally or alternatively, a terminator can have at least 80%, at least 85%, at least 90%, at least 95%, at least 96%, at least 97%, at least 98%, at least 99%, or about 100% sequence identity to at least 200, at least 300, at least 400, at least 500, at least 600, at least 700, at least 800, at least 900, or at least 1000 contiguous nucleotides of SEQ ID NO:10.

Terminators are genetic sequences that mark the end of a gene for transcription. Without being bound by theory, the terminators of the present invention may improve expression of a nucleic acid sequence (amount of encoded RNA or protein produced), and may mediate polyadenylation or enhance RNA transcript stability. Most terminator sequences in eukaryotes consist of at least two DNA sequences: (1) a binding site for terminator proteins and (2) an upstream element located among the last twelve nucleotides of the transcript. The protein binding sites are usually orientation-sensitive and essential to termination. Termination usually occurs between twelve and twenty nucleotides upstream of the binding site. The upstream element's functionality usually depends more on its overall base composition (T-rich) than on the specific sequence (Reeder & Lang (1997) *Trends Biochem. Sci.* 22:473-77, herein incorporated by reference in its entirety).

C. Expression Cassettes

Expression cassettes are also provided in the present invention, in which the expression cassettes comprise one or more regulatory elements as described herein to drive the expression of transgenes. These cassettes comprise isolated nucleic acid molecules that include any one of the promoter sequences described herein or any combination thereof, operably linked to a gene of interest, with the gene of interest positioned downstream of the promoter sequence, and optionally with any one of the terminator sequences described herein or any combination thereof operably linked downstream of the transgene. For example, any of the promoters listed in Table 1 can be used in combination with any terminator listed in Table 1 in an expression cassette.

The basic techniques for operably linking two or more sequences of DNA together are familiar to the skilled worker, and such methods have been described in a number of texts for standard molecular biological manipulation (see, e.g., "*Molecular Cloning: A Laboratory Manual*," $2^{nd}$ ed. Cold Spring Harbor Laboratory Press, Cold Spring Harbor, N.Y.; Gibson et al. (2009) *Nature Methods* 6:343-45).

The promoters of the invention can be used with any heterologous or homologous gene(s). A heterologous or homologous gene according to the invention may encode a protein or polypeptide. Alternatively, the heterologous or homologous gene can encode a functional RNA, such as a tRNA, rRNA, small nucleolar RNA (snoRNA), ribozyme, antisense RNA (asRNA), micro RNA (miRNA), short hairpin RNA (shRNA), small interfering RNA (siRNA), or piwi-interacting RNA (piRNA). Any known or later-discovered heterologous or homologous gene which encodes a desired product can be operably linked to a promoter sequence of the invention using known methods. Non-limiting examples of known genes suitable for use with the promoters of the invention include genes encoding proteins associated with lipid biosynthesis; proteins having lipolytic activity; proteins associated with carbohydrate metabolism; transporter polypeptides; proteins conferring resistance to an antibiotic, herbicide, or toxin; reporter proteins (e.g., fluorescent proteins or enzymes that produce detectable products) polypeptides of the Calvin-Benson cycle; polypeptides that participate in photosynthesis (such as but not limited to, photosynthetic reaction center polypeptides, light-harvesting chlorophyll-binding proteins, oxygen-evolving complex polypeptides, cytochromes, ferredoxins, etc.); dehdrogenases, such as NADPH-forming dehydrogenases; transcription factors; proteins involved in cell signaling (e.g., G proteins or kinases); or functional RNAs.

For example, an expression cassette can comprise a promoter as described herein (for example, a promoter comprising a nucleotide sequence having at least 80% identity to at least 100 contiguous nucleotides of SEQ ID NOs:1, 2, 3, 4, 5, 6, 7, or 8) operably linked to a gene encoding a polypeptide, where the polypeptide can be any polypeptide of interest, and in illustrative and nonlimiting examples, can be a protein associated with lipid biosynthesis, an acetyl-CoA carboxylase, a malonyl type 1 fatty acid synthase, a type 2 fatty acid synthase subunit, a beta ketoacyl-ACP synthase, a malonyl-CoA-malonyl-ACP acyltransferase, an acyl-ACP thioesterase, an acyl-CoA thioesterase, a 4-hydroxybenzoyl thioesterase, an alcohol forming acyl reductase, a wax synthase, an aldehyde decarbonylase, a fatty acid decarboxylase, a lipase, a glyceraldehyde 3 phosphate dehydrogenase, an acyl-CoA synthetase, a phospholipid diacylglycerol acyltransferase, a glycerol 3 phosphate acyltransferase, a lysophosphatidic acid acyltransferase, a phosphatidic acid phosphatase, a diacyl glycerol acyltransferase, a polypeptide that participates in photosynthesis, a chlorophyll-binding light harvesting polypeptide, a photosynthetic reaction center polypeptide, an oxygen-evolving complex polypeptide, a cytochrome, a ferredoxin, a protein associated with carbon fixation, a ribulose bisphoshate carboxylase subunit, a carbonic anhydrase, a transporter protein, an ABC transporter, a FatB transporter, a dehydrogenase, an aldehyde dehydrogenase, a 2-hydroxyacid dehydrogenase, an isocitrate dehydrogenase, 6 phosphogluconate dehydrogenase, glucose 6 phosphate dehydrogenase, a transcription factor, a kinase, or a G protein.

In further examples, an expression cassette can comprise a promoter as described herein (for example, a promoter comprising a nucleotide sequence having at least 80% identity to at least 100 contiguous nucleotides SEQ ID NO:1, 2, 3, 4, 5, 6, 7, or 8) operably linked to a gene encoding a functional RNA, optionally wherein the functional RNA is an antisense RNA, a small hairpin RNA, a microRNA, an siRNA, an snoRNA, a piRNA, or a ribozyme.

D. Vectors

The present invention also provides vectors that can comprise the regulatory elements and/or expression cassettes described herein. The vectors can further optionally comprise at least one origin of replication ("ORI") sequence for replication in a cell. The vectors may further optionally comprise one or more selectable markers under the control of one or more eukaryotic promoters, one or more selectable markers under the control of one or more prokaryotic promoters, and/or one or more sequences that mediate recombination of an exogenous nucleic acid sequence into the target cell's genome.

An ORI is the sequence in a DNA molecule at which replication begins. The ORI serves as a base of assembly for the pre-replication complex. Depending on the ORI, such replication can proceed unidirectionally or bidirectionally. An expression vector as provided herein can include an ORI for replication of the expression vector in a cloning host, such as E. coli or Saccharomyces, and/or can include an ORI for replication of the expression vector in a target cell, which can be, for example, an algal or heterokont cell. The structural biology of ORIs is widely conserved among prokaryotes, eukaryotes, and viruses. Most ORIs possess simple tri-, tetra-, or higher nucleotide repetition patterns. Most are AT-rich and contain inverted repeats. Those skilled in the art will be familiar with the more common ORIs, such as p15A and the pUC ORI.

Additionally, a vector described herein may also carry a selectable marker. By way of example, a vector that includes an expression cassette may include, as a selectable marker, a gene conferring resistance to a poison, such as an antibiotic, a herbicide, or some other toxin, so that transformants can be selected by exposing the cells to the poison and selecting those cells which survive the encounter. Non-limiting examples of selectable markers include:

genes conferring resistance to antibiotics such as amikacin (aphA6), ampicillin (amp$^R$), blasticidin (bls, bsr, bsd), bleomicin or phleomycin (ZEOCIN™) (ble), chloramphenicol (cat), emetine (RBS14p or cry1-1), erythromycin (ermE), G418 (GENETICIN™) (neo), gentamycin (aac3 or aacC4), hygromycin B (aphIV, hph, hpt), kanamycin (nptII), methotrexate (DHFR mtx$^R$), penicillin and other β-lactams (β-lactamases), streptomycin or spectinomycin (aadA, spec/strep), and tetracycline (tetA, tetM, tetQ);

genes conferring resistance or tolerance to herbicides such as aminotriazole, amitrole, andrimid, aryloxyphenoxy propionates, atrazines (psbA), bipyridyliums, bromoxynil, cyclohexandione oximes dalapon, dicamba, diclfop, dichlorophenyl dimethyl urea (DCMU), difunone, diketonitriles, diuron, fluridone, glufosinate, glyphosate, halogenated hydrobenzonitriles, haloxyfop, 4-hydroxypyridines, imidazolinones, isoxasflutole, isoxazoles, isoxazolidinones, miroamide B, p-nitrodiphenylethers, norflurazon, oxadiazoles, m-phenoxybenzamides, N-phenyl imides, pinoxadin, protoporphyrionogen oxidase inhibitors, pyridazinones, pyrazolinates, sulfonylureas, 1,2,4-triazol pyrimidine, triketones, urea compounds; acetyl CoA carboxylase (ACCase), acetohydroxy acid synthase (ahas), acetolactate synthase (als, csr1-1, csr1-2, imr1, imr2), aminoglycoside phosphotransferase (apt), anthranilate synthase, bromoxynil nitrilase (bxn), cytochrome P450-NADH-cytochrome P450 oxidoreductase, dalapon dehalogenase (dehal), dihydropteroate synthase (sul), class I 5-enolpyruvylshikimate-3-phosphate synthase (EPSPS), class II EPSPS (aroA), non-class I/II EPSPS, glutathione reductase, glyphosate acetyltransferase (gat), glyphosate oxidoreductase (gox), hydroxyphenylpyruvate dehydrogenase, hydroxy-phenylpyruvate dioxygenase (hppd), isoprenyl pyrophosphate isomerase, lycopene cyclase, phosphinothricin acetyl transferase (pat, bar), phytoene desaturase (crtI), prenyl transferase, protoporphyrin oxidase, psbA of photosystem II (psbA), and SMM esterase (SulE) superoxide dismutase (sod);

genes that may be used in auxotrophic strains or to confer autotrophic growth or other metabolic effects, such as arg7, his3, hisD, hisG, lysA, manA, metE, nit1, trpB, ura3, xylA, a dihydrofolate reductase gene, a mannose-6-phosphate isomerase gene, a nitrate reductase gene, or an ornithine decarboxylase gene; a negative selection factor such as thymidine kinase; or toxin resistance factors such as a 2-deoxyglucose resistance gene.

The selectable marker gene can be operably linked to and/or under the control of a promoter as provided herein. The promoter regulating expression of the selectable marker may be conditional or inducible but is preferably constitutive, and can be, for example, any promoter disclosed herein or another promoter. Alternatively, the selectable marker may be placed under the control of the expression cassette promoter. If a selectable marker is placed under the control of the expression cassette promoter, the selectable marker and the expression cassette may be operably linked with an internal ribosome entry site ("IRES") element between the expression cassette and the selectable marker (Komar & Hatzoglou (2011) Cell Cycle 10:229-40 and Hellen & Sarnow (2001) Genes & Dev. 15:1593-612, incorporated by reference in their entireties) or a "2A" sequence (Kim et al. (2011) PLoS One 6:e18556, incorporated by reference in its entirety).

Further provided herein is a vector for transformation of a eukaryotic cell, such as but not limited to a eukaryotic microalgal cell or phytoplankter cell, in which the vector includes a selectable marker gene operably linked to a promoter as provided herein, for example, a promoter that includes a nucleotide sequence having at least 80%, at least 85%, at least 90%, at least 95%, at least 96%, at least 97%, at least 98%, at least 99%, or about 100% sequence identity to at least 100, at least 200, at least 300, at least 400, at least 500, at least 600, at least 700, or at least 800 contiguous nucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or a promoter that comprises SEQ ID NO:1, SEQ ID NO:2, SEQ ID NO:3, SEQ ID NO:4, SEQ ID NO:5, SEQ ID NO:6, SEQ ID NO:7, or SEQ ID NO:8. The transformation vector can further include one or more additional genes or constructs for transfer into the host cell, such as a gene encoding a polypeptide such as but not limited to any disclosed hereinabove or a construct encoding a functional RNA, where the gene encoding a polypeptide or functional RNA can optionally be operably linked to a promoter as described herein, or can optionally be operably linked to another promoter.

Additionally or alternatively, the vectors as provided herein may comprise a terminator as provided herein. For example, a vector of the present invention may comprise a nucleotide sequence having at least 80%, at least 85%, at least 90%, at least 95%, at least 96%, at least 97%, at least 98%, at least 99%, or about 100% sequence identity to at least 100, at least 200, at least 300, at least 400, at least 500, at least 600, at least 700, or at least 800 contiguous nucleotides of SEQ ID NO:9 or SEQ ID NO:10. A gene of interest or a selectable marker gene on a vector of the present invention may be operably linked to a terminator sequence as provided herein. For example, a gene of interest or a selectable marker may be operably linked to SEQ ID NO:9. By way of further example, a gene of interest or a selectable marker gene may be operably linked to SEQ ID NO:10.

In an alternative transformation strategy, a selectable marker operably linked to a promoter such as a promoter described herein can be provided on a separate construct, where both the gene-of-interest construct and the selectable marker construct are used together in transformation protocols. Selected transformants are then analyzed for co-transformation of the construct that includes the gene-of-interest (see, e.g., Kindle (1990) Proc. Nat'l. Acad. Sci. USA 87:1228-32).

If a vector as provided herein that includes an expression cassette lacks a selectable marker gene, transformants may be selected by routine methods familiar to those skilled in the art, such as, by way of a non-limiting example, extracting nucleic acid from the putative transformants and screening by PCR. Alternatively or in addition, transformants may be screened by detecting expression of a reporter gene, such as but not limited to a chloramphenicol acyltransferase gene (cat) lacZ, uidA, xylE, an alkaline phosphatase gene, an α-amylase gene, an α-galactosidase gene, a β-lactamase gene, a β-glucuronidase gene, a horseradish peroxidase gene, a luciferin/luciferase gene, an R-locus gene, a tyrosinase gene, or a gene encoding a fluorescent protein, such as any of the blue, cyan, green, red, yellow, photoconvertible, or photoswitchable fluorescent proteins or any of their variants, including codon-optimized, rapidly folding, monomeric, increased stability, and enhanced fluorescence variants. A reporter gene used in a vector may optionally be regulated by a promoter as provided herein. A transformation vector may include a gene encoding a reporter, such as, for example, a fluorescent protein, operably linked to a promoter as provided herein.

In some examples, the vector is designed for integration of one or more genes (such as the expression cassette) into the host genome. For example, the expression vectors may include Agrobacterium flanking sequences designed for integrating transgenes into the genome of a target plant cell. In other embodiments, vectors can be targeted for integration into a plant or algal chromosome by including flanking sequences that enable homologous recombination into the chromosome or targeted for integration into endogenous host plasmids by including flanking sequences that enable homologous recombination into the endogenous plasmids. In some cases in which it may be advantageous to transform the chloroplast of a higher plant or alga, the expression vectors can be designed to have regions of sequences flanking the transgene that are homologous to chloroplast sequences to promote homologous recombination and integration of the sequence of interest. Further, a transformation vector can include sequences for site-specific recombination such as but not limited to lox sites on which the Cre recombinase acts.

In addition to the promoters provided herein, one skilled in the art would know various promoters, introns, enhancers, transit peptides, targeting signal sequences, 5' and 3' untranslated regions (UTRs), IRES, 2A sequences, and terminator sequences, as well as other molecules involved in the regulation of gene expression that are useful in the design of effective expression vectors. In some embodiments, the expression vector will contain one or more enhancer elements. Enhancers are short regions of DNA that can bind trans-acting factors to enhance transcription levels. Although enhancers usually act in cis, an enhancer need not be particularly close to its target gene, and may sometimes not be located on the same chromosome. Enhancers can sometimes be located in introns.

In some examples, a gene or genes encoding enzymes that participate in the synthesis of a fatty acid product (e.g., a fatty acid, a fatty acid derivative, or a glycerolipid) is cloned into the vector as an expression cassette that includes a promoter as disclosed herein. The expression cassette may optionally include a transit peptide-encoding sequence for directing the expressed enzyme to the chloroplast or endoplasmic reticulum of transformed eukaryotic cells, an intron sequence, a sequence having a polyadenylation signal, etc. Additionally or alternatively, a vector is provided comprising an expression cassette as described herein, wherein the vector further comprises one or more of: a selectable marker gene, an origin of replication, and one or more sequences for promoting integration of the expression cassette into the host genome. Additionally or alternatively, a vector is provided comprising an isolated or recombinant nucleic acid molecule as described herein, wherein the isolated nucleic acid molecule is operably linked to a nucleic acid sequence encoding a selectable marker or a reporter protein, such as, for example, any described herein. In a particular embodiment, the vector further comprises one or more of: an origin of replication, one or more sequences for promoting integration of the expression cassette into the host genome, a sequence as reported herein that comprises a terminator, or an additional gene, wherein the additional gene encodes an antisense RNA, a microRNA, an shRNA, a ribozyme, structural protein, an enzyme, a transcription factor, or a transporter.

E. Chloroplast Transit Peptide

In a further aspect, provided herein is a nucleic acid molecule that comprises a nucleotide sequence encoding a chloroplast transit peptide, where the nucleic acid molecule that comprises a nucleotide sequence encoding a chloroplast transit peptide has at least 80%, at least 85%, at least 90%, or at least 95% sequence identity to SEQ ID NO:36 or a functional fragment thereof. The chloroplast transit peptide can direct a polypeptide to which it is operably linked to the stroma of a chloroplast, such as the chloroplast of a microalga. The nucleotide sequence encoding a chloroplast transit peptide as provided herein can be operably linked to a polypeptide-encoding nucleotide sequence such that when the chloroplast transit peptide-polypeptide construct is expressed in a photosynthetic eukaryotic cell, the synthesized polypeptide is localized to the chloroplast of the cell.

The photosynthetic eukaryotic cell can be a plant or algal cell, and in some examples is a microalgal cell, such as a cell of any microalga disclosed herein. In certain examples, the microalgal cell is a nucleic acid molecule that comprises a nucleotide sequence encoding a chloroplast transit peptide having at least 80%, at least 85%, at least 90%, or at least 95% sequence identity to SEQ ID NO:36, operably linked to a nucleotide sequence encoding a polypeptide of interest. The polypeptide of interest can be any polypeptide, and can be, without limitation: a metabolic enzyme; a polypeptide that participates in light harvesting or electron transport; a transcriptional regulator; a translational regulator; a transporter; an NADH or NADPH-forming reductase; a chaperonin or protein that participates in protein or protein complex assembly or membrane assembly; a selectable marker; a reporter gene; etc. A construct that includes a nucleic acid molecule encoding a transit peptide as provided herein operably linked to a nucleotide sequence encoding a protein of interest can be introduced into a photosynthetic eukaryotic cell, such as a plant or alga cell, including an algal cell belonging to any of the taxonomic groups provided herein, and the photosynthetic eukaryotic cell can be subjected to conditions under which the construct is expressed, such that the polypeptide of interest is synthesized and localized to the chloroplast of the photosynthetic eukaryotic cell.

F. Transformation Methods

The present invention also provides transformation methods in which a eukaryotic cell is transformed with an expression vector as described herein. The methods comprise introducing an expression vector as provided herein that includes at least one promoter as provided herein and then selecting for a transformant. The expression vector may be introduced by many methods familiar to those skilled in the art including, as non-limiting examples: natural DNA uptake (Chung et al. (1998) *FEMS Microbiol. Lett.* 164:353-61); conjugation (Wolk et al. (1984) *Proc. Nat'l. Acad. Sci. USA* 81:1561-65); transduction; glass bead transformation (Kindle et al. (1989) *J. Cell Biol.* 109:2589-601); silicon carbide whisker transformation (Dunahay et al. (1997) *Methods Mol. Biol.* (1997) 62:503-09); biolistics (Dawson et al. (1997) *Curr. Microbiol.* 35:356-62); electroporation (Kjaerulff et al. (1994) *Photosynth. Res.* 41:277-83); laser-mediated transformation; or incubation with DNA in the presence of or after pre-treatment with any of poly(amidoamine) dendrimers (Pasupathy et al. (2008) *Biotechnol. J.* 3:1078-82), polyethylene glycol (Ohnuma et al. (2008) *Plant Cell Physiol.* 49:117-20), cationic lipids (Muradawa et al. (2008) *J. Biosci. Bioeng.* 105: 77-80), dextran, calcium phosphate, or calcium chloride (Mendez-Alvarez et al. (1994) *J. Bacteriol.* 176:7395-97), optionally after treatment of the cells with cell wall-degrading enzymes (Perrone et al. (1998) *Mol. Biol. Cell* 9:3351-65). *Agrobacterium*-mediated transformation can also be performed on algal cells, for example after removing or wounding the algal cell wall (e.g., WO 2000/62601). Biolistic methods have been shown to be successful for transformation of the chloroplasts of plant and eukaryotic algal species (see, e.g., WO 2007/133558, incorporated by reference in its entirety). When transforming chloroplasts, it can be useful to codon-optimize the gene of interest for expression in chloroplasts (see, e.g., WO 2011/034863, incorporated by reference in its entirety).

The eukaryotic cell transformed can be, for example, a fungal, heterokont, algal, or plant cell. For example, the eukaryotic cell transformed using an expression vector as provided herein can be an algal cell, such as a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria,* and *Volvox*. For example, the eukaryotic cell transformed using the methods provided herein can optionally be a species of *Tetraselmis*, such as *Tetraselmis alacris, T. apiculata, T. ascus, T. astigmatica, T. chuii, T. convolutae, T. cordiformis, T. desikacharyl, T. gracilis, T. hazeni, T. impellucida, T. inconspicua, T. levis, T. maculate, T. marina, T. micropapillata, T. rubens, T. striata, T. suecica, T. tetrabrachia, T. tetrathele, T. verrucosa,* or *T. wettsteinii*.

In further examples, the eukaryotic cell can be an alga of the class Chlorophyceae, Trebouxiophyceae, or Prasinophyceae.

In some examples, a *Tetraselmis* cell is transformed by electroporation or particle bombardment. The expression vector used to transform the host cell may encode, for a selectable marker, a ble gene conferring bleomycin resistance, a polypeptide, or a functional RNA.

Additionally or alternatively, a *Tetraselmis* cell is transformed by a biolistic method. For example, the transformation may be achieved by use of a gene gun. By way of example, the gene gun may employ a rupture disc of 1100 rps, of 1350 rps, of 1550 rps, of 1800 rps, or of 2000 rps. A biolistic transformation of the present invention may involve any amount of DNA coated particles per bombardment; for example, a biolistic transformation method of the present invention may employ 500 µg, 1 mg, 2 mg, or 3 mg of DNA coated particles per bombardment.

The distance between a microcarrier and a plate in a biolistic transformation method of the present invention may vary according to the construct being transformed into a cell and the cells; for example the distance may be approximately 3 cm, approximately 4 cm, approximately 5 cm, approximately 6 cm, approximately 7 cm, approximately 8 cm, or even approximately 9 cm. A macrocarrier used in a biolistic method of the present invention may be in either the top position or bottom position, depending on the construct being transformed into a cell and the cells. DNA used in a biolistic method of the present invention may be linearized by restriction enzyme digest or may be circular supercoiled plasmid DNA, depending on the construct being transformed into a cell and the cells. Cells grown for use in a biolistic method of the present invention may be grown in a variety of culture conditions; for example, cells destined for bombardment in a biolistic method of the present invention may be grown in PM024 liquid media or on PM024 agar plates for 2 days prior to bombardment. Cells used in a biolistic method of the present invention may be in different phases of a 14:10 diel cycle; for example, cells may be in either a light phase or dark phase, depending on the construct being transformed into a cell and the cells. A variety of antibiotic concentrations may be used to select transformants after transformation by a biolistic method of the present invention. One skilled in the art will recognize that these parameters are all subject to routine optimization involving only limited experimentation.

G. Culture

Eukaryotic host cells, such as any of the cells disclosed hereinabove, transformed with the expression vectors are also provided herein. Transformed algal cell cultures can be diluted, plated on agar, and allowed to grow until isolated colonies can be selected for further propagation as clonal strains.

Therefore, in one embodiment a eukaryotic cell is provided comprising an isolated or recombinant nucleic acid molecule as described herein or an expression cassette as described herein, or a vector as described herein.

Algae can be cultured phototrophically, in the absence of a fixed carbon source. Additionally or alternatively algae can be cultured mixotrophically, where the cultures are supplied with light for at least part of the day, and also supplied with a reduced carbon source, such as a sugar (e.g., glucose, fructose, galactose, mannose, rhamnose, arabinose, xylose, lactose, sucrose, maltose), an organic acid (e.g., acetate, citrate, succinate), or glycerol. The photosynthetic organism can be grown mixotrophically for a period of time, followed by a period of phototrophic growth, or vice versa.

Media for phototrophic or mixotrophic growth of algae are known in the art, and media can be optimized to enhance growth or production of fatty acid products for a particular species. Artificial light sources can be used as the sole light source or to enhance or extend natural light.

Growth of algae can be in open areas, such as, for example, ponds, canals, channels, raceways, or tanks, or can be in bioreactors. Bioreactors are preferred for mixotrophic growth, and can also be used for phototrophic growth. The bioreactors can be of any sizes and form, and can include inlets for providing nutrients, additives, or gases, such as but not limited to air or $CO_2$. A bioreactor preferably also has an outlet for sampling of the culture. A bioreactor can be configured such that the algal culture is mixed during the growth period, for example, by stirring, rocking, shaking, inverting, bubbling of gases through the culture, etc. Outdoor ponds, raceways, tanks, canals, etc. can also be designed for mixing of cultures through, for example, paddles, pumps, hoses or jets for circulation of the culture media, or tubes, hoses or inlets for supplying air or $CO_2$ to the culture.

H. Further Embodiments

Embodiment 1

An isolated DNA molecule comprising a sequence selected from the group consisting of a nucleotide sequence having at least 80% identity to at least 100, at least 200, at least 300, at least 400, or at least 500 contiguous nucleotides of SEQ ID NO:1; a nucleotide sequence having at least 80% identity to at least 100, at least 200, at least 300, at least 400, or at least 500 contiguous nucleotides of SEQ ID NO:2; a nucleotide sequence having at least 80% identity to at least 100, at least 200, at least 300, at least 400, or at least 500, contiguous nucleotides of SEQ ID NO:3; a nucleotide sequence having at least 80% identity to at least 100 at least 200, at least 300, at least 400, or at least 500 contiguous nucleotides of SEQ ID NO:4; a nucleotide sequence having at least 80% identity to at least 100, at least 200, at least 300, at least 400, or at least 500 contiguous nucleotides of SEQ ID NO:5; a nucleotide sequence having at least 80% identity to at least 100, at least 200, at least 300, at least 400, or at least 500 contiguous nucleotides of SEQ ID NO:6; a nucleotide sequence having at least 80% identity to at least 100, at least 200, at least 300, at least 400, or at least 500 contiguous nucleotides of SEQ ID NO:7; and a nucleotide sequence having at least 80% identity to at least 100, at least 200, at least 300, at least 400, or at least 500 contiguous nucleotides of SEQ ID NO:8.

Embodiment 2

The isolated or recombinant nucleic acid molecule of Embodiment 1, wherein at least one of the following are satisfied:

the nucleic acid molecule has promoter activity in a eukaryotic cell, preferably an algal cell or heterokont cell;

the isolated nucleic acid molecule has at least 80%, at least 85%, at least 90%, at least 95%, at least 96%, at least 97%, at least 98%, at least 99%, or about 100% identity to at least 600, at least 700, or about 716 contiguous nucleotides of SEQ ID NO:1;

the isolated nucleic acid molecule has at least 80%, at least 85%, at least 90%, at least 95%, at least 96%, at least 97%, at least 98%, at least 99%, or about 100% identity to at least 600, at least 700, at least 800, at least 900, at least 1000, at least 1200, at least 1400, or about 1504 contiguous nucleotides of SEQ ID NO:2;

the isolated nucleic acid molecule has at least 80%, at least 85%, at least 90%, at least 95%, at least 96%, at least 97%, at least 98%, at least 99%, or about 100% identity to at least 600, at least 700, at least 800, at least 900, at least 1000, at least 1200, at least 1400, or about 1599 contiguous nucleotides of SEQ ID NO:3;

the isolated nucleic acid molecule has at least 80%, at least 85%, at least 90%, at least 95%, at least 96%, at least 97%, at least 98%, at least 99%, or about 100% identity to at least 600, at least 700, at least 800, or about 838 contiguous nucleotides of SEQ ID NO:4;

the isolated nucleic acid molecule has at least 80%, at least 85%, at least 90%, at least 95%, at least 96%, at least 97%, at least 98%, at least 99%, or about 100% identity to at least 600, at least 700, at least 800, at least 900, at least 1000, or about 1077 contiguous nucleotides of SEQ ID NO:5;

the isolated nucleic acid molecule has at least 80%, at least 85%, at least 90%, at least 95%, at least 96%, at least 97%, at least 98%, at least 99%, or about 100% identity to at least 600, at least 700, at least 800, at least 900, at least 1000, or about 1042 contiguous nucleotides of SEQ ID NO:6;

the isolated nucleic acid molecule has at least 80%, at least 85%, at least 90%, at least 95%, at least 96%, at least 97%, at least 98%, at least 99%, or about 100% identity to at least 600, at least 700, at least 800, at least 900, at least 950, or about 991 contiguous nucleotides of SEQ ID NO:7;

the isolated nucleic acid molecule has at least 80%, at least 85%, at least 90%, at least 95%, at least 96%, at least 97%, at least 98%, at least 99%, or about 100% identity to at least 600, at least 700, at least 800, at least 900, at least 950, or about 991 contiguous nucleotides of SEQ ID NO:8;

the isolated nucleic acid molecule comprises a constitutive promoter; and the isolated nucleic acid molecule comprises a promoter active in a eukaryotic cell in nutrient replete and nutrient deficient culture conditions.

Embodiment 3

A promoter comprising a nucleic acid sequence having at least 80%, at least 85%, at least 90%, at least 95%, at least 96%, at least 97%, at least 98%, at least 99%, or about 100% identity to at least 100, at least 200, at least 300, at least 400, or at least 500 contiguous nucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

Embodiment 4

The promoter according to Embodiment 3 wherein the promoter is constitutive.

Embodiment 5

An isolated DNA molecule comprising a sequence selected from the group consisting of a nucleotide sequence having at least 80% at least 85%, at least 90%, at least 95%, at least 96%, at least 97%, at least 98%, at least 99%, or about 100% identity to at least 100 contiguous nucleotides of SEQ ID NO:9; and a nucleotide sequence having at least 80%, at least 85%, at least 90%, at least 95%, at least 96%, at least 97%, at least 98%, at least 99%, or about 100% identity to at least 100 contiguous nucleotides of SEQ ID NO:10.

Embodiment 6

An isolated or recombinant nucleic acid molecule comprising a nucleotide sequence having at least 80%, at least 85%, at least 90%, at least 95%, at least 96%, at least 97%, at least 98%, at least 99%, or about 100% identity to at least 100 or at least 150 contiguous nucleotides of SEQ ID NO:9 or SEQ ID NO:10, optionally wherein at least one of the following are satisfied:

the isolated nucleic acid molecule has at least 80%, at least 85%, at least 90%, at least 95%, at least 96%, at least 97%, at least 98%, at least 99%, or about 100% identity to at least 200, at least 300, at least 400, at least 500, at least 600, at least 700, at least 800, at least 900, at least 950, or about 1011 contiguous nucleotides of SEQ ID NO:9;

the isolated nucleic acid molecule has at least 80%, at least 85%, at least 90%, at least 95%, at least 96%, at least 97%, at least 98%, at least 99%, or about 100% identity to at least 200, at least 300, at least 400, at least 500, at least 600, at least 700, at least 800, at least 900, at least 1000, at least 1200, or about 1223 contiguous nucleotides of SEQ ID NO:10;

wherein the isolated or recombinant nucleic acid molecule preferably comprises a terminator sequence.

Embodiment 7

An expression cassette comprising:
a promoter according to Embodiment 3; and
a heterologous gene encoding a polypeptide or a functional RNA sequence operably linked to the promoter.

Embodiment 8

An expression cassette comprising the isolated nucleic acid molecule of any of Embodiments 1-4, wherein:

a) the isolated nucleic acid molecule is operably linked to a gene encoding a polypeptide, optionally wherein the polypeptide is:

a protein associated with lipid biosynthesis, an acetyl-CoA carboxylase, a malonyl type 1 fatty acid synthase, a Type 2 fatty acid synthase subunit, a beta ketoacyl-ACP synthase, a malonyl-CoA-malonyl-ACP acyltransferase, an acyl-ACP thioesterase, an acyl-CoA thioesterase, a 4-hydroxybenzoyl thioesterase, an alcohol forming acyl reductase, a wax synthase, an aldehyde decarbonylase, a fatty acid decarboxylase, a lipase, a glyceraldehyde 3 phosphate dehydrogenase, an acyl-CoA synthetase, a phospholipid diacylglycerol acyltransferase, a glycerol 3 phosphate acyltransferase, a lysophosphatidic acid acyltransferase, a phosphatidic acid phosphatase, a diacyl glycerol acyltransferase, a polypeptide having lipolytic activity, a polypeptide that participates in photosynthesis, a chlorophyll binding light harvesting polypeptide, a photosynthetic reaction center polypeptide, an oxygen-evolving complex polypeptide, a cytochrome, a ferredoxin, a protein associated with carbon fixation, a ribulose bisphoshate carboxylase subunit, a carbonic anhydrase, a transporter protein, an ABC transporter, a FatB transporter, a dehydrogenase, an aldehyde dehydrogenase, a 2-hydroxyacid dehydrogenase, an isocitrate dehydrogenase, 6 phosphogluconate dehydrogenase, glucose 6 phosphate dehydrogenase; a transcription factor, a protein involved in cell signaling, a kinase, or a G protein; or (b) the isolated nucleic acid molecule is operably linked to a gene encoding a functional RNA, optionally wherein the functional RNA is an antisense RNA, a small hairpin RNA, a microRNA, an antisense RNA, a siRNA, a piRNA, or a ribozyme;

wherein the expression cassette optionally further comprises a nucleotide sequence according to Embodiment 6; wherein the nucleotide sequence of Embodiment 6 comprises a terminator, further wherein the terminator is operably linked to the heterologous gene coding sequence and/or the terminator is downstream of the heterologous gene coding sequence.

Embodiment 9

A vector comprising an expression cassette according to Embodiment 8, wherein the expression vector further comprises one or more of: an origin of replication; and one or more sequences for promoting integration of the expression cassette into the host genome, or a selectable marker or reporter gene; optionally wherein the selectable marker gene is selected from the group consisting of a gene conferring resistance to an antibiotic, a gene conferring resistance to an herbicide, a gene encoding acetyl CoA carboxylase (AC-Case), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS (aroA), a gene encoding a non-class I/II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acetyl transferase, a gene encoding phytoene desaturase, a gene encoding prenyl transferase, a gene encoding protoporphyrin oxidase, a gene encoding superoxide dismutase, arg7, his3, hisD, hisG, manA, nit1, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene; an R-locus gene, a tyrosinase gene, lacZ, an alkaline phosphatase gene, an α-amylase gene, a horseradish peroxidase gene, an α-galactosidase gene, a luciferin/luciferase gene, a beta-glucuronidase gene (GUS), and a gene encoding a fluorescent protein.

Embodiment 10

A method for transforming a eukaryotic cell comprising:
introducing a vector according to Embodiment 9 into the eukaryotic cell; and
selecting for a transformed eukaryotic cell, preferably wherein the eukaryotic host cell is a fungal, algal, heterokont, or plant host cell optionally wherein the eukaryotic host cell is a species of Bacillariophyceae (diatoms), Bolidomonas, Chlorophyceae (green algae), Chrysophyceae (golden algae), Cyanophyceae (cyanobacteria), Eustigmatophyceae (picoplankton), Glaucocystophytes, Pelagophyceae, Bolidophyceae, Prasinophyceae (pico-plankton), Raphidophyceae, Rhodophyceae (red algae), Synurophyceae and Xanthophyceae (yellow-green algae), *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria,* or *Volvox.*

Embodiment 11

The method according to Embodiment 10, wherein the vector is introduced by a biolistic procedure, optionally wherein at least about 300 psi of pressure is used to impel biolistic microcarriers coated with vector DNA into the eukaryotic cell.

Embodiment 12

A method for co-transforming a eukaryotic cell comprising:
introducing an expression cassette according to Embodiment 8 and a nucleic acid sequence encoding a selectable marker into the eukaryotic cell; and
selecting for the presence of the selectable marker in a transformed eukaryotic cell to provide a eukaryotic cell transformed with the expression cassette, optionally wherein the eukaryotic cell is an algal cell, optionally wherein the selectable marker gene is operably linked to a promoter according to Embodiment 3, optionally wherein the selectable marker gene is selected from the group consisting of a gene conferring resistance to an antibiotic, a gene conferring resistance to an herbicide, a gene encoding acetyl CoA carboxylase (AC-Case), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS (aroA), a gene encoding a non-class I/II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acetyl transferase, a gene encoding phytoene desaturase, a gene encoding prenyl transferase, a gene encoding protoporphyrin oxidase, a gene encoding superoxide dismutase, arg7, his3, hisD, hisG, manA, nit1, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene; and an R-locus gene.

Embodiment 13

A method according to Embodiment 12, wherein the algal cell is from a species selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris,*

*Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*.

Embodiment 14

A eukaryotic host cell comprising an isolated or recombinant nucleic acid molecule, expression cassette, or vector of any of Embodiments 7-9, wherein the eukaryotic host cell is optionally a microalgal cell, optionally a species of wherein the eukaryotic cell is an algal cell, optionally, a species of Bacillariophyceae, Bolidomonas, Chlorophyceae, Chrysophyceae, Eustigmatophyceae, Glaucocystophytes, Pelagophyceae, Bolidophyceae, Prasinophyceae, Raphidophyceae, Rhodophyceae (red algae), Synurophyceae or Xanthophyceae (yellow-green algae), or of a genus selected from the group consisting of: *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*.

Embodiment 15

A nucleic acid molecule that comprises a nucleotide sequence encoding a chloroplast transit peptide, where the nucleic acid molecule that comprises a nucleotide sequence encoding a chloroplast transit peptide has at least 80%, at least 85%, at least 90%, or at least 95% identity to SEQ ID NO:36 or a functional fragment thereof.

Embodiment 16

The nucleic acid molecule of Embodiment 15, wherein the sequence encoding a chloroplast transit peptide is operably linked to a nucleic acid sequence encoding a polypeptide that is localized to the chloroplast of the cell when the nucleic acid molecule is expressed in a eukaryotic photosynthetic cell.

Embodiment 17

A eukaryotic photosynthetic cell comprising the nucleic acid molecule of Embodiment 15 or 16, wherein the eukaryotic photosynthetic cell is preferably an algal cell, for example an algal cell of the class Chlorophyceae, Prasinophyceae, or Trebouxiophyceae.

EXAMPLES

The following examples are merely illustrative, and do not limit this disclosure in any way.

Example 1

Strains and Media

*Tetraselmis* is a green alga in the Prasinophyceae class (Chlorophyte phylum). A strain of *Tetraselmis*, designated WT-105, was isolated from an environmental sample from South Laguna Madre, Tex. Strain P-925 is a classically improved derivative of WT-105 with increased lipid productivity traits.

Media used for the growth of *Tetraselmis* included the following:

PM024: 35 g/L Instant Ocean Salts (Aquatic Eco Systems, Apopka, Fla.), 10× Guillard's F/2 marine water enrichment solution (from 50× stock from Sigma-Aldrich, St. Louis, Mo., cat. No. G0154; final concentrations of components in media: 8.825 mM Sodium nitrate; 320 µM Sodium phosphate monobasic; 205 nM biotin; 420 nM Cobalt chloride.$6H_2O$; 400 nM Cupric sulfate.$5H_2O$; 116.5 µM Ferric chloride.$6H_2O$; 117.13 µM Disodium EDTA.$2H_2O$; 9.095 µM Manganese chloride.$4H_2O$; 248 nM Sodium molybdate.$2H_2O$; 2.965 µM Thiamine.HCl; 37 nM Vitamin $B_{12}$; 765 nM Zinc sulfate.$7H_2O$).

PM032 is filtered seawater to which 1.3 mL per liter (of final media volume) PROLINE® F/2 Algae Feed Part A (Aquatic Eco-Systems) and 1.3 ml/L PROLINE® F/2 Algae Feed Part B (Aquatic Eco-Systems) have been added. The final media composition includes 8.8 mM $NaNO_3$, 0.361 mM $NaH_2PO_4.H_2O$, 10× the Guillard's F/2 medium trace metal concentration, and 10× the Guillard's F/2 medium trace vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

Nutrient Replete Media: 35 g/L Instant Ocean Salts, 0.5 g/L $NaHCO_3$, 10 mM MOPS pH 8, 7 mM $NH_4Cl$, 140 µM $KH_2PO_4$; final concentration of trace elements and vitamins: (400 µM $MgSO_4.7H_2O$; 48 µM $CaCl_2.2H_2O$; 162 µM $H_3BO_3$; 2 µM $NaVO_3$; 47 µM $FeCl_3.6H_2O$; 47 µM $Na_2EDTA.2H_2O$; 3.6 µM $MnCl_2.4H_2O$; 304 nM $ZnSO_4.7H_2O$; 168 nM $CoCl_2.6H_2O$; 156 nM $CuSO_4.5H_2O$; 104 nM $Na_2MoO_4.2H_2O$; 1.2 µM Thiamine.HCl; 8 nM Biotin; 1.5 nM Cyanocobalamine).

Nitrogen Deficient (a.k.a. N minus) Media: 35 g/L Instant Ocean Salts, 0.5 g/L $NaHCO_3$, 10 mM MOPS pH 8, 140 µM $KH_2PO_4$; final concentration of trace elements and vitamins: (400 µM $MgSO_4.7H_2O$; 48 µM $CaCl_2.2H_2O$; 162 µM $H_3BO_3$; 2 µM $NaVO_3$; 47 µM $FeCl_3.6H_2O$; 47 µM $Na_2EDTA.2H_2O$; 3.6 µM $MnCl_2.4H_2O$; 304 nM $ZnSO_4.7H_2O$; 168 nM $CoCl_2.6H_2O$; 156 nM $CuSO_4.5H_2O$; 104 nM $Na_2MoO_4.2H_2O$; 1.2 µM Thiamine.HCl; 8 nM Biotin; 1.5 nM Cyanocobalamine).

Phosphate Deficient Media 1: 35 g/L Instant Ocean Salts, 500 mg/L $NaHCO_3$, 10 mM MOPS pH 8, 7 mM $NH_4Cl$, 35 µM $KH_2PO_4$; final concentration of trace elements and vitamins: (400 µM $MgSO_4.7H_2O$; 48 µM $CaCl_2.2H_2O$; 162 µM $H_3BO_3$; 2 µM $NaVO_3$; 47 µM $FeCl_3.6H_2O$; 47 µM $Na_2EDTA.2H_2O$; 3.6 µM $MnCl_2.4H_2O$; 304 nM $ZnSO_4.7H_2O$; 168 nM $CoCl_2.6H_2O$; 156 nM $CuSO_4.5H_2O$;

104 nM Na$_2$MoO$_4$.2H$_2$O; 1.2 µM Thiamine.HCl; 8 nM Biotin; 1.5 nM Cyanocobalamine).

Phosphate Deficient Media 2: 35 g/L Instant Ocean Salts, 500 mg/L NaHCO$_3$, 10 mM MOPS pH 8, 7 mM NH$_4$Cl, 18 µM KH$_2$PO$_4$; final concentration of trace elements and vitamins: (400 µM MgSO$_4$.7H$_2$O; 48 µM CaCl$_2$.2H$_2$O; 162 µM H$_3$BO$_3$; 2 µM NaVO$_3$; 47 µM FeCl$_3$.6H$_2$O; 47 µM Na$_2$EDTA.2H$_2$O; 3.6 µM MnCl$_2$.4H$_2$O; 304 nM ZnSO$_4$.7H$_2$O; 168 nM CoCl$_2$.6H$_2$O; 156 nM CuSO$_4$.5H$_2$O; 104 nM Na$_2$MoO$_4$.2H$_2$O; 1.2 µM Thiamine.HCl; 8 nM Biotin; 1.5 nM Cyanocobalamine).

Phosphate Deficient Media 3: 35 g/L Instant Ocean Salts, 500 mg/L NaHCO$_3$, 10 mM MOPS pH 8, 7 mM NH$_4$Cl, 10 µM KH$_2$PO$_4$; final concentration of trace elements and vitamins: (400 µM MgSO$_4$.7H$_2$O; 48 µM CaCl$_2$.2H$_2$O; 162 µM H$_3$BO$_3$; 2 µM NaVO$_3$; 47 µM FeCl$_3$.6H$_2$O; 47 µM Na$_2$EDTA.2H$_2$O; 3.6 µM MnCl$_2$.4H$_2$O; 304 nM ZnSO$_4$.7H$_2$O; 168 nM CoCl$_2$.6H$_2$O; 156 nM CuSO$_4$.5H$_2$O; 104 nM Na$_2$MoO$_4$.2H$_2$O; 1.2 µM Thiamine.HCl; 8 nM Biotin; 1.5 nM Cyanocobalamine).

Stock cultures were cultured in shake flasks with 50 mL PM024 containing 250 µg/mL ZEOCIN™ phleomycin D1 antibiotic ("Zeocin") when appropriate. Shake flasks were cultivated at 25° C., 100 rpm, 60 µE constant light, 1% CO$_2$.

Example 2

Tetraselmis Transformation Vector Design and Synthesis

Vector p05320 (FIG. 1), containing the Streptoalloteichus hindustanus (Sh) ble gene conferring Zeocin-resistance and codon-optimized for expression in Chlamydomonas reinhardtii (SEQ ID NO:30) under the control of the WT-105 actin promoter fragment (SEQ ID NO:1) and WT-105 actin terminator fragment (SEQ ID NO:9), was assembled using the Gibson assembly method (Gibson et al. (2008) Science 319:1215-20).

Figure 2:
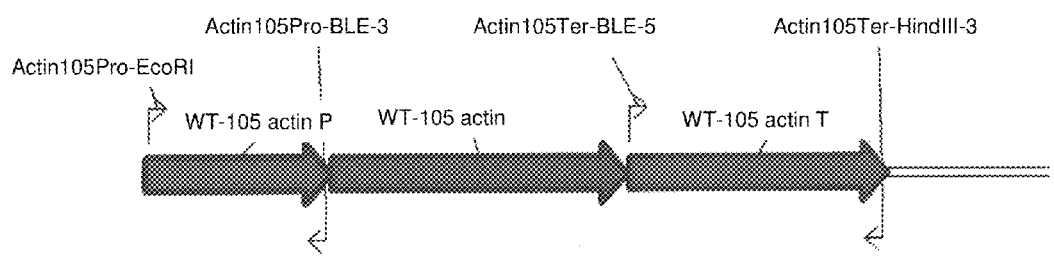
FIG. 2 is a diagram of the wild type parent (WT-105) genome sequence for the actin gene. Bent labeled arrows indicate primers used to amplify the upstream and downstream regions labeled "WT-105 actin P" and "WT-105 actin T". The actin open reading frame is shown labeled as "WT-105 actin".

The WT-105 actin gene (FIG. 2) was identified based on genome sequencing and homology to actin genes of other organisms. The sequence from 1-713 bp upstream of the actin gene start codon (SEQ ID NO:1) was amplified as the actin gene promoter fragment and the sequence from 1-1000 bp downstream of the actin gene termination codon (SEQ ID NO: 9) was amplified as the actin gene terminator fragment to direct expression of the ble gene of plasmid p05320 (FIG. 1). After PCR amplification using the primers in Table 2 and WT-105 genomic DNA as the template, a 713 bp upstream region (actin promoter fragment; SEQ ID NO:1) and 1 kbp downstream region (actin terminator fragment; SEQ ID NO:9) were assembled with the PCR-amplified Sh ble gene (SEQ ID NO:30) and cloned into a plasmid containing the pUC19 backbone between HindIII and EcoRI restriction sites, forming the plasmid p05320 (FIG. 1; SEQ ID NO:29). The Sh ble coding sequence, codon-optimized for Chlamydomonas, (SEQ ID NO:30), was PCR amplified with primers BLE-ActinWT105-5 (SEQ ID NO:15) and BLE-ActinWT105-3 (SEQ ID NO:16) (Table 2).

TABLE 2

Primers for p05320 construction

| Primer name | Primer sequence | SEQ ID NO: |
|---|---|---|
| WT105ActinPro-EcoRI | 5'-aaacgacggccagtgaattccgtttctgatcctgggcctt | 11 |
| WT105ActinPro-BLE-3 | 5'-gacgtcagcttggccaacatggtgcctttcttcgtaagag | 12 |
| WT105ActinTER-BLE-5 | 5'-tcgccgaagagcaggattaagcaagcgctgtgcaatcaa | 13 |
| WT105ActinTER-HindIII | 5'-accatgattacgccaagcttccattggtggttggagccct | 14 |
| BLE-ActinWT105-5 | 5'-ctcttacgaagaaaggcaccatgttggccaagctgacgtc | 15 |
| BLE-ActinWT105-3 | 5'-ttgattgcacagcgcttgcttaatcctgctcttcggcga | 16 |

The p05320 construct also contained a gene coding for Turbo-GFP (Evrogen, Moscow, Russia), codon-optimized for expression in WT-105 based on a codon table derived from an analysis of over 100000 WT-105 genes. This Turbo-GFP coding sequence was flanked by two Chlamydomonas reinhardtii regulatory sequences: the promoter fragment from the C. reinhardtii actin gene (GenBank accession #D50838, SEQ ID NO:31) and the terminator fragment from the C. reinhardtii psaD gene (GenBank accession #XM_001697670, SEQ ID NO:32). After PCR amplification using the primers below (Table 3), the C. reinhardtii actin gene 713 bp upstream region (promoter fragment) and C. reinhardtii psaD gene 1 kbp downstream region (terminator fragment) were assembled with the PCR-amplified GFP by the Gibson assembly method and cloned into a PciI restriction site. The Pontellina plumata GFP coding sequence was PCR amplified with primers GFP-ActinWT105-5 (SEQ ID NO:21) and GFP-ActinWT105-3 (SEQ ID NO:22) (Table 3).

TABLE 3

Primers for p05322 construction

| Primer name | Primer sequence | SEQ ID NO: |
|---|---|---|
| WT105ActinPro-PciI | 5'-gctggccttttgctcacatgtcgtttctgatcctgggcct | 17 |
| WT105ActinPro-GFP-3 | 5'-cccggattcgtccgactccatggtgcctttcttcgtaaga | 18 |

TABLE 3-continued

Primers for p05322 construction

| Primer name | Primer sequence | SEQ ID NO: |
|---|---|---|
| WT105ActinTER-GFP-5 | 5'-ccgacgctggagaagagtaaagcaagcgctgtgcaatcaa | 19 |
| WT105ActinTER-PciI | 5'-taacgcaggaaagaacatgtccaaatggtcgtgtttggtg | 20 |
| GFP-ActinWT105-5 | 5'-tcttacgaagaaaggcaccatggagtcggacgaatccggg | 21 |
| GFP-ActinWT105-3 | 5'-ttgattgcacagcgcttgctttactcttctccagcgtcgg | 22 |

Example 3

Transformation of WT-105

To introduce the p05320 plasmid into cells, WT-105 cells were harvested in late log phase and bombarded with ScaI-linearized p05320 coated on gold beads. Gold microcarriers used for bombardment of algal cells using the PDS-1000/He Particle Delivery System were S550d DNADEL™ Gold Carrier Particles (Seashell Technology). The gold particles were sonicated briefly to dissociate any aggregates prior to formulation and diluted into binding buffer to yield a final concentration of 30 mg/mL. The linearized DNA (overnight restriction enzyme digested and phenol/chloroform extracted) was added at a ratio of 2-5 µg DNA per 1 mg gold and vortexed briefly. An equal volume of precipitation buffer was added, vortexed briefly, and incubated for 3 minutes at room temperature. The DNA coated particles were centrifuged at 10 krpm in Eppendorf microfuge tubes for 10 seconds. Pelleted gold particles were washed with 500 µL of cold 100% ethanol once and resuspended in cold 100% ethanol to reach 1 mg particles per 10 µL. Prior to particle bombardment, the DNA-coated particles were sonicated for 1 minute to disperse any aggregates.

Equipment set up and detailed operation procedures were according to the BIOLISTIC® PDS-1000/He Particle Delivery System User manual (available at http://biorad.com/webroot/web/pdf/lsr/literature/Bulletin_9075.pdf). Late-log phase cells were collected by centrifugation at 2000×g for 10 minutes at 25° C. and 1×10$^7$ cells were plated on PM024 agar covering the center 5 cm of the plate. Bombardment was performed with a BioRad PDS-1000 unit at 1800 psi with a chamber vacuum of 10 Hg, with the disk positioned at 6 cm distance from the cells.

Cells were spread on PM024 agar plates containing 250 µg/mL Zeocin and grown under constant light for three weeks at room temperature, after which ten colonies were patched on a second PM024 (containing 250 µg/mL Zeocin) agar plate. No colonies were detected on the control plates (bombardment without plasmid). Five of the ten isolates patched from the initial selection plate grew on the second selection plate (isolates C2, C4, C6, C8, and C10) and were transferred again to new selection plates. All five grew, and were screened by colony PCR for the presence of the ble gene and the endogenous Na$^+$/H$^+$ ATPase gene. The five isolates that did not grow, i.e. that were only transiently resistant to the antibiotic, may have expressed the Ble protein from an un-integrated DNA which was subsequently lost.

Colony PCR for p05320 *Tetraselmis* Transformants:

Cells were picked off of patch plates and placed into 100 µL of TE buffer. Samples were incubated at 98° C. for 10 minutes to disrupt the cell wall and membrane, and then cell debris was removed by centrifugation. A PCR reaction was set up using the supernatant as the DNA template to amplify the Sh ble gene. The p05320 vector was used as a positive control. 10 µM of each of the primers LF-SGE5320F1 (SEQ ID NO:27) and BLEcodon3 (SEQ ID NO:28) were used to amplify a 645 bp fragment.

To verify the sensitivity of the PCR assay, an endogenous single copy gene was used as a positive control. To determine an appropriate single copy gene, protein sequences deduced from five publically available algal genomes (*Chlamydomonas reinhardtii, Ostreococcus lucimarinus, Ostreococcus taurii, Phaeodactylum tricornutum,* and *Thalassiosira pseudonana*) were clustered into families by homology. Genes were identified which had single protein per cluster and the Na$^+$/H$^+$ translocating ATPase gene was chosen from this group for use as an endogenous single-copy control gene. Primers NaHtransB5 (SEQ ID NO:25) and NaHtransC3 (SEQ ID NO:26) were designed to amplify a 670 bp fragment from the endogenous Na$^+$/H$^+$ ATPase gene. For the PCR reactions, 2× PHUSION® master PCR mix reagent mixture (New England Biolabs) was used with 200 nM of each of the primers and about 20 ng of template in a 25 µL reaction. The following PCR program was used: Step 1, 98° C. for 3 min.; Step 2, 98° C. for 30 sec.; Step 3, 58° C. for 30 sec.; Step 4, 72° C. for 1 min.; Cycle to Step 2, 35 more times; Step 5, 72° C. for 5 min.; and Step 6, hold at 4° C. 15 µL of each reaction product was loaded on a 1% agarose gel and separated at 100 V for 30 minutes.

Figure 3:
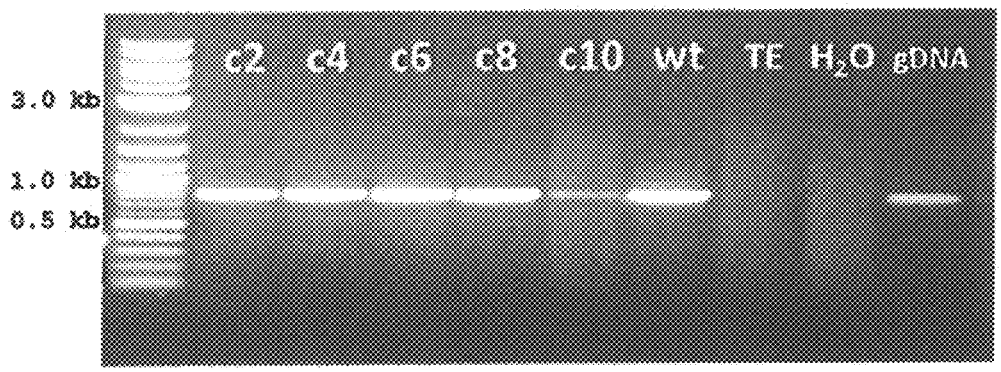
FIG. 3 is a colony PCR screen for *Tetraselmis* transformation. PCR was performed on colonies of the Zeocin-resistant isolates (C2-C10), the wild type parent (wt), Tris EDTA buffer (TE), water ($H_2O$), or genomic DNA from the wild type parent (gDNA). The $Na^+/H^+$ transporter (upper panel) is a likely single-copy endogenous gene that was used as a sensitivity control. The ble gene (lower panel) is present on the p05320 plasmid. A 2-log ladder (NEB, cat. no. N3200S) is included as a size standard.
Figure 3:
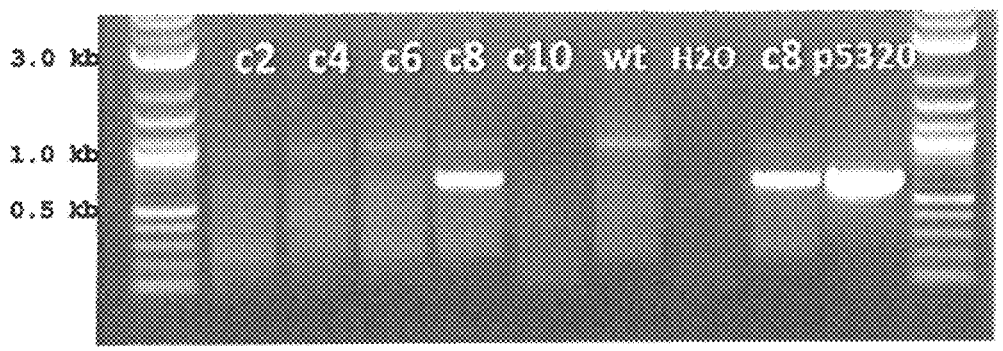

Colony PCR of the putative transformants showed, as expected, that the endogenous Na$^+$/H$^+$ ATPase gene was detected in all five Zeocin-resistant isolates and in the wild type cells (FIG. 3, upper panel), indicating that sufficient template was present. No bands were detected in the negative controls (water or TE buffer alone). The ble gene was detected only in isolate C8, which produced a band that co-migrated with the band amplified from the p05320 vector (FIG. 3, lower panel). The other four Zeocin-resistant isolates and wild type did not produce a band of the expected size. The C8 isolate was chosen for further analysis to determine whether the ble gene was integrated into the genome, and if the Ble protein was expressed.

To determine whether the ble gene in isolate C8 was integrated into the WT-105 genome, a Southern blot was performed using a digoxigenin-labeled PCR product amplified from the ble gene and restriction digested genomic DNA. Genomic DNA (5 µg) was restriction digested with either HindIII and BglII or KpnI and MfeI in a 50 µL reaction at 37° C. overnight. A positive control (Ble coding sequences) was prepared by PCR using the p05320 plasmid as a template. A 378 bp digoxigenin-labeled probe was synthesized as according to the user's manual (PCR DIG Probe Synthesis Kit; Cat 11 636 090 910; Roche), by PCR with the primers of Table 4 using the p05320 plasmid as a template.

TABLE 4

Primers for ble probe construction

| Primer name | Primer sequence | SEQ ID NO: |
|---|---|---|
| BLE-5 | 5'-atgttggccaagctgacgtc | 23 |
| BLE-3 | 5'-ttaatcctgctcttcggcga | 24 |

Electrophoresis was performed using a 0.7% agarose gel with 50 ng/mL ethidium bromide in 1× Tris-acetate-EDTA (TAE) at 80 volts for 5 hours. Restriction digested genomic DNA (50 µL) was loaded into each lane along with a size standard, DIG-labeled DNA Molecular Weight Marker II (Roche cat. no. 11 218 590 910). Once the gel electrophoresis was completed, the DNA was depurinated prior to transfer by submerging the gel in 250 mM HCl, with shaking at room temperature, until the bromophenol blue marker changed from blue to yellow (~10 minutes). The DNA in the gel was denatured by submerging the gel twice in denaturing solution (500 mM NaOH, 1.5 M NaCl) for 15 minutes each time, at room temperature, with gentle shaking. After rinsing in distilled water, the gel was submerged twice in neutralization buffer (500 mM Tris-HCl, pH 7.5; 1.5 M NaCl) for 15 minutes each time at room temperature. The gel was equilibrated for at least 10 minutes in 20×SSC. The DNA transfer was conducted by capillary transfer overnight onto a nylon membrane using 20×SSC. The damp nylon membrane was placed DNA side up on Whatman paper that had been soaked in 2×SSC and the membrane was placed into a crosslinker and exposed to 1.2 mJ for 5 minutes. The blot was prehybridized in pre-warmed (42° C.) Easy Hyb buffer (cat#11 603 558 001) and incubated at 42° C. for 30 minutes. 80 µL of probe was denatured at 100° C. for 5 minutes and cooled quickly on ice, then added to 10 mL of pre-warmed hybridization buffer. The hybridization was conducted at 45° C. overnight. The blot was washed twice in low stringency buffer (2×SSC, 0.1% SDS, 5 minutes each wash) at room temperature and washed twice in high stringency buffer (0.1×SSC, 0.1% SDS, 15 minutes each wash) at 68° C. The hybridization of the probe was detected by chemiluminescence using the DIG Wash and Block Buffer Set (Roche cat#11 585 762 001), and an anti-digoxigenin antibody with CDP-Star chemiluminescent substrate (Roche cat#11 685 627 001) according to the user's manual. The chemiluminescence signal was detected by using the MULTIIMAGE® II detection and imaging system (Alpha Innotech).

Figure 4:
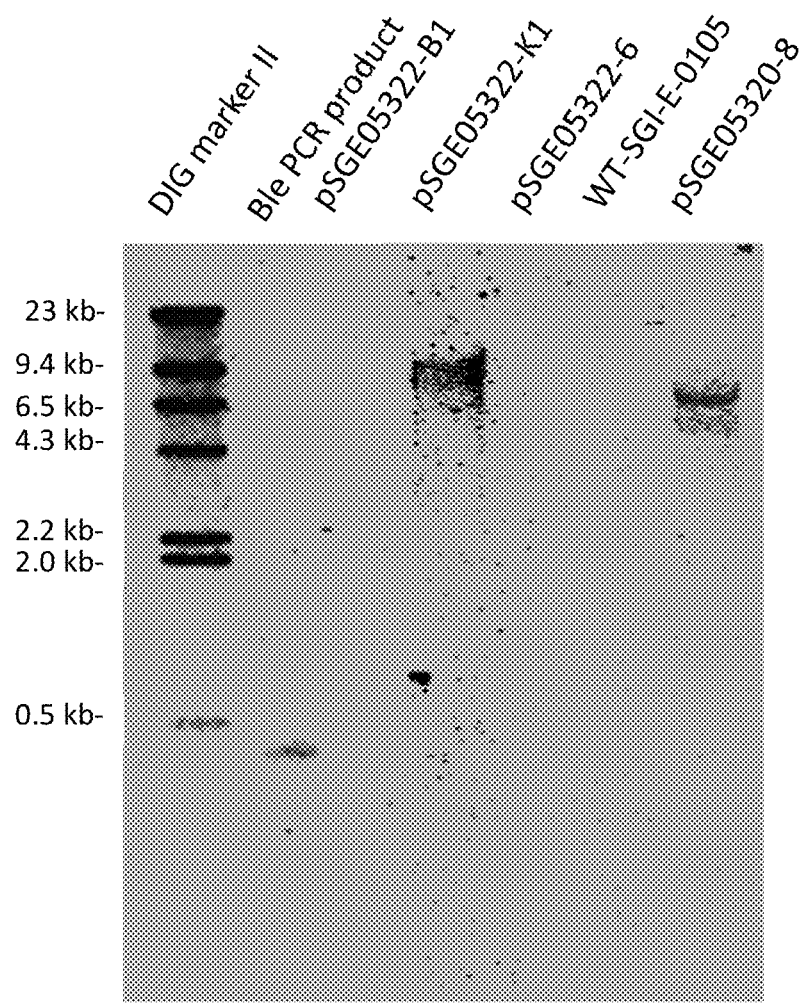
FIG. 4 is a Southern blot depicting results for putative PH-925 transformants obtained with PDS-1000 biolistics. 5 µg of HindIII/BglII digested genomic DNA was probed with a DIG-labeled PCR ble open reading frame product. Transformant strains are labeled according to the corresponding plasmid used in transformation and transformant colony number (e.g. p05322-B1). Different isolates carrying the same construct are designated with a dash plus a number (e.g., p05322-B1, -K1, etc.). The ble PCR product was added as a control. A DIG labeled marker was included with the corresponding sizes indicated on the left.
Figure 5:
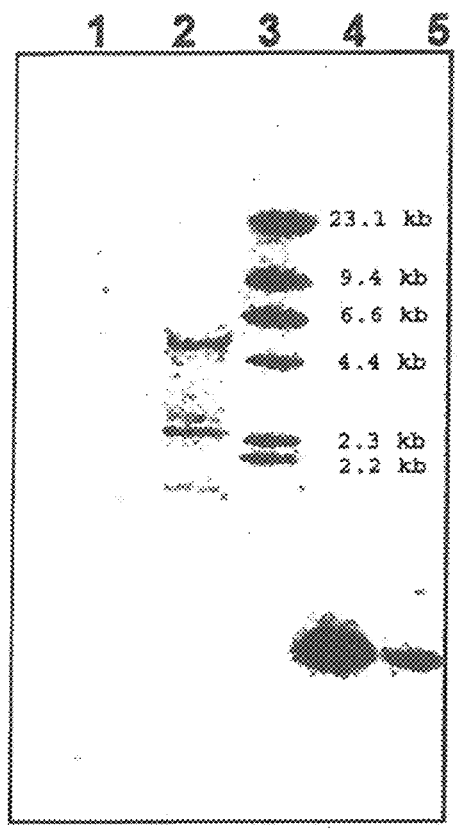
FIG. 5 is a Southern blot identifying integration of the ble gene in the *Tetraselmis* genome. An agarose gel was loaded with (1) genomic DNA from WT-105 and digested with KpnI/MfeI, (2) genomic DNA from the p05320-8 and digested with KpnI/MfeI, (3) DIG-labeled DNA Molecular Weight Marker II (DIG-Marker), and (lanes 4 & 5) two levels of PCR product amplified from p05320 (ble PCR positive control). The gel was blotted and the blot was probed with a DIG-labeled PCR product that hybridized to the ble gene.

As expected, no signal was detected in genomic DNA isolated from the wild type parent, whereas the anti-ble probe did detect bands in both digest of the C8 genomic DNA. FIG. 4 provides an image of the Southern blot of the HindIII and BglII digested genomic DNAs and FIG. 5 provides an image of the Southern blot of KpnI and MfeI digested genomic DNAs. Using DNA prepared from isolate C8, two strong bands were detected by the anti-ble probe, indicting the presence of the ble gene in the genomic DNA. Both of these bands were larger than the 1.5 kbp fragment expected from restriction digestion of p05320, although a faint band appears at this size. The larger size fragments may result from partial digestion of the genomic DNA, or from truncation of the integrated plasmid resulting in the loss of a restriction site. The presence of multiple bands indicates that the plasmid may be integrated in more than one chromosomal location.

To determine whether the ble gene was expressed and translated into protein, isolate C8 was also screened for the presence of Ble (bleomycin resistance protein). Shake flasks of 50 mL PM024 (250 µg/mL Zeocin) were inoculated with wild-type WT-105 or the p05320-8 WT-105 transformation isolate. Cultures were cultivated at 25° C., 100 rpm, 60 µE constant light, 1% $CO_2$. On day 7 post-inoculation, cell pellets were collected from 45 mL of each culture by centrifugation at 4000×g for 10 minutes and re-suspended in 1 mL PBS. The resuspended cultures were transferred into 2 mL Eppendorf tubes, each containing ~500 µL of 200 µm Zirconium beads. Samples were chilled on ice for 10 minutes before lysis by bead beating for 5 minutes. The supernatants of the lysed cultures were collected after centrifugation at 4000×g for 10 minutes, and pigments were solubilized by adding 4 volumes of methanol, 1 volume of chloroform, and 3 volumes of $H_2O$. After vortexing briefly, protein precipitates were pelleted by centrifugation at 15000×g for 2 minutes. The aqueous top layers were removed and pellets were washed twice with 4 volumes of methanol. The protein precipitates were re-dissolved in 200 µL 4×LOS sample loading buffer (Invitrogen, cat. #NP0007) containing 10% β-mercaptoethanol. 40 µL of each protein extract was loaded onto a 18% tris-glycine NOVEX® gel (Invitrogen, Carlsbad). Protein transfer was performed with iBlot (program #7, 7 minutes) (Invitrogen, Carlsbad). The membrane was incubated in blocking buffer (5% nonfat milk, TRIS-buffered saline with 1% Tween-20 (TBST)) for 1 hour before incubation in 25 mL of primary antibody (anti-BLE, InvivoGen, #ANTI-0010, 1:500) for 1 hour. The blot was washed five times with TBST for 5 minutes each wash and then incubated in secondary antibody (goat anti-rabbit IgG (H+L) HRP-conjugated, Bio-Rad cat. #170-6515) for 45 minutes. The blot was then washed 5 times with TBST for 5 minutes each wash before chemiluminescent signal was detected with chemiluminescent peroxidase substrate (CPS-1, Sigma-Aldrich, Saint Louis) using the MULTIIMAGE® II detection and imaging system (Alpha Innotech). The size standard was MAGIC-MARK™ XP Western Protein Standard (Invitrogen cat. # LC5602). The ble gene was cloned into an *E. coli* expression vector (p05406) and crude lysates were used as a positive control.

Figure 6:
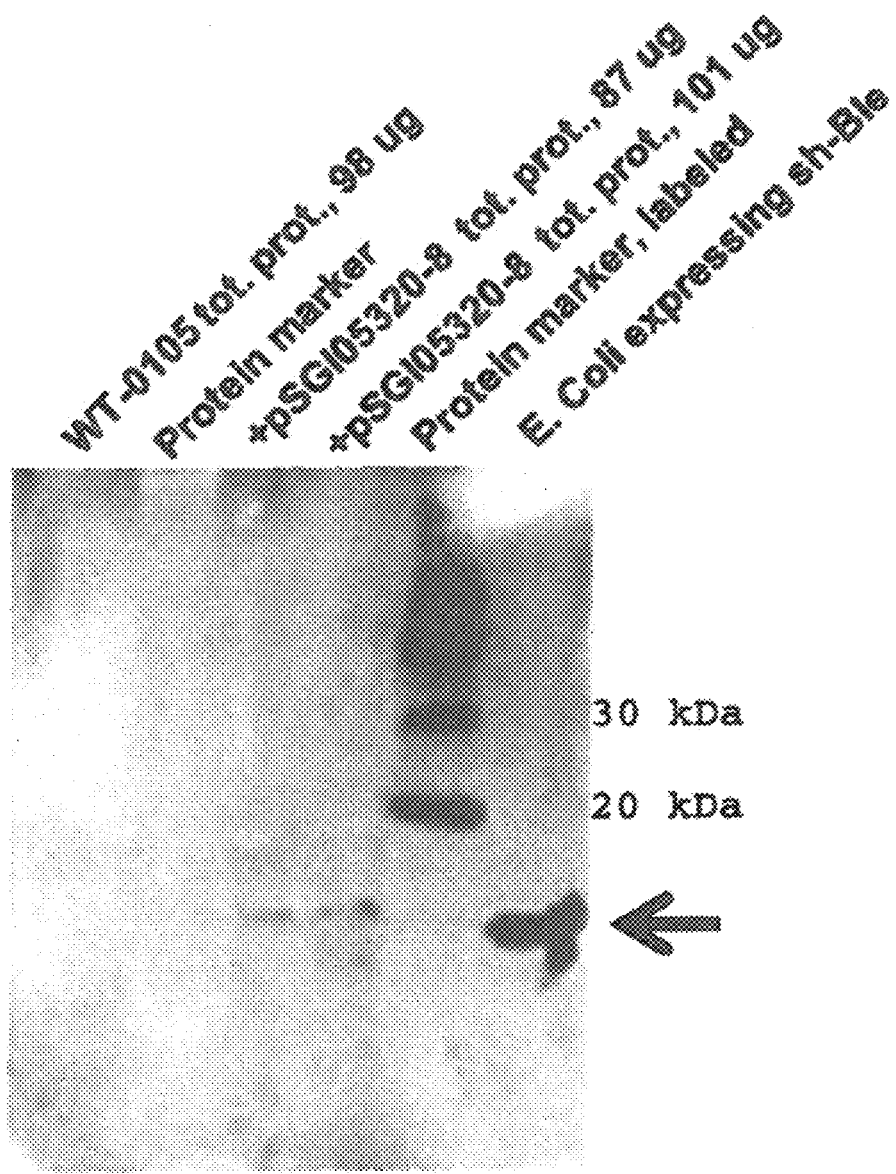
FIG. 6 is a western blot to detect expression of the Ble protein. An 18% gene was loaded with protein from the wild type parent (WT-105), the Magic Mark XP Western Protein Standard (Protein marker), protein from the pSGI05320-8, and protein from an *E. coli* strain engineered to express Sh-Ble. Blots were probed with an antibody to Ble. The black arrow indicates the expected molecular weight of Ble.

A 13 kDa band (the size of Ble) was detected using the anti-Ble antibody in isolate C8 (FIG. 6). The slight difference in migration between the control proteins and the C8 preparations may reflect differences in levels of total protein loaded. No band was detected in the wild type preparations using the same amount of protein.

The assays indicate that the *Tetraselmis* nuclear genome was transformed by the ble selectable marker, which conferred Zeocin resistance on the transformant through expression of the Ble (bleomycin resistance) protein.

Example 4

Identification of *Tetraselmis* Regulatory Sequences

*Tetraselmis* genes that were expressed under nutrient replete and nutrient limited culture conditions were identified and used for the identification of regulatory sequences. To identify constitutively expressed genes, WT-105 cells were grown in nutrient-replete medium, and then shifted into either nitrogen-deficient or phosphate-deficient medium (see, Example 1, supra), while control cultures were maintained in nutrient-replete medium. For nitrogen-deprivation, cells were grown in Nutrient Replete medium, and then cultures were centrifuged and resuspended in either Nutrient Replete medium (+N), or Nitrogen Deficient medium (−N). The process for phosphate-deprivation was essentially the same, except that after centrifugation cells were shifted to one of three varieties of phosphate deficient media, containing 35, 18, or 10 μM KH$_2$PO$_4$ (see, Example 1, supra). A concentration of 140 μM of KH$_2$PO$_4$ is considered phosphate replete. Total RNA was collected before medium shift and two days post medium shift and transcripts were sequenced.

Thirty-three cDNAs were identified as exhibiting high (>1500 RPKM) transcript abundance under nutrient replete conditions as well as under both nitrogen-deprivation and phosphate-deprivation. These were analyzed for whether or not the cDNA assembly represented the entire ORF, as judged by BLAST (basic local alignment search tool; available at http://blast.ncbi.nlm.nih.gov/) results against orthologous proteins. Those cDNAs that were determined to constitute complete open reading frames (ORFs) were homology searched against a proprietary *Tetraselmis* genomic DNA (gDNA) database. BLAST hits having high confidence and representing coverage of the entire cDNA contig were selected. Six cDNAs of the thirty-three cDNAs screened provided satisfactory results. These cDNAs corresponded to genes encoding a glyceraldehyde-3-phosphate dehydrogenase (GAPDH), photosystem II reaction center W protein (PSIIw), oxygen evolving enhancer protein 3 (OEEp3), 40S ribosomal protein S12 (RB40S12), a photosystem I light harvesting complex protein (PSILHC), and the photosystem II PsbO protein (PSBo).

Promoter fragment sequences from these six genes and a terminator fragment sequence from the GAPDH gene were identified using GENESCAN® software (Applied Biosystems). Primers were designed for cloning the promoter and terminator fragment sequences. As the genomic sequence upstream of the GAPDH gene as delineated in the WT-105 genome assembly included a gap, the complete upstream sequence was cloned from genomic DNA by PCR using the GAPDH upstream primers.

Example 5

Functional Verification of Cloned Regulatory Sequences in P-925

The putative promoter fragments isolated from the 5' upstream region of the genes as identified by bioinformatic analysis of a draft genome sequence of WT-105, a wild-type strain of *Tetraselmis*, were cloned into constructs for promoter function testing. Promoter fragments were cloned as 800 bp to 1.5 kbp of sequence upstream of an identified *Tetraselmis* gene, such that the 3' end of the putative promoter fragment corresponded to the 3'-most base pair of the 5' untranslated region of the *Tetraselmis* gene (that is, the 3' end of each promoter fragment was the nucleotide immediately upstream of the initiating ATG codon of the identified gene). In addition, a 1223 bp fragment 3' of the stop codon of the WT-105 GAPDH gene (SEQ ID NO:10) was cloned as a terminator fragment.

Upstream regions of genes that were cloned for promoter fragment testing included: the glyceraldehyde 3-phosphate dehydrogenase gene upstream fragment GAPDH_P (SEQ ID NO:2); the oxygen evolving enhancer protein 1 gene upstream fragment PSBo_P (SEQ ID NO:3); photosystem II reaction center W gene upstream fragment PsIIW_P (SEQ ID NO:4); oxygen evolving enhancer protein 3 OEEp3_P (SEQ ID NO:5); 40S ribosomal protein S12 RB40S12_P (SEQ ID NO:6); and photosystem I light harvesting complex protein gene upstream fragment PSILHCdirect_P (SEQ ID NO:7). In addition, the proximity of the putative promoter fragment PSILHCdirect_P (SEQ ID NO:7) to an oppositely-oriented gene suggested that the fragment might include a bidirectional promoter. Therefore, the putative promoter-containing fragment PSILHCdirect_P (SEQ ID NO:7) was cloned in the reverse orientation (designated as PSILHCinverted_P and provided as SEQ ID NO:8) and was also tested for promoter function. The actin gene upstream fragment (SEQ ID NO:1) that demonstrated promoter activity in Example 2 was also further assessed in these transformation experiments.

Figure 7:
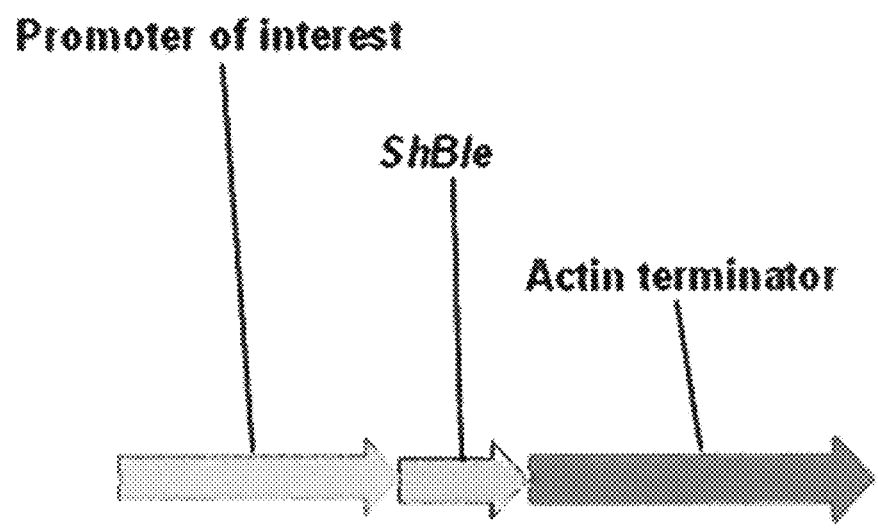
FIG. 7 is a schematic diagram depicting constructs used to transform WT-105 for promoter testing.

Putative promoter fragments were placed upstream from the Sh ble gene (SEQ ID NO:30), which was positioned immediately upstream of the WT-105 actin terminator fragment (SEQ ID NO:9) (see FIG. 7). Vectors were sequence confirmed and were linearized with restriction enzymes and transformed into *Tetraselmis* strain P-925, a classically improved derivative of WT-105 with increased lipid productivity relative to WT-105.

Example 6

Transformation into *Tetraselmis* Strain P-925

PDS-1000 Biolistics Transformation:
Although a large set of parameters were tested with the Biorad PDS-1000 gene gun for transformation of *Tetraselmis* (see, for example, Example 2), low numbers (e.g., 0-4) of Zeocin resistant colonies per bombardment resulted regardless of the conditions used.

HELIOS® Biolistics Transformation:
Plasmid DNAs were isolated from overnight *E. coli* cultures using the Invitrogen CHARGESWITCH® Pro Filter Plasmid Maxiprpep Kit and linearized with an appropriate endonuclease from New England Biolabs. Linearized plasmids were purified using a phenol/chloroform (pH 8) extraction and precipitation in 70% cold ethanol and quantitated with the Invitrogen Qubit 2.0 fluorometer.

Cartridges for the HELIOS® Gene Gun (Bio-Rad) were prepared according to the manufacturer's instructions. In brief, CaCl$_2$ and spermidine were used to precipitate 1 μg linearized plasmid onto 500 μg of 600 nm BioRad gold microcarriers per cartridge. DNA-coated microcarriers were suspended in 100% ethanol with 10 μg/mL PVP and immobilized to the inside of GOLD-COAT™ (Bio-Rad) tubing. For every 40 bullets, 20 mg gold was measured into a 1.5 mL tube to achieve 500 μg gold/shot. 100 μL of 50 mM spermidine was added, vortexed, and sonicated for 5 seconds. Plasmid DNA was added and vortexed. 100 μL of 1 M CaCl$_2$ was then added dropwise while vortexing. This mixture was incubated at room temperature for 10 minutes. Meanwhile, 30" Tefzel tubing was simultaneously dried by running nitrogen through it for 15 minutes at 0.3-0.4 LPM. The gold was then centrifuged for ~10-15 seconds. The supernatant was removed and the pellet was washed three times with 1 mL ethanol, with vortexing and centrifugation between each wash step. The pellet was resuspended in 1 mL ethanol/PVP solution (10 μg/mL of PVP in ethanol). This 1 mL slurry was then moved to a 15 mL conical tube and an additional 1.5 mL of ethanol/PVP was added. The gold suspension was vortexed and immediately pulled into the Tefzel tubing with a syringe, leaving several inches of space on both sides. Having checked to verify that the nitrogen was off, the Tefzel tubing was placed into a Prep Station, leaving the free end of the Tefzel tubing sealed with the syringe connection. The tube of gold was incubated for 5 minutes to allow the gold to settle and adhere to the Tefzel tubing. Suction was then applied with the syringe to remove the ethanol from the tubing at a rate of approximately 100 μL/second. Once the ethanol was all removed, the tubing was immediately rotated approximately 120° every five seconds for a minute. After that first minute, nitrogen was introduced at 0.1 LPM and rotation continued for another minute. After the second minute, nitrogen was increased to approximately 0.3-0.4 LPM and rotation continued for another five minutes. The tubing was then cut into half-inch cartridges and place in a sealed storage bottle with desiccant for storage at 4° C.

Two days prior to transformation, cultures of P-925 were grown to mid-log phase (between $5\times10^5$ and $1\times10^6$ cells/mL) in PM032 media. Cell counts were determined using an Accuri cytometer. Cells were grown at 25° C., 1% $CO_2$ with shaking at 125 rpm on a 16:8 light:dark cycle. On the day of transformation, cells were harvested by centrifugation at 3000×g for 5 minutes at 25° C. and re-suspended in PM032 to a concentration of $5\times10^7$ cells/mL. Fifteen 4 cm diameter circles with $1\times10^7$ cells per circle were spread on a 22×22 cm PM032 1.5% agar plate and allowed to dry. Fifteen replicate shots were fired with the HELIOS® Gene Gun (Bio-Rad) at 400 psi and 500 psi at a distance of 5 cm. The shooting plates were left at 25° C. in ambient light for 24 hours to allow cells to recover. Cells from the fifteen replicates were washed off the shooting plates with 40 mL PM032 and pooled together in a 50 mL BD Falcon tube. The samples were then pelleted at 3000×g for 5 minutes at 25° C. and re-suspended with PM032 to a final volume of 4 mL. The suspension was spread onto two 22×22 cm PM032 plates (2 mL cell suspension per plate) with 250 µg/mL Zeocin. After air-drying in a biological safety cabinet, plates were incubated under 100 µE, light at 25° C. After two weeks, colonies present on the primary selection plates were streaked for secondary selection on PM032 agar with Zeocin at 800 µg/mL. Using this method the following promoter fragments were validated: SEQ ID NO:1, SEQ ID NO:4, SEQ ID NO:5, SEQ ID NO:6, SEQ ID NO:7, and SEQ ID NO:8. The number of Zeocin 250 µg/mL colonies were recorded, and a random selection were re-streaked on Zeocin 800 µg/mL containing plates. Of those that grew on Zeocin 800 µg/mL, colony PCR was performed to confirm presence of Sh ble gene. A summary of these results are presented in Table 5 below. All promoter fragments tested demonstrated the ability to direct expression of the Sh ble gene, as was evident by the high percentages of colonies that were resistant to a high concentration (800 µg/ml) of Zeocin.

TABLE 5

Screening of HELIOS ® Gene Gun Transformants

| Promoter fragment | # Resistant to 250 µg/mL Zeocin | % Resistant to 800 µg/mL Zeocin | % Positive by PCR screen |
|---|---|---|---|
| SEQ ID NO: 1 | 629 | 25% (N = 629) | 95% (N = 145) |
| SEQ ID NO: 3 | 1150 | 97% (N = 32) | 70% (N = 31) |
| SEQ ID NO: 4 | 415 | 100% (N = 32) | 100% (N = 32) |
| SEQ ID NO: 6 | 4150 | 97% (N = 32) | 79% (N = 31) |
| SEQ ID NO: 7 | 1250 | 97% (N = 32) | 92% (N = 31) |
| SEQ ID NO: 8 | 161 | 100% (N = 32) | 100% (N = 32) |

Example 7

Figure 8:
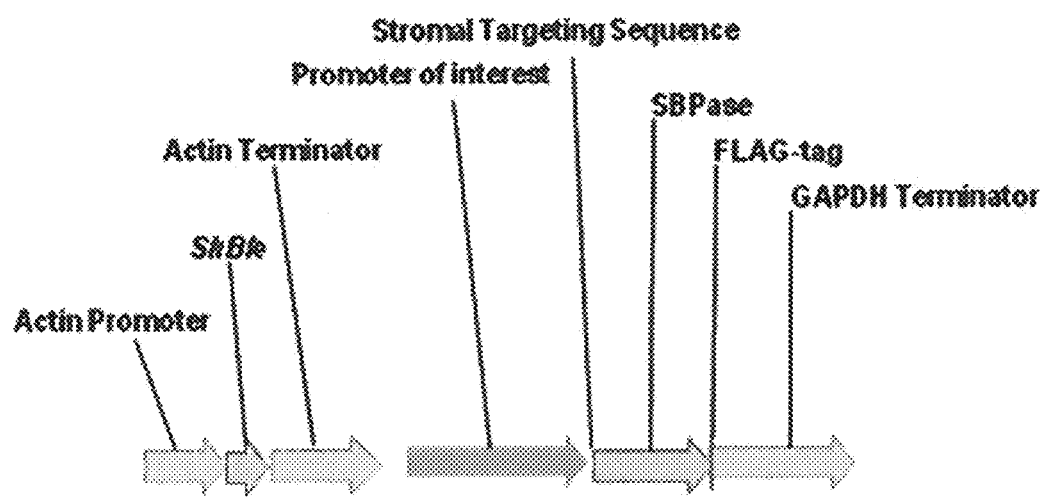
FIG. 8 is a schematic diagram depicting constructs used to transform WT-105 for promoter testing on non-selectable targets.

Cloned Regulatory Sequences in P-925 Driving Expression of a Heterologous Gene Encoding a Metabolic Enzyme The GAPDH promoter fragment (SEQ ID NO:2) and psbO promoter fragment (SEQ ID NO:3) were tested in *Tetraselmis* for their ability to drive expression of a heterologous gene encoding a metabolic enzyme. In these experiments, *Tetraselmis* strain P-925 was transformed with a plasmid that included a gene encoding a cyanobacterial sedoheptulose bisphosphatase (SBPase) engineered to include an N-terminal chloroplast stroma targeting sequence from the WT-105 SBPase (SEQ ID NO:34) and a C-terminal FLAG tag, in which the gene was operably linked to either the GAPDH promoter fragment (SEQ ID NO:1) or the psbO promoter fragment (SEQ ID NO:3) A general diagram of the p05841 and p05842 constructs that included the *Synechococcus* PCC7942 SBPase gene tagged at the C-terminus with a FLAG epitope tag and fused at the N-terminus with a stromal targeting sequence from the endogenous WT-105 SBPase gene, followed by the GAPDH terminator fragment (SEQ ID NO:10) is provided as FIG. 8. In the experiments detailed herein, the "promoter of interest" in FIG. 8 is the GAPDH promoter fragment (SEQ ID NO:2) for construct p05841 and the psbO promoter fragment (SEQ ID NO:3) for construct p05842.

Construction of p05481 and p05482 Vectors for Over-Expression of a Cyanobacterial SBPase:

Two vectors, p05464 and p05465, were synthesized for over-expressing heterologous genes in *Tetraselmis*. In addition to either the GAPDH promoter fragment (SEQ ID NO:2) or the psbO promoter fragment (SEQ ID NO:3), paired with the GAPDH terminator fragment (SEQ ID NO:10) for target gene expression, these plasmids both included the Zeocin resistance cassette derived from p05320 (the Sh ble gene operably linked to the WT-105 actin promoter fragment (SEQ ID NO:1) and the WT-105 actin terminator fragment (SEQ ID NO:9)) (see FIG. 8). p05464 was assembled by PCR amplifying and gel purifying DNA fragments, which were eventually assembled into the vector. Each fragment was designed to have 15-40 bases of overlap to neighboring fragments to enable homology based cloning. The following DNA fragments were used to assemble p05464: A) a 2.1 kbp cloning backbone from pUC19 vector containing the beta-lactamase selectable marker and origin of replication for *E. coli*; B) an algal selectable marker cassette containing the bleomycin resistance gene (SEQ ID NO:30) under the control of WT-105 actin promoter (SEQ ID NO:1) and WT-105 actin terminator (SEQ ID NO:9); as well as C) a WT-105 GAPDH promoter fragment (SEQ ID NO:2); and D) a WT-105 GAPDH terminator fragment (SEQ ID NO:10) positioned in tandem such that a gene of interest could be inserted between the GAPDH promoter (C) and the GAPDH terminator (D). Fragments A-D were assembled by Gibson Assembly to produce expression vector p05464. Vector p05465 was assembled in the same manner, but with a WT-105 psbO promoter fragment for element C (SEQ ID NO:3). The *Synechococcus elongatus* PCC7942 sedoheptulose-1,7-bisphosphatase encoding gene (SBPase, Genbank accession: BAA08536, SEQ ID NO:33) was inserted into expression vector p05464 downstream of the GAPDH promoter fragment to create p05481 and inserted into expression vector p05465 downstream of the psbO promoter fragment to create p05482. In both constructs, a nucleotide sequence encoding an N-terminal 61 amino acid chloroplast targeting sequence (SEQ ID NO:34) from the WT-105 SBPase gene (SEQ ID NO:33) and a nucleotide sequence encoding a C-terminal FLAG epitope tag were added upstream and downstream of the SBPase encoding sequence, respectively, using the Gibson Assembly method.

*Tetraselmis* P-925 cells were transformed with a using a HELIOS® gene gun according to the method provided in Example 6. Zeocin resistant colonies were selected as described above, and lines were further assessed for SBPase protein expression by western blotting.

Figure 9:
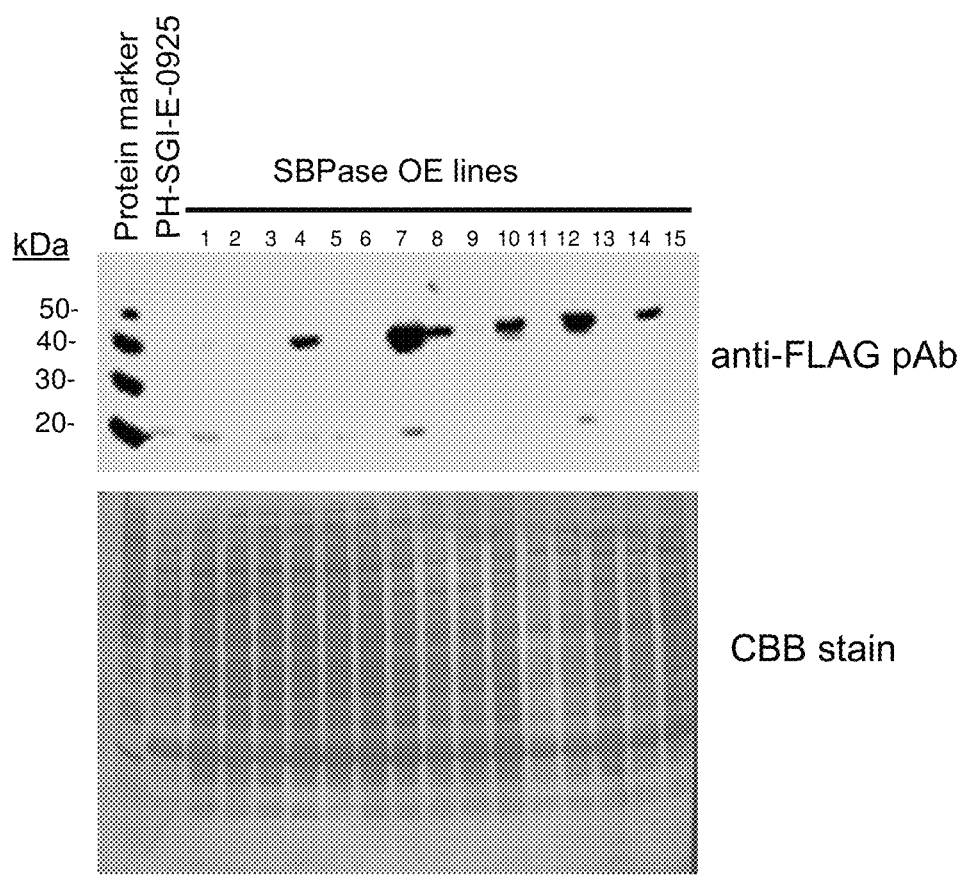
FIG. 9 is a western blot (upper panel) analysis of putative SBPase over-expressing lines of PH-925 generated by transformation with p05481. 30 µg total proteins from each sample were separated on 12% SDS-PAGE gels, which were processed for western blotting using the anti-FLAG peptide antibody (anti-FLAG pAb). After chemiluminescent detection, the blot was stained (lower panel) with Coomassie brilliant blue (CBB stain) to assess relative levels of protein loaded. Lanes 4, 7, 8, 10, 12, and 14 show FLAG-tagged protein. A protein molecular weight marker (Magic Mark II, Invitrogen) was included and marker masses are indicated at left.

Accumulation of the recombinant protein in transgenic lines was detected using by immunoblotting with an anti-FLAG epitope tag antibody (see FIG. 9). Total cellular proteins were extracted in EZ buffer (Martinez-Garcia et al. (1999) *Plant J.* 20:251-57) by treatment in a water bath sonicator for approximately 30 seconds, followed by denaturation at 85° C. for 10 minutes with occasional vortexing. Total protein concentration was determined using the BioRad RCDC protein assay kit. SDS-PAGE gels were loaded on an equal total protein basis and proteins were separated by electrophoresis. Proteins were transferred to PVDF membranes using the Invitrogen iBLOT® dry blot system (Life Technologies, Carlsbad, Calif.) using program #3, for 7 minutes. Membranes were blocked for at least 90 minutes in tris-buffered saline (TBS) containing 5% powdered milk and 0.15% Tween 20 (TBST), followed by incubation with primary antibodies and HRP-conjugated secondary antibody (Biorad goat anti-rabbit IgG, diluted 1:40000 in TBST-milk). Antibodies used in this report included anti-AGPase (AS11 1739, Agrisera), rabbit polyclonal peptide antibody recognizing FLAG epitope tags, and Bip2 (AS09 481, Agrisera). Immuno-reacting bands were detected with Chemiluminescent peroxidase substrate (Sigma-Aldrich) and imaged with the MULTIIMAGE® II (Alpha Innotech) gel imaging station.

A ~40 kDa band (the expected mass if the chloroplast targeting sequence is properly cleaved) was observed in 19 of 49 p05481 derived lines, and 5 of 23 p05482 derived lines. These results indicate that transgenic protein was detected in ~20-40% of transgenic lines, as summarized in Table 6 below. As such, the promoter function of both the GAPDH promoter fragment (SEQ ID NO:2) and the psbO promoter fragment (SEQ ID NO:3) has been confirmed.

TABLE 6

Summary of results from driving transgene expression

| Promoter fragment | # Lines tested | % Zeocin$^R$ & FLAG$^+$ |
|---|---|---|
| GAPDH | 50 | 42 |
| psbO | 20 | 20 |

Regulatory elements have been identified from *Tetraselmis* to use in recombinant protein expression in eukaryotic cells, particularly microalgae. Further, the inventors have discovered that transformation of *Tetraselmis* using a biolistic method results in greater than 100 transformants per day even though *Tetraselmis* has been known to be difficult to stably transform. Transgenic protein over-expression was shown to be readily achievable in *Tetraselmis* using the transformation protocol established in this report.

Example embodiments are provided so that this disclosure will be thorough, and will fully convey the scope to those who are skilled in the art. Numerous specific details are set forth such as examples of specific components and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known structures, and well-known technologies are not described in detail.

An index of all of the sequences detailed in this application is set forth below in Table 7.

TABLE 7

Index of Sequence Listings

| SEQ ID NO: | Description |
|---|---|
| 1 | *Tetraselmis* Actin promoter fragment |
| 2 | *Tetraselmis* GAPDH promoter fragment |
| 3 | *Tetraselmis* psbO promoter fragment |
| 4 | *Tetraselmis* PS-II W promoter fragment |
| 5 | *Tetraselmis* OEE p3 promoter fragment |
| 6 | *Tetraselmis* RB40 S12 promoter fragment |
| 7 | *Tetraselmis* PS-I HLC direct promoter fragment |
| 8 | *Tetraselmis* PS-I HLC inverted promoter fragment |
| 9 | *Tetraselmis* Actin terminator fragment |
| 10 | *Tetraselmis* GAPDH terminator fragment |
| 11 | WT105ActinPro-EcoRI primer |
| 12 | WT105ActinPro-BLE-3 primer |
| 13 | WT105ActinTER-BLE-5 primer |
| 14 | WT105ActinTER-HindIII primer |
| 15 | BLE-ActinWT105-5 primer |
| 16 | BLE-ActinWT105-3 primer |
| 17 | WT105ActinPro-PciI primer |
| 18 | WT105ActinPro-GFP-3 primer |
| 19 | WT105ActinTER-GFP-5 primer |
| 20 | WT105ActinTER-PciI primer |
| 21 | GFP-ActinWT105-5 primer |
| 22 | GFP-ActinWT105-3 primer |
| 23 | BLE-5 primer |
| 24 | BLE-3 primer |
| 25 | NaHtransB5 primer |
| 26 | NaHtransC3 primer |
| 27 | LF-SGE5320F1 primer |
| 28 | BLEcodon3 primer |
| 29 | p05320 |
| 30 | Sh ble gene |
| 31 | *C. reinhardtii* actin gene |
| 32 | *C. reinhardtii* psaD |
| 33 | WT-105 SBPase gene |
| 34 | WT-105 SBPase |
| 35 | WT-105 SBPase chloroplast targeting sequence gene |
| 36 | WT-105 SBPase chloroplast targeting sequence |

What is claimed is:

1. An expression cassette comprising a heterologous nucleic acid sequence encoding a protein or functional RNA, operably linked to a promoter comprising a nucleotide sequence selected from the group consisting of a nucleotide sequence having at least 95% identity to at least 300 contiguous nucleotides from the 3' end of SEQ ID NO:1; a nucleotide sequence having at least 95% identity to at least 300 contiguous nucleotides from the 3' end of SEQ ID NO:2; a nucleotide sequence having at least 95% identity to at least 300 contiguous nucleotides from the 3' end of SEQ ID NO:3; a nucleotide sequence having at least 95% identity to at least 300 contiguous nucleotides from the 3' end of SEQ ID NO:4; a nucleotide sequence having at least 95% identity to at least 300 contiguous nucleotides from the 3' end of SEQ ID NO:5; a nucleotide sequence having at least 95% identity to at least 300 contiguous nucleotides from the 3' end of SEQ ID NO:6; a nucleotide sequence having at least 95% identity to at least 300 contiguous nucleotides from the 3' end of SEQ ID NO:7; and a nucleotide sequence having at least 95% identity to at least 300 contiguous nucleotides from the 3' end of SEQ ID NO:8.

2. An expression cassette comprising a heterologous nucleic acid sequence encoding a protein or functional RNA, operably linked to a promoter comprising a nucleotide sequence selected from the group consisting of a nucleotide sequence having 100% identity to at least 100 contiguous nucleotides from the 3' end of SEQ ID NO:1; a nucleotide sequence having 100% identity to at least 100 contiguous nucleotides from the 3' end of SEQ ID NO:2; a nucleotide sequence having 100% identity to at least 100 contiguous nucleotides from the 3' end of SEQ ID NO:3; a nucleotide sequence comprising having 100% identity to at least 100 contiguous nucleotides from the 3' end of SEQ ID NO:4; a nucleotide sequence having 100% identity to at least 100 contiguous nucleotides from the 3' end of SEQ ID NO:5; a nucleotide sequence having 100% identity to at least 100 contiguous nucleotides from the 3' end of SEQ ID NO:6; a nucleotide sequence having 100% identity to at least 100 contiguous nucleotides from the 3' end of SEQ ID NO:7; and a nucleotide sequence having 100% identity to at least 100 contiguous nucleotides from the 3' end of SEQ ID NO:8.

3. The expression cassette according to claim 1, wherein the promoter is a constitutive promoter.

4. The expression cassette according to claim 1, wherein the nucleic acid sequence encoding a protein or functional RNA is further operably linked to a terminator having a nucleotide sequence selected from the group consisting of a nucleotide sequence having at least 95% identity SEQ ID NO:9; and a nucleotide sequence having at least 95% identity to SEQ ID NO:10.

5. The expression cassette according to claim 1, wherein the nucleic acid sequence encoding a protein or functional RNA encodes a polypeptide.

6. The expression cassette according to claim 5, wherein the nucleic acid sequence encoding a protein or functional RNA encodes (a) a protein associated with lipid biosynthesis, (b) a protein having lipolytic activity, (c) a photosynthetic protein, (d) a carbon fixation protein, (e) a transporter protein, (f) a dehydrogenase, (g) a transcription factor, or (h) a cell signaling protein.

7. The expression cassette according to claim 1, wherein the nucleic acid sequence encoding a protein or functional RNA encodes a functional RNA selected from the group consisting of an antisense sequence, a micro RNA, a shRNA, an siRNA, and a ribozyme.

8. A vector comprising an expression cassette according to claim 1.

9. The vector according to claim 8, further comprising a selectable marker or reporter gene.

10. The vector according to claim 8, further comprising a terminator having a nucleotide sequence selected from the group consisting of a nucleic acid sequence having at least 95% identity to SEQ ID NO:9 and a nucleic acid sequence having at least 95% identity to SEQ ID NO:10; wherein the terminator is operably linked to the nucleic acid sequence encoding a protein or a functional RNA and/or the terminator is downstream of the nucleic acid sequence encoding a protein or a functional RNA.

11. The vector according to claim 8, wherein the vector includes at least one origin of replication.

12. The vector according to claim 9, further comprising a promoter operably linked to the selectable marker or reporter gene.

13. The vector according to claim 9, wherein the selectable marker or reporter gene is selected from the group consisting of a gene conferring resistance to an antibiotic, a gene conferring resistance to an herbicide, a gene encoding acetyl CoA carboxylase (ACCase), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS, a gene encoding a non-class I/II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acetyl transferase, a gene encoding phytoene desaturase, a gene encoding prenyl transferase, a gene encoding protoporphyrin oxidase, a gene encoding superoxide dismutase, arg7, his3, hisD, hisG, manA, nit1, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene; an R-locus gene, a tyrosinase gene, lacZ, an alkaline phosphatase gene, an α-amylase gene, a horseradish peroxidase gene, an α-galactosidase gene, a luciferin/luciferase gene, a beta-glucuronidase gene (GUS), and a gene encoding a fluorescent protein.

14. A method for transforming a eukaryotic cell comprising: introducing a vector according to claim 8 into the eukaryotic cell; and selecting for a transformed eukaryotic cell.

15. The method according to claim 14, wherein the vector is introduced by a biolistic procedure.

16. The method according to claim 15, wherein about 300 psi or more of pressure is used to impel biolistic microcarriers coated with vector DNA into the eukaryotic cell.

17. The method according to claim 14, wherein the transformed eukaryotic cell is stably transformed.

18. The method according to claim 14, wherein the eukaryotic cell is selected from the group consisting of a fungal cell, a heterokont cell, an algal cell, and a plant cell.

19. The method according to claim 18, wherein the eukaryotic cell is an algal cell.

20. The method according to claim 19, wherein the algal cell is from a species selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Emodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetraselmis, Thalassiosira, Tribonema, Vaucheria, Viridiella, Vischeria*, and *Volvox*.

21. The method according to claim 20, wherein the algal cell is a *Tetraselmis* algal cell.

22. A method for co-transforming a eukaryotic cell comprising:
  introducing an expression cassette according to claim 1 and a nucleic acid sequence encoding a selectable marker into the eukaryotic cell; and selecting for the presence of the selectable marker in a transformed eukaryotic cell to provide a eukaryotic cell transformed with the expression cassette.

23. The method according to claim 22, wherein the eukaryotic cell is an algal cell.

24. The method according to claim 22, wherein the selectable marker gene is selected from the group consisting of a gene conferring resistance to an antibiotic, a gene conferring resistance to an herbicide, a gene encoding acetyl CoA carboxylase (ACCase), a gene encoding acetohydroxy acid synthase (ahas), a gene encoding acetolactate synthase, a gene encoding aminoglycoside phosphotransferase, a gene encoding anthranilate synthase, a gene encoding bromoxynil nitrilase, a gene encoding cytochrome P450-NADH-cytochrome P450 oxidoreductase, a gene encoding dalapon dehalogenase, a gene encoding dihydropteroate synthase, a gene encoding a class I 5-enolpyruvylshikimate-3-phosphate synthase (EPSPS), a gene encoding a class II EPSPS, a gene encoding a non-class I/II EPSPS, a gene encoding glutathione reductase, a gene encoding glyphosate acetyltransferase, a gene encoding glyphosate oxidoreductase, a gene encoding hydroxyphenylpyruvate dehydrogenase, a gene encoding hydroxy-phenylpyruvate dioxygenase, a gene encoding isoprenyl pyrophosphate isomerase, a gene encoding lycopene cyclase, a gene encoding phosphinothricin acetyl transferase, a gene encoding phytoene desaturase, a gene encoding prenyl transferase, a gene encoding protoporphyrin oxidase, a gene encoding superoxide dismutase, arg7, his3, hisD, hisG, manA, nit1, trpB, uidA, xylA, a dihydrofolate reductase gene, a mannose-6-phosphate isomerase gene, a nitrate reductase gene, an ornithine decarboxylase gene, a thymidine kinase gene, a 2-deoxyglucose resistance gene; and an R-locus gene.

25. The method according to claim 22, wherein the selectable marker gene is operably linked to a promoter active in the eukaryotic cell.

26. The method according to claim 22, wherein the expression cassette and the nucleic acid sequence encoding a selectable marker are present in the same vector.

27. The method according to claim 23, wherein the algal cell is from a species selected from the group consisting of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria,* and *Volvox.*

28. The method according to claim 27, wherein the algal cell is a *Tetraselmis* algal cell.

29. A eukaryotic host cell comprising an expression cassette according to claim 1.

30. The eukaryotic host cell according to claim 29, wherein the eukaryotic host cell is an algal cell.

\* \* \* \* \*